US011712432B2

(12) United States Patent
Gentry et al.

(10) Patent No.: US 11,712,432 B2
(45) Date of Patent: Aug. 1, 2023

(54) METHOD OF TREATING CANCER WITH AN ELEVATED GLYCOGEN CONTENT

(71) Applicant: University of Kentucky Research Foundation, Lexington, KY (US)

(72) Inventors: Matthew S. Gentry, Lexington, KY (US); Ramon C. Sun, Lexington, KY (US); Lyndsay EA Young, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 16/724,126

(22) Filed: Dec. 20, 2019

(65) Prior Publication Data

US 2020/0215031 A1    Jul. 9, 2020

Related U.S. Application Data

(60) Provisional application No. 62/782,957, filed on Dec. 20, 2018.

(51) Int. Cl.
*A61K 31/40* (2006.01)
*A61P 35/00* (2006.01)
*A61K 31/085* (2006.01)
*A61K 45/06* (2006.01)

(52) U.S. Cl.
CPC ............ *A61K 31/40* (2013.01); *A61K 31/085* (2013.01); *A61P 35/00* (2018.01); *A61K 45/06* (2013.01)

(58) Field of Classification Search
CPC ..................................................... A61K 31/40
USPC ........................................................ 514/425
See application file for complete search history.

(56) References Cited

U.S. PATENT DOCUMENTS 11,236,339 B2    2/2022  Grossman et al.
2010/0166701 A1*  7/2010  Parker ................ A61K 38/2013
                                                            424/85.2

FOREIGN PATENT DOCUMENTS

WO    2017/120420 A1 *  7/2017

OTHER PUBLICATIONS

Daniel-Marechal et al., Expert Opinion on Therapeutic Patents (2016) vol. 26(2), pp. 199-212.*
Christos et al., J. Mol. Med. (2016) 94: 137-154.*
Ardourel et al., Canc. Biology & Therapy (2007) vol. 6(5), pp. 719-723.*
Bhanot et al., (2015), 29:1555-1563.*
Baba, et al. Production of monoclonal antibody that recognizes glycogen and its application for immunohistochemistry. Kokubyo Gakkai Zasshi 60, 264-287 (1993).
Baird, E. R. Fisher, Observations concerning vacuolation and deposition of glycogen in nuclei of hepatic cells. Lab Invest 6, 324-333 (1957).
Bloom, G. T. Lewis, M. Z. Schumpert, T. M. Shen, Glycogen fractions of liver and muscle. Journal of Biological Chemistry 188, 631-636 (1951).
Boukouris, S. D. Zervopoulos, E. D. Michelakis, Metabolic Enzymes Moonlighting in the Nucleus: Metabolic Regulation pf Gene Transcription. Trends in Biochemical Sciences 41, 712-730 (2016).
Chung, J.K., et al., Comparison of F-18 fluorodeoxyglucose uptake with glucose transporter-1 expression and proliferation rate in human glioma and non-small-cell lung cancer. Nuclear Medicine Communications, 2004. 25.
Donohue, et al. 2020. The E3 ligase malin plays a pivotal role in promoting nuclear glycogenolysis and histone acetylation. Annals of Translational Medicine. 8 (5): 254.
Gentry, et al, Lafora disease offers a unique window into neuronal glycogen metabolism. Journal of Biological Chemistry 293, 7117-7125 (2018).
Gentry, et al, Laforin, a protein with many faces: glucan phosphatase, adapter protein, et alii. Febs J, 2013. 280(2): p. 525-37.
Gentry, M.S., J.E. Dixon, and C.A. Worby, Lafora disease: insights into neurodegeneration from plant metabolism. Trends Biochem Sci, 2009. 34(12): p. 628-39.
Granzow, M. Kopun, H. P. Zimmermann, Role of nuclear glycogen synthase and cytoplasmic UDP glucose pyrophosphorylase in the biosynthesis of nuclear glycogen in HD33 Ehrlich-Lettré ascites tumor cells. The Journal of Cell Biology 89, 475(1981).
Grünewald, T.G.P., et al., Ewing sarcoma. Nature Reviews Disease Primers, 2018. 4(1): p. 5. in 58 Cultured Human Tumor Cell Lines of Various Tissue Origins. Cancer Research 41, 1165-1170(1981).
Kakhlon, O., et al., Guaiacol as a drug candidate for treating adult polyglucosan body disease. JCI Insight, 2018. 3(17).
Kakhlon, O., et al., Guaiacol can be a drug-candidate for treating Adult Polyglucosan Body Disease (P5.461). Neurology, 2018. 90(15 Supplement).
Lyndsay E.A. Young, Corey O. Brizzee, Jessica K.A. Macedo, Matthew S. Gentry, Ramon C. Sun. 2020. Accurate and sensitive quantitation of glucose and glucose phosphates derived from storage carbohydrates using gas chromatography mass spectrometry. Carbohydrate Polymers. 230: 115651.
McBride, A., et al., The Glycogen-Binding Domain on the AMPK β Subunit Allows the Kinase to Act as a Glycogen Sensor. Cell Metabolism, 2009. 9(1): p. 23-34.
Nagata, R. S. Redman, R. Lakshman, Isolation of intact nuclei of high purity from mouse liver. Analytical Biochemistry 398, 178-184 (2010).
Ramon C. Sun, Vikas V. Dukhande, Shane Emanuelle, Lyndsay E.A. Young, Zhengqiu Zhou, Christine Brainson, Matthew S. Gentry. 2019. Altered histone acetylation in non-small cell lung cancer from impaired nuclear glycogenolysis. Cell Metabolism. 30 (5): 903-916.

(Continued)

*Primary Examiner* — Taofiq A Solola
(74) *Attorney, Agent, or Firm* — Stites & Harbison PLLC; Mandy Wilson Decker; Gary N. Stewart

(57) ABSTRACT

A method of treating cancer is provided. The method includes administering to a subject in need thereof an effective amount of a compound selected from the group consisting of a glycogen phosphorylase inhibitor, a glycogen synthase inhibitor, a glycogen degradation molecule, an anti-sense oligonucleotide that down-regulates glycogen synthesis, and combinations thereof, where the cancer includes elevated levels of glycogen.

7 Claims, 30 Drawing Sheets

(56) References Cited

OTHER PUBLICATIONS

Roach, P.J., et al., Glycogen and its metabolism: some new developments and old themes. The Biochemical journal, 2012. 441(3): p. 763-787.
Romá-Mateo, P. Sanz, M. S. Gentry, Deciphering the role of malin in the Lafora progressive myoclonus epilepsy. IUBMB life 64, 801-808 (2012).
Rousset, et al., Glycogen storage in foetal and malignant epithelial cells of the human colon. Front Gastrointest Res 4, 80-85 (1979).
Rousset, M., A. Zweibaum, and J. Fogh, Presence of Glycogen and Growth-related Variations in 58 Cultured Human Tumor Cell Lines of Various Tissue Origins. Cancer Research, 1981. 41(3): p. 1165-1170.
Rousset, M., et al., Kinetics of glycogen levels in asynchronous and synchronous cultures of a human colon carcinoma cell line, HT 29. Front Gastrointest Res, 1979. 4: p. 73-9.
Rousset, M., et al., Presence and Cell Growth-related Variations of Glycogen in Human Colorectal Adenocarcinoma Cell Lines in Culture. Cancer Research, 1979. 39(2 Part 1): p. 531-534.
Sato, A., et al., Glycogen-rich clear cell carcinoma of the breast showing carcinomatous lymphangiosis and extremely aggressive clinical behavior. Pathol Int, 2015. 65(12): p. 674-6.
Shaw, R.J., et al., The tumor suppressor LKB1 kinase directly activates AMP-activated kinase and regulates apoptosis in response to energy stress. Proceedings of the National Academy of Sciences, 2004. 101(10): p. 3329-3335.
Staedel, C. and J.-P. Beck, Resurgence of glycogen synthesis and storage capacity in cultured hepatoma cells. Cell Differentiation, 1978. 7(1): p. 61-71.
Sun et al., Noninvasive liquid diet delivery of stable isotopes into mouse models for deep metabolic network tracing. Nature Communications 8, 1646 (2017).
Sun, et al., Hypoxic Regulation of Glutamine Metabolism through HIF1 and SIAH2 Supports Lipid Synthesis that Is Necessary forTumor Growth. Cell Metabolism, 2014. 19(2): p. 285-292.
Sun et al., Nuclear Glycogenolysis Modulates Histone Acetylation in Human Non-Small Cell Lung Cancers, Cell Metabolism, 2019, 30, 903-916.
Sutendra et al., A Nuclear Pyruvate Dehydrogenase Complex Is Important for the Generation of Acetyl-CoA and Histone Acetylation. Cell 158, 84-97 (2014).
Wellen et al., ATP-Citrate Lyase Links Cellular Metabolism to Histone Acetylation. Science 324, 1076 (2009).
Zhou, et al. Clinical features, survival and prognostic factors of glycogen-rich clear cell carcinoma (GRCC) of the breast in the U.S. population. Journal of Clinical Medicine. 2019, 8(2).
Zhou, et al. Clear Cell Adenocarcinoma of the Urinary Bladder is a Glycogen-Rich Tumor with Poorer Prognosis. Journal of Clinical Medicine. 9(1), 138: 2020, 1-11.
Zimmermann, V. Granzow, C. Granzow, Nuclear glycogen synthesis in ehrlich ascites cells. Journal of Ultrastructure Research 54, 115-123 (1976).
Zois, C.E. and A.L. Harris, Glycogen metabolism has a key role in the cancer microenvironment and provides new targets for cancer therapy. Journal of Molecular Medicine, 2016. 94(2): p. 137-154.
Clayton, et al., Antisense Oligonucleotide-mediated Suppression of Muscle Glycogen Synthase 1 Synthesis as an Approach for Substrate Reduction Therapy of Pompe Disease, Molecular Therapy—Nucleic Acids (2014) 3, e206.
Fuchs, et al., Proteomic Analysis of Ribosomes: Translational Control of mRNA Populations by Glycogen Synthase GYS1, J. Mol. Biol. (2011) 410, 118-130.
Shi, et al., Glycogen Metabolism and Rheumatoid Arthritis: The Role of Glycogen Synthase 1 in Regulation of Synovial Inflammation via Blocking AMP-Activated Protein Kinase Activation, Frontiers in Immunology, Jul. 2018, vol. 9, p. 1-16.

\* cited by examiner

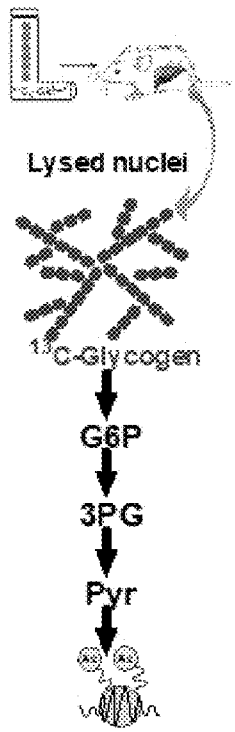
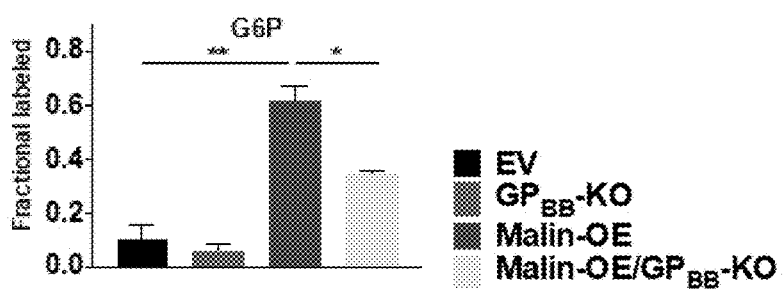
FIG. 3A
FIG. 3B
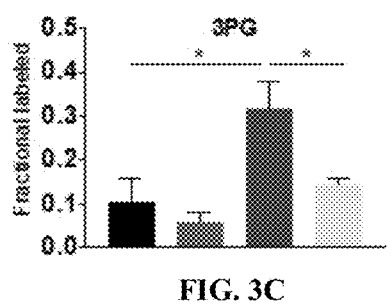
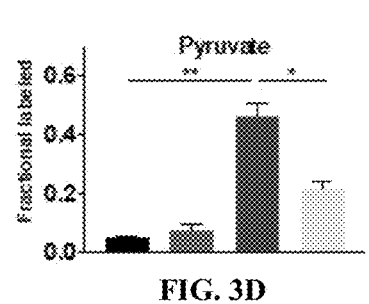
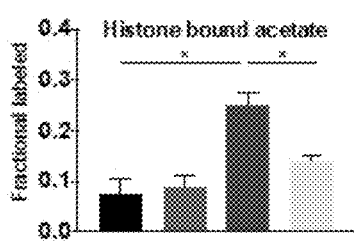
FIG. 3C
FIG. 3D
FIG. 3E
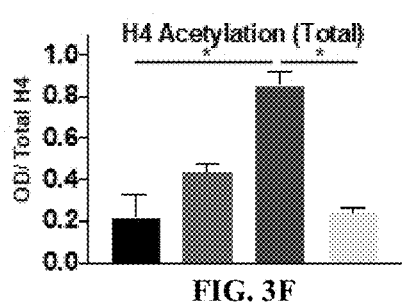
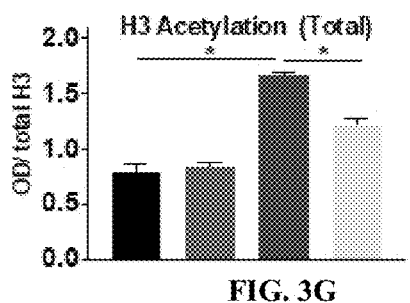
FIG. 3F
FIG. 3G

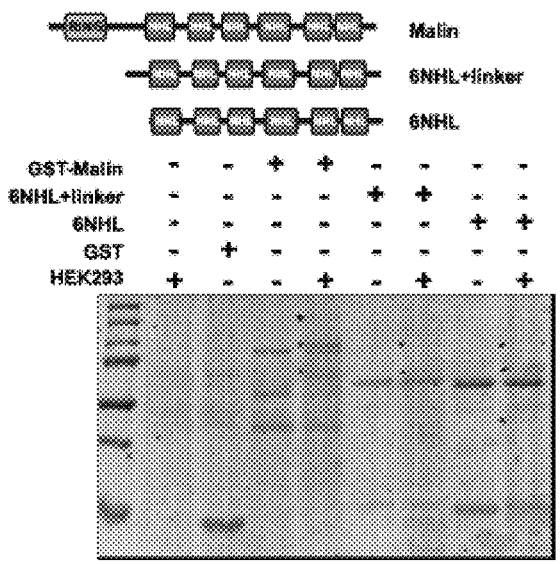
FIG. 10A
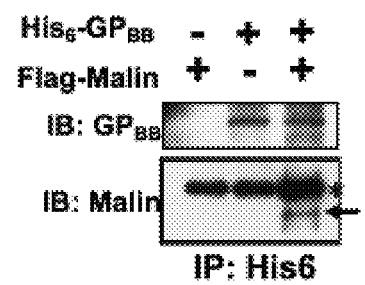
FIG. 10B
FIG. 10C
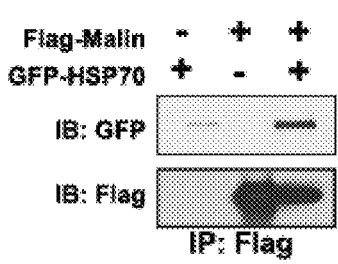 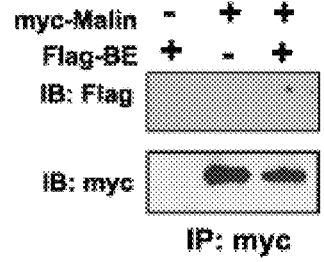 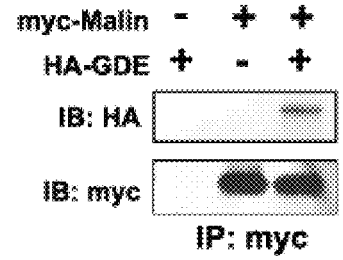
FIG. 10D        FIG. 10E        FIG. 10F

Xenograft

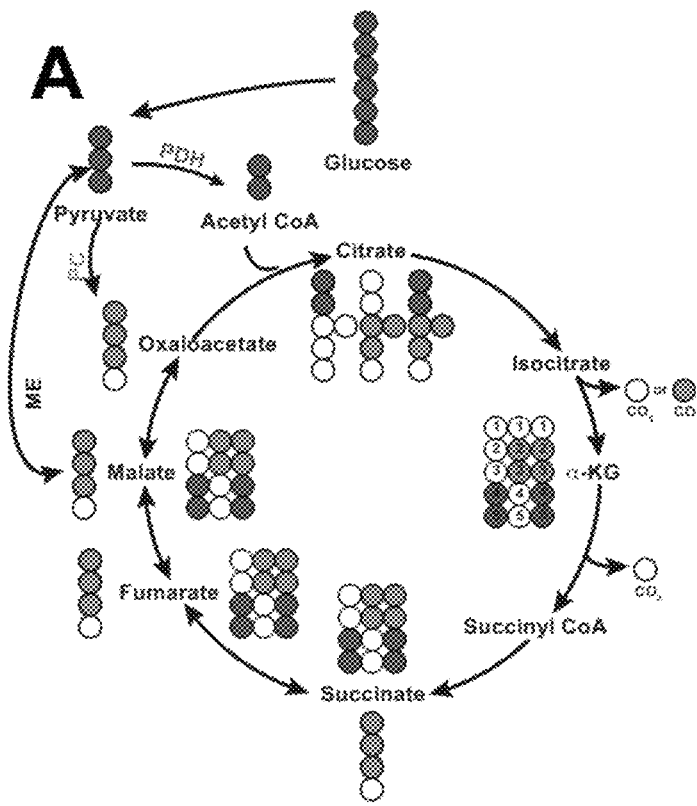
FIG. 29A
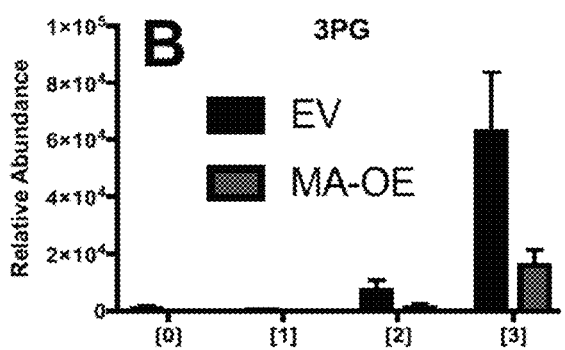 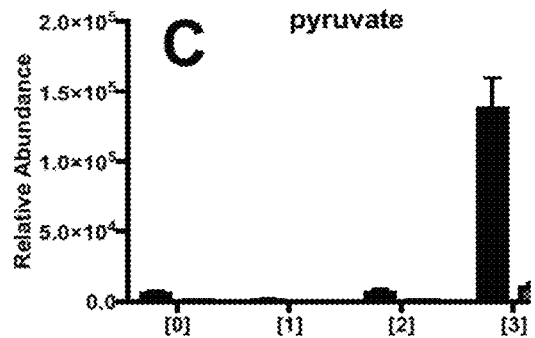
FIG. 29B  FIG. 29C

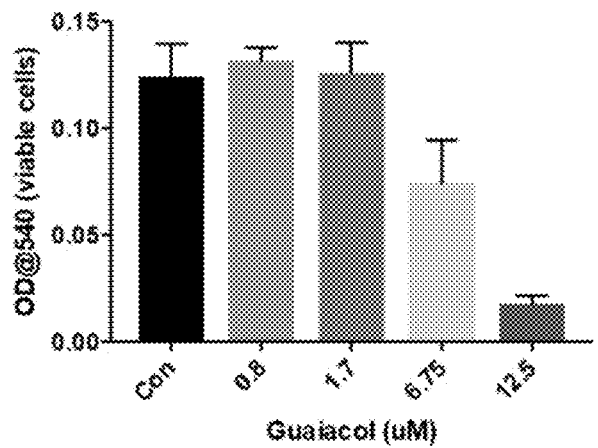
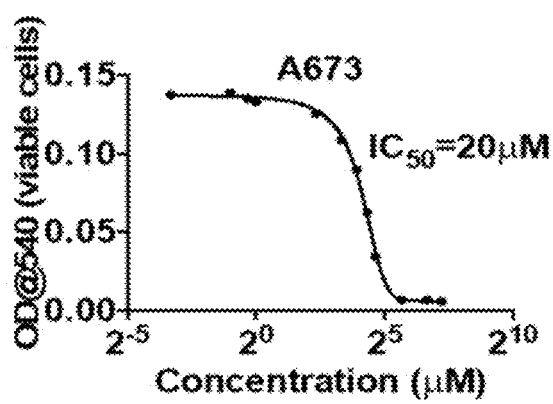
FIG. 31A  FIG. 31B
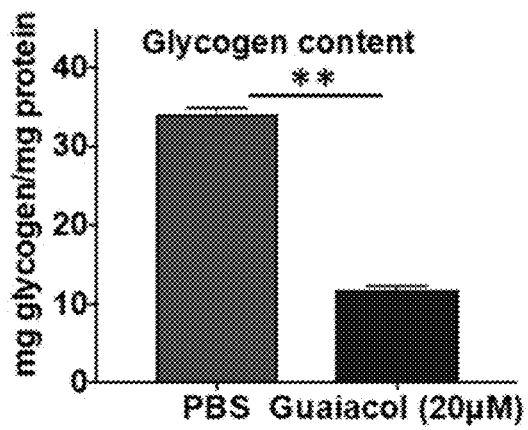
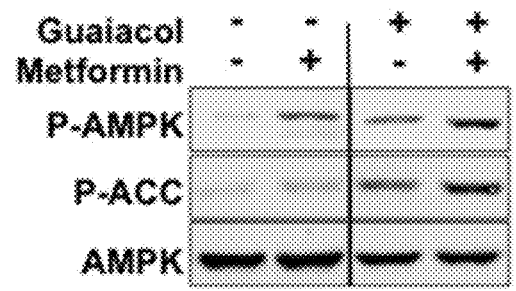
FIG. 31C  FIG. 31D
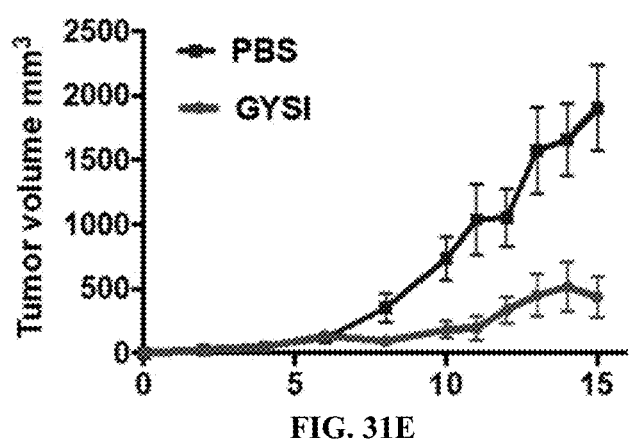
FIG. 31E

METHOD OF TREATING CANCER WITH AN ELEVATED GLYCOGEN CONTENT

RELATED APPLICATIONS

This application claims the benefit of U.S. Provisional Application Ser. No. 62/782,957, filed Dec. 20, 2018, the entire disclosure of which is incorporated herein by this reference.

GOVERNMENT INTEREST

This invention was made with government support under grant number P20GM121327 awarded by the National Institutes of Health. The government has certain rights in the invention.

TECHNICAL FIELD

The presently-disclosed subject matter generally relates to treatment of cancer with an elevated glycogen content. In particular, certain embodiments of the presently-disclosed subject matter relate to treatment of non-small cell lung cancer, clear cell renal cancer carcinoma, Ewing sarcoma, and glycogen rich clear cell carcinoma of the breast.

BACKGROUND

Glycogen is the primary source of storage carbohydrate in mammals and primarily functions as an energy cache. Abnormal glycogen metabolism has deleterious effects in a range of diseases including cancer, neurodegeneration, and congestive heart failure. However, glycogen also has other key roles beyond functioning as a simple energy reserve. Nuclear glycogen was first reported in the 1950s in hepatocytes, suggesting compartmentalized regulation, but its role in cellular physiology remained unanswered.

Ewing's sarcoma (ES) is the second most common pediatric bone malignancy affecting ~10,000 children, adolescents, and young adults worldwide each year. Approximately half of all patients with Ewing sarcoma will at some point develop either recurrent or metastatic disease, with less than 20% of such patients having long-term survival. The standard of care for ES patients includes multi-agent chemotherapy to treat documented or potential metastatic disease, coupled with surgery and/or irradiation to treat the primary tumor. Although some incremental advances have been made in the last three decades through intensification of conventional chemotherapy agents, more significant improvements will likely depend on the identification of novel treatment strategies.

In the 1970s and 1980s, elevated glycogen was detected in multiple cancer cell lines, including breast, kidney, uterus, bladder, ovary, skin, brain, and more recently colorectal cancer tissues. Hypoxia, a key characteristic of solid tumors, can induce glycogen synthesis in certain cancer sub-types, although the exact mechanism of this phenotype is yet to be resolved. Recently, hypoxia-induced glycogen phosphorolysis (the breakdown of glycogen into glucose) was shown to enhance tumorigenesis by suppressing reactive oxygen species levels and p53-dependent senescence in breast and colon cancer cells. Several studies also suggest that some cancer cells accumulate glycogen as a stored energy source to enable survival and sustain metastases under adverse conditions, such as hypoxia and glucose deprivation. Despite these findings, the roles of glycogen metabolism and associated enzymes in tumorigenesis and cancer are poorly understood.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

In some embodiments, the presently-disclosed subject matter includes a method of treating cancer comprising administering to a subject in need thereof an effective amount of a compound selected from the group consisting of a glycogen phosphorylase inhibitor, a glycogen synthase inhibitor, a glycogen degradation molecule, an anti-sense oligonucleotide that down-regulates glycogen synthesis, and combinations thereof; wherein the cancer includes elevated levels of glycogen. In some embodiments, the cancer is selected from the group consisting of non-small cell lung cancer, clear cell renal cancer carcinoma, Ewing's sarcoma, and glycogen rich clear cell carcinoma of the breast.

In one embodiment, the compound is the glycogen phosphorylase inhibitor. In another embodiment, the glycogen phosphorylase inhibitor is selected from the group including 1,4-dideoxy-1,4-imino-D-Arabinitol (DAB), 1-(3-(3 -(2-Chloro-4,5-difluorobenzoyl)ureido)-4-methoxyphenyl)-3-methylurea (GPI), 5-Chloro-N-[(1 S,2R)-3 -(dimethylamino)-2-hydroxy-3-oxo-1-(phenylmethyl)propyl]-1H-indole-2-carboxamide (CP-91149), and 5-Chloro-N-[(1S, 2R)-2-hydroxy-3-(methoxymethylamino)-3-oxo-1-(phenylmethyl)propyl]-1H-indole-2-carboxamide (CP-316819). In another embodiment, the glycogen phosphorylase inhibitor is DAB. In a further embodiment, the cancer is non-small cell lung cancer. In one embodiment, the compound is the glycogen synthase inhibitor. In another embodiment, the glycogen synthase inhibitor is 2-methoxyphenol (Guaiacol). In a further embodiment, the cancer is Ewing's sarcoma. In one embodiment, the compound is the glycogen degradation molecule. In another embodiment, the glycogen degradation molecule is fusion protein VAL-0417 (Valerion) or antibody-enzyme fusion VAL-1221 (Valerion). In one embodiment, the compound is the anti-sense oligonucleotide that down-regulates glycogen synthesis.

In some embodiments, the method further includes administering an additional therapeutic to the subject, the additional therapeutic being selected from the group consisting of a chemotherapy drug, an AMPK activator, an alkylating agent, an antimetabolite, a plant alkaloid, a DNA targeting agent, radiation therapy, and combinations thereof. In one embodiment, the additional therapeutic is the AMPK activator. In one embodiment, the additional therapeutic is the AMPK activator and a chemotherapy drug. In some embodiments, the method further includes a pharmaceutical composition including the compound and a pharmaceutically-acceptable carrier.

In some embodiments, a method of treating cancer includes administering to a subject in need thereof an effective amount of a compound selected from the group consisting of a glycogen phosphorylase inhibitor, a glycogen synthase inhibitor, a glycogen degradation molecule, and combinations thereof; wherein the cancer is selected from the group consisting of non-small cell lung cancer, clear cell renal cancer carcinoma, Ewing's sarcoma, and glycogen rich clear cell carcinoma of the breast. In some embodiments, the method further includes administering an additional therapeutic to the subject, the additional therapeutic being selected from the group consisting of an AMPK activator and a chemotherapy drug. In some embodiments, the cancer is non-small cell lung cancer and the compound is the glycogen phosphorylase inhibitor 1,4-dideoxy-1,4-imino-D-Arabinitol (DAB). In some embodiments, the cancer is Ewing's sarcoma and the compound is the glycogen synthase inhibitor is 2-methoxyphenol (Guaiacol).

Further features and advantages of the presently-disclosed subject matter will become evident to those of ordinary skill in the art after a study of the description, figures, and non-limiting examples in this document.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

FIGS. 3A-3G: show a schematic and graphs illustrating analysis of glycolytic metabolites and histone acetylation in EV and malin-OE cell lines. (A) Tracer analysis of nuclear glycogen metabolism using $^{13}C$-glycogen produced from mice fed with $^{13}C$-glucose enriched liquid diet. (B)-(D) $^{13}C$-enriched free (B) glucose-6-phosphare (G6P), (C) 3-phosphoglycerate (3PG), and (D) pyruvate produced from $^{13}C$-glycogen. (E) $^{13}C$-enriched histone bound acetate after histone purification followed by acid hydrolysis. (F) In vitro analysis of total H4 histone acetylation after malin-OE using a sandwich ELISA. (G) In vitro analysis of total H3 histone acetylation after malin-OE using a sandwich ELISA. *0.01<P<0.05; 0.001<P<0.01; * P<0.001, two-tailed t-test.

FIGS. 10A-F show images illustrating identification and validation of malin interacting proteins. (A) Schematic of the domains of malin and the truncation constructs used to identify interacting proteins. Recombinant malin or malin truncations were incubated with HEK293 lysate to identify interacting proteins. Possible interacting partners were resolved using SDS-PAGE and stained by Coomassie. (B) Interacting partners with malin (full length), the six NHL repeats, or the NHL repeats and the linker region as identified by mass spectrometry. (C) Detection of malin interactions with glycogen phosphorylase brain isoform ($GP_{BB}$) by coimmunoprecipitation of tagged proteins expressed in HEK293 cells. (D-F) Detection of malin interactions with (D) HSP70, (E) glycogen branching enzyme (BE), and (F) glycogen debranching enzyme (GDE) by coimmunoprecipitation of tagged proteins expressed in HEK293 cells. Data in C-F are representative of three experiments.

FIGS. 29A-I show a schematic and graphs illustrating flux of metabolites through glycolysis and the Krebs cycle. (A) Tracing of glucose carbon through glycolysis and the Krebs cycle. Not all possible labeled metabolites are shown due to space limitations. O: $^{12}C$; *,*: $^{13}C$ from glycolysis, pyruvate dehydrogenase (PDH) and pyruvate carboxylase (PCB)-initiated reactions, respectively. Decreased flux through (B-D) glycolysis and (E-I) the Krebs cycle were observed after malin-OE. The x-axis denotes the [number] of 13C atoms present in each compound. Values shown are mean±SEM (average of 3 cell lines, n=3, independent experiment).

FIGS. 31A-E show graphs illustrating in vitro and in vivo efficacy of the glycogen synthase inhibitor guaiacol as an anti-ES agent. (A) A673 Ewing's sarcoma cells were treated with increasing concentrations of guaiacol. (B) The IC50 for guaiacol is ~20 µm in A673 cells. (C) Guaiacol resulted in a 3-fold reduction in normalized glycogen levels in treated xenograft tumors. (D) Combination treatment with guaiacol and metformin resulted in the highest p-ACC level. (E) A673 cells ($10^7$) were injected subcutaneously in athymic nude mice and when the tumor reached 0.1 cm$^3$ in size, a daily intraperitoneal injection was initiated of either PBS or guaiacol (20 mg/kg) and tumor size was measured over 15 weeks. Guaiacol significantly reduced the highly aggressive A673 xenograft growth with a 4-fold reduction in tumor volume at the experiment endpoint.

DESCRIPTION OF EXEMPLARY EMBODIMENTS

Figure 1A:
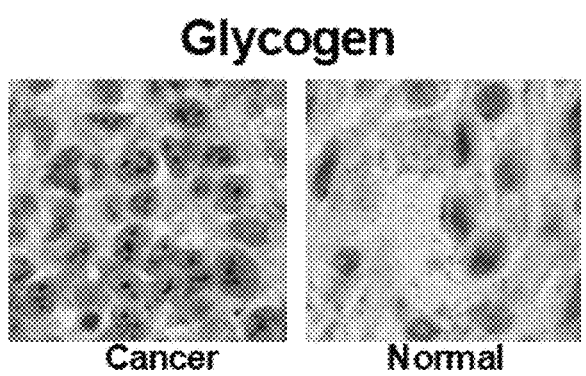
FIGS. 1A-F show images and graphs illustrating glycogen and malin content in normal and non-small cell lung cancer (NSCLC) cells. (A) Immuno-histochemical staining using a highly specific glycogen antibody of paired non-small cell lung cancer (NSCLC) tumor and benign lung tissue (normal) resected at surgery. (B) Immuno-histochemical analysis of 3,3'-Diaminobenzidine (DAB) staining using the HALO digital pathology software showing % of glycogen containing nuclei in NSCLC patient tumor and normal samples (n=20). (C) Biochemical quantitation of nuclear glycogen in NSCLC patient tumor and normal samples (n=20). (D) Immuno-histochemical staining of malin in paired NSCLC tumor and normal tissue resected at surgery. (E) Malin protein expression in patient tumor and normal samples (n=20), defined by average DAB intensity. (F) Kaplan-Meier survival plot of NSCLC patient data from TCGA with high and low malin expression separated by upper and lower quartile. Blue, low malin mRNA; red, high malin mRNA. *0.01<P<0.05;  0.001<P<0.01; * P<0.001, two-tailed t-test.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter. Unless defined otherwise, all technical and scientific terms used herein have the same meaning as is commonly understood by one of skill in the art to which the invention(s) belong. All patents, patent applications, published applications and publications, GenBank sequences, databases, websites and other published materials referred to throughout the entire disclosure herein, unless noted otherwise, are incorporated by reference in their entirety. Where reference is made to a URL or other such identifier or address, it understood that such identifiers can change and particular information on the internet can come and go, but equivalent information can be found by searching the internet. Reference thereto evidences the availability and public dissemination of such information.

Although any methods, devices, and materials similar or equivalent to those described herein can be used in the practice or testing of the presently-disclosed subject matter, representative methods, devices, and materials are described herein.

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

As used herein, the term "about," when referring to a value or to an amount of mass, weight, time, volume, concentration or percentage is meant to encompass variations of in some embodiments ±10%, in some embodiments ±5%, in some embodiments ±1%, in some embodiments ±0.5%, in some embodiments ±0.1%, and in some embodiments ±0.01% from the specified amount, as such variations are appropriate to perform the disclosed method.

The terms "about," "up to," "generally," and the like are to be construed as modifying a term or value such that it is not an absolute. Such terms will be defined by the circumstances and the terms that they modify as those terms are understood by those of skill in the art. This includes, at very least, the degree of expected experimental error, technical error and instrumental error for a given experiment, technique or an instrument used to measure a value. The term "about" is used to provide flexibility to a numerical range endpoint by providing that a given value may be "a little above" or "a little below" the endpoint. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

As used herein, the terms "treatment" or "treating" refer to the medical management of a subject with the intent to cure, ameliorate, reduce, or prevent or slow progression of a cancer. As will be recognized by one of ordinary skill in the art, the term "cure" does not refer to the ability to completely remove any and all trace of a cancer in all cases.

As used herein, the terms "subject" or "subject in need thereof" refer to a target of administration, which optionally displays symptoms related to a particular disease, pathological condition, disorder, or the like. The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered.

As used herein, the term "administering" refers to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition. In some embodiments, oral administration is used. In some embodiments, intravenous (IV) administration is used.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition. In some embodiments, about 50 mg/kg is administered as often as once daily.

The presently-disclosed subject matter includes a method of treating a cancer with elevated glycogen. In some embodiments, elevated glycogen includes glycogen content that is increased at least 2, at least 3, at least 4, at least 5, at least 10, at least 50, from 1-100, from 10 and 100 times higher than normal tissue glycogen, or any combination, sub-combination, range, or sub-range thereof. Examples of cancers with elevated glycogen include, but are not limited to, non-small cell lung cancer, clear cell renal cancer carcinoma, Ewing sarcoma, and glycogen rich clear cell carcinoma of the breast. In these and other cancers involving elevated glycogen, the glycogen can modulate cellular metabolism through the master regulator AMPK. More specifically, as supported by the data included herewith, the present inventors have discovered that such glycogen binds to AMPK with high affinity and abolishes its activity. Subsequently, this decreased AMPK activity drives aberrant metabolism and tumor proliferation in cancers having elevated glycogen. These findings have broad implications for the prevention and personalized treatment of other glycogen storage diseases and metabolic diseases including many forms of cancer. Therefore, disruption of this process is a therapeutic option for these cancers.

In some embodiments, the method includes administering an effective amount of a glycogen phosphorylase inhibitor, a glycogen synthase inhibitor, an anti-sense oligonucleotide to down-regulate glycogen synthesis, a glycogen degradation molecule, or a combination thereof to a subject in need thereof. Certain glycogen phosphorylase inhibitors, glycogen synthase inhibitors, anti-sense oligonucleotides to down-regulate glycogen synthesis, or glycogen degradation molecules are known in the art. For example, in some embodiments the glycogen phosphorylase inhibitor can be 1,4-dideoxy-1,4-imino-D-Arabinitol (DAB), 1-(3-(3-(2-Chloro-4,5-difluorobenzoyl)ureido)-4-methoxyphenyl)-3-methylurea, also known as Glycogen Phosphorylase Inhibitor (GPI), 5-Chloro-N-[(1S,2R)-3-(dimethylamino)-2-hydroxy-3-oxo-1-(phenylmethyl)propyl]-1H-indole-2-carboxamide (CP-91149), or 5-Chloro-N-[(1S,2R)-2-hydroxy-3-(methoxymethylamino)-3-oxo-1-(phenylmethyl)propyl]-1H-indole-2-carboxamide (CP-316819). In some embodiments, the glycogen synthase inhibitor can be 2-methoxyphenol (Guaiacol). In some embodiments, the glycogen degradation molecule can be the fusion protein VAL-0417 (Valerion) or the antibody-enzyme fusion VAL-1221 (Valerion).

In some embodiments, the method also includes administration of another therapeutic. For example, in some embodiments, in addition to the glycogen phosphorylase inhibitor, glycogen synthase inhibitor, anti-sense oligonucleotide to down-regulate glycogen synthesis, or glycogen degradation molecule, the subject can also receive a chemotherapy drug or an AMPK activator. Additionally or alternatively, in some embodiments, the subject can also receive an alkylating agent, an antimetabolite, a plant alkaloid, a DNA targeting agent, or radiation therapy.

The presently-disclosed subject matter also includes pharmaceutical compositions comprising a glycogen phosphorylase inhibitor, a glycogen synthase inhibitor, or a glycogen degradation molecule. In some embodiments, the methods disclosed herein involve administering an effective amount of a pharmaceutical composition comprising a glycogen phosphorylase inhibitor, a glycogen synthase inhibitor, or a glycogen degradation molecule. In some embodiments, the method for treating cancer involves administering an effective amount of a pharmaceutical composition comprising a glycogen phosphorylase inhibitor, a glycogen synthase inhibitor, or a glycogen degradation molecule to a subject in need of treatment for cancer. In some embodiments, the method also involves a step of identifying the subject has having a need for cancer treatment.

Pharmaceutical compositions, as disclosed herein, include a glycogen phosphorylase inhibitor, a glycogen synthase inhibitor, or a glycogen degradation molecule and further include a pharmaceutically-acceptable carrier. In this regard, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

The compositions can take such forms as suspensions, solutions or emulsions in oily or aqueous vehicles, and can contain formulatory agents such as suspending, stabilizing and/or dispersing agents. Suitable formulations include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents. Alternatively, the active ingredient can be in powder form for constitution with a suitable vehicle, e.g., sterile pyrogen-free water, before use.

The formulations can be presented in unit-dose or multi-dose containers, for example sealed ampoules and vials, and can be stored in a frozen or freeze-dried (lyophilized) condition requiring only the addition of sterile liquid carrier immediately prior to use.

For oral administration, the compositions can take the form of, for example, tablets or capsules prepared by a conventional technique with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets can be coated by methods known in the art.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration the compositions can take the form of tablets or lozenges formulated in conventional manner.

The compounds can also be formulated as a preparation for implantation or injection. Thus, for example, the compound can be formulated with suitable polymeric or hydrophobic materials (e.g., as an emulsion in an acceptable oil) or ion exchange resins, or as sparingly soluble derivatives (e.g., as a sparingly soluble salt).

The compound can also be formulated in rectal compositions (e.g., suppositories or retention enemas containing conventional suppository bases such as cocoa butter or other glycerides), creams or lotions, or transdermal patches.

The presently-disclosed subject matter is further illustrated by the following specific but non-limiting examples. The following examples may include compilations of data that are representative of data gathered at various times during the course of development and experimentation related to the present invention.

EXAMPLES

Example 1

The studies described in this Example address the half-century old phenomenon of nuclear glycogen in the case of non-small cell lung cancer (NSCLC). Glycogen accumulation was found in the nucleus of NSCLC patient tumors and model cell lines and its pivotal role in modulating histone acetylation was defined. More specifically, a key function for nuclear glycogen in epigenetic regulation has been demonstrated through compartmentalized pyruvate production and histone acetylation. This pathway is altered in human NSCLC, as surgical specimens accumulate glycogen in the nucleus. In particular, a decreased abundance of malin, an E3 ubiquitin ligase, impaired nuclear glycogenolysis by preventing the nuclear translocation of glycogen phosphorylase and causing nuclear glycogen accumulation. Reintroduction of malin in lung cancer cells restored nuclear glycogenolysis, increased histone acetylation, and decreased growth of cancer cells transplanted into mice. That is, a previously unknown role for glycogen metabolism in the nucleus has been discovered and another mechanism by which cellular metabolites control epigenetic regulation has been elucidated. In view thereof, and based upon data from pre-clinical models, it is believed that glycogen is a therapeutic target for cancers with high levels of glycogen.

Figure 1B:
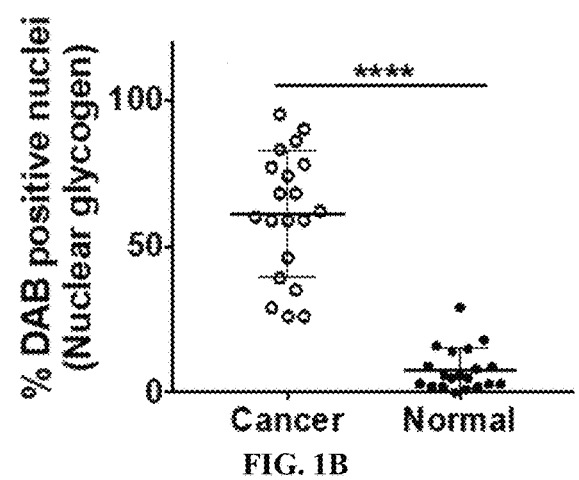
Figure 1C:
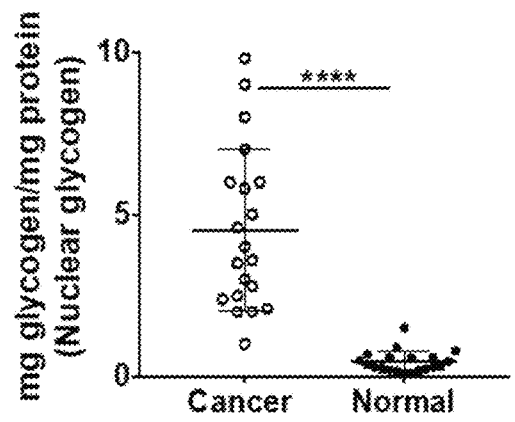
Figure 5A:
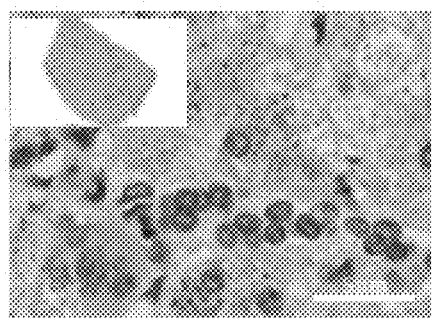
FIGS. 5A-C show images illustrating quantitation of glycogen IHC staining. (A) IHC staining of glycogen distribution in healthy human liver using a glycogen antibody. Inset shows a lower magnification view. Brown puncta are observed in the cytoplasm. (B) IHC staining of glycogen in NSCLC tissue with 4× zoom. Inset shows a lower magnification view. (C) Application of the multiplex histochemical module in the HALO image analysis software outlining the nuclei and whole cell in NSCLC tissue.
Figure 5B:
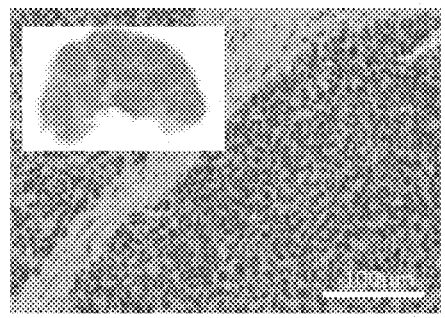
Figure 5C:
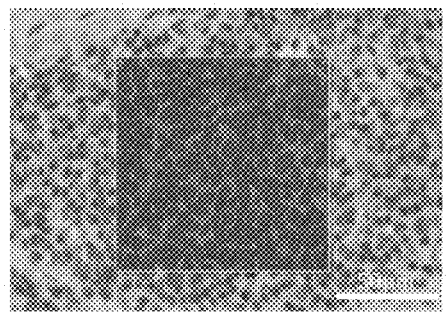
Figure 6:
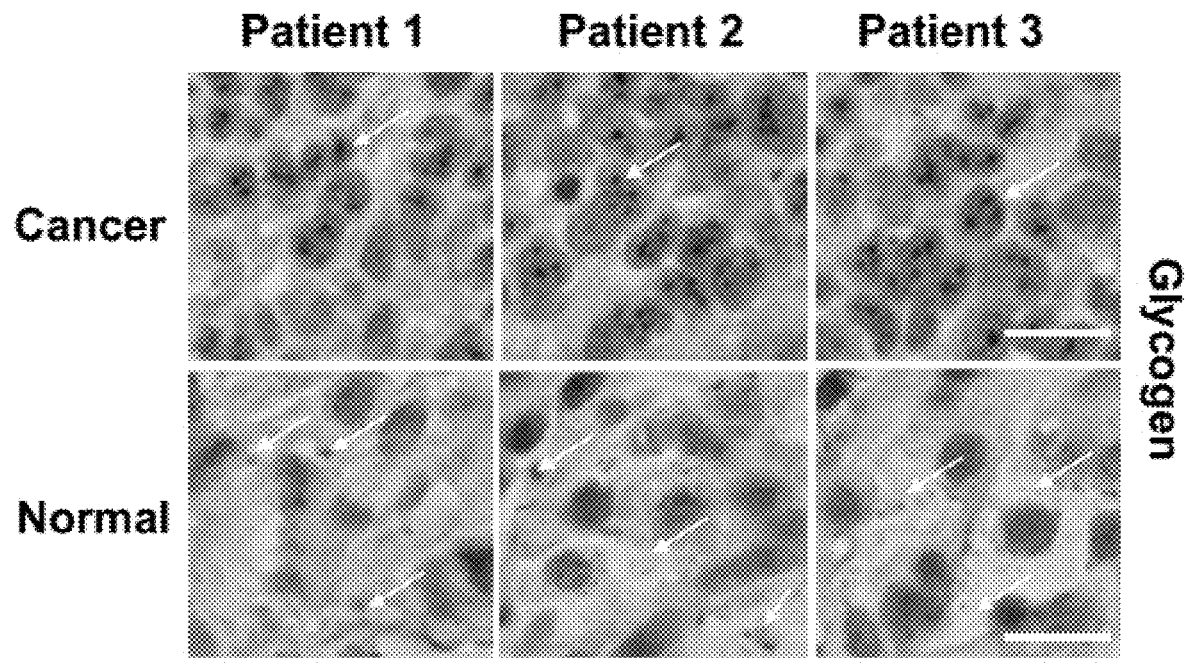
FIG. 6 shows images illustrating representative nuclear glycogen staining in three NSCLC patients. IHC staining of glycogen in three patients showing nuclear glycogen accumulation in cancerous tissues versus cytoplasmic localization in the paired normal tissues. White arrows indicate glycogen deposits. Scale bars=5 µm.

Immunohistochemical (IHC) imaging of paired NSCLC and tumor-distal benign lung tissues (n=20 each), using a highly specific anti-glycogen antibody (FIG. 5A), revealed distinct punctate glycogen staining in the nuclei of cancer cells (FIGS. 1A, 5B, and 6). Detailed distribution analyses using the HALO digital pathology software (FIG. 5C) show a greater than 50-fold increase in the number of glycogen positive nuclei in cancer cells compared to normal (FIG. 1B). Nuclear glycogen was also biochemically quantitated in isolated nuclei using cellular fractionation. As with IHC analysis, cancer tissues displayed significantly elevated nuclear glycogen compared to normal tissues (FIG. 1C). Nuclear glycogen content ranged from 1-10 mg/mg protein in patient cancer tissues, representing a 10-100-fold increase compared with normal tissue.

Figure 7A:
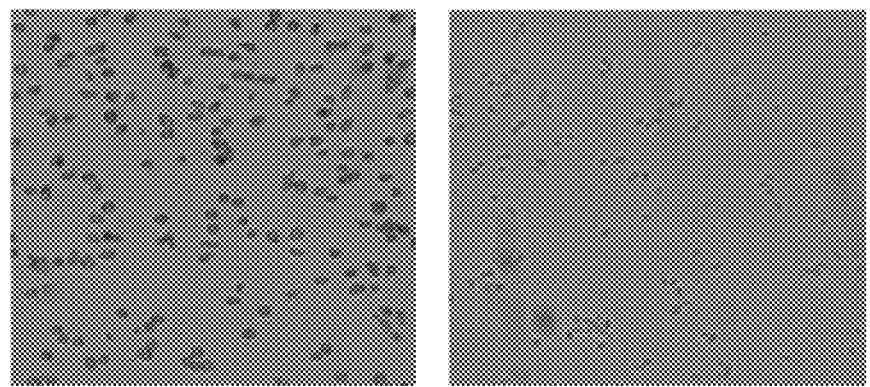
FIGS. 7A-C show images and graphs illustrating high-purity nuclei isolation. (A) Bright field images of whole A549 cells (left) and isolated nuclei (right) imaged by the Bio-Rad TC20 cell counter. (B) Cell size distribution in whole cell population (left) and isolated nuclei (right) as quantified by the Bio-Rad TC20 cell counter. (C) Immuno-blotting analysis of nuclear and non-nuclear fractions from A549 cells, using the transcription factor USF1 and histone as nuclear markers, succinate dehydrogenase (SDH) as a mitochondrial marker, and actin as cytoplasmic marker. All data are representative of three experiments.
Figure 7B:
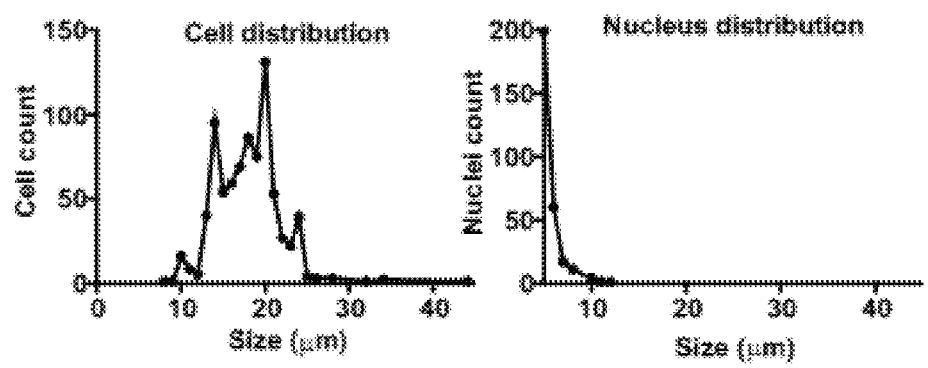
Figure 7C:
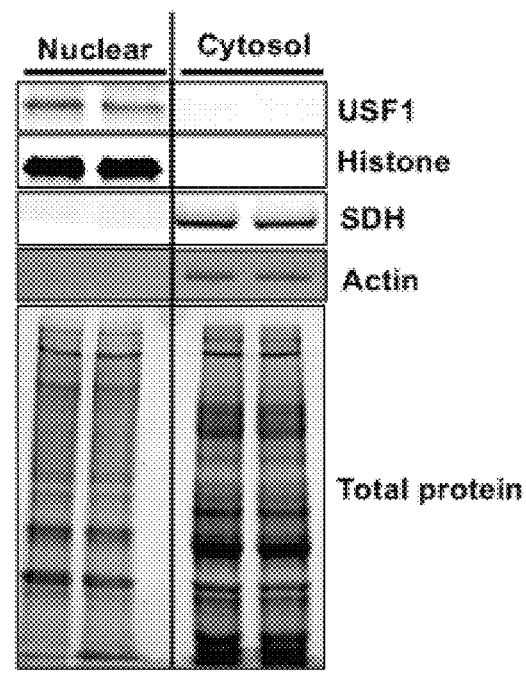
Figure 8A:
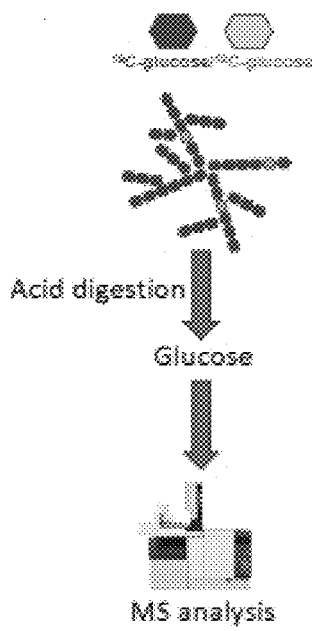
FIGS. 8A-E show images and graphs illustrating that glucose-6-phosphate is required for nuclear glycogen synthesis. (A) Schematic of glycogen enrichment analysis. (B) Glycogen synthesis assay with purified intact nuclei from A549, H1299, and H2030 cells using $^{13}C_6$-glucose-6-phosphate and $^{13}C_6$-glucose as substrates for nuclear glycogen synthesis. (C) Nuclear glycogen synthesis with $^{13}C_6$-glucose-6-phosphate reached isotopic steady state at 6 hours. (D) Diagram depicting nuclear glycogen synthesis preferentially from $^{13}C_6$-glucose-6-phosphate. (E) Detection of proteins in the nuclear and nonnuclear fractions of A549 cells. Glycogen synthase (GYS); UDP-glucose pyrophosphorylase (UGP); hexokinase (HK); glucose transporters (Glut1 and Glut 4). Data in B and C are from three experiments and are shown as mean±SE. Data in E are representative of three experiments. *0.01<P<0.05;  0.001<P<0.01; * P<0.001, two-tailed t-test.
Figure 8B:
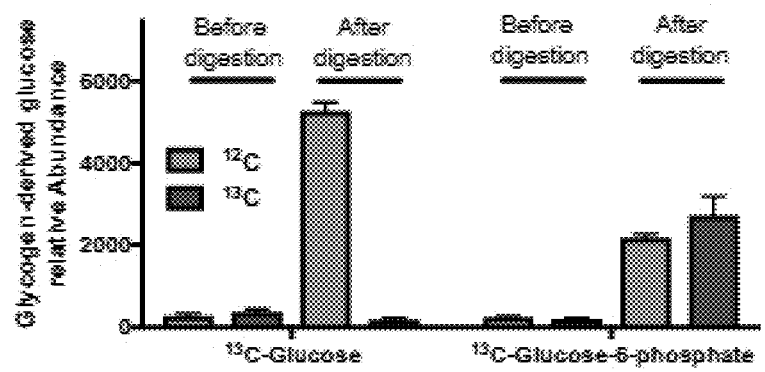
Figure 8C:
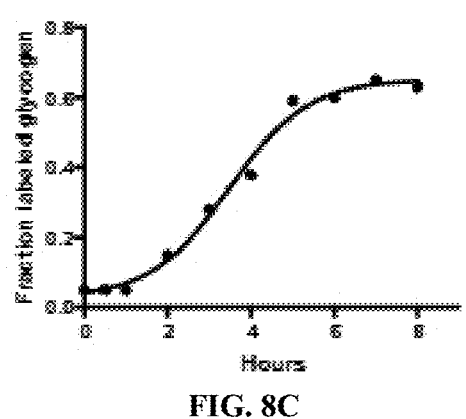
Figure 8D:
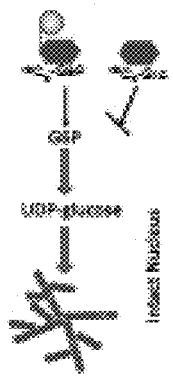
Figure 8E:
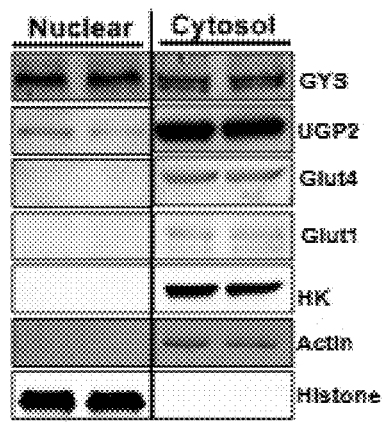

The molecular weight of glycogen is 5-20 million Daltons, and currently there is no known transporter capable of transporting it. Early reports in the 1980s demonstrated glycogen synthase (GYS) activity in the nucleus and suggested nuclear de novo glycogen synthesis. Immunoblotting analysis demonstrated the presence of both GYS and UDP-glucose pyrophosphorylase (UGP) in nuclear extracts (FIG. 7C). To confirm that these enzymes were functionally active in the nucleus, lung cancer cells were treated with isotonic buffer to lyse the cell membrane followed by sucrose gradient purification to achieve high-purity and intact nuclei (FIGS. 7A-B). To verify that glycogen is de novo synthesized in the nucleus, nuclei were incubated with either $^{13}C_6$-glucose or $^{13}C_6$-glucose-6-phoshate in respiration buffer, followed by mass spectrometry analysis of digested glycogen (FIGS. 8A-E). Surprisingly, glucose could not be used as a substrate for nuclear glycogen synthesis, and instead glucose-6-phoshate was the preferred substrate (FIG. 8B). These findings are supported by the immunoblotting analysis that failed to detect glucose transporters and hexokinase in the nuclear fractions (FIG. 7C).

Figure 1D:
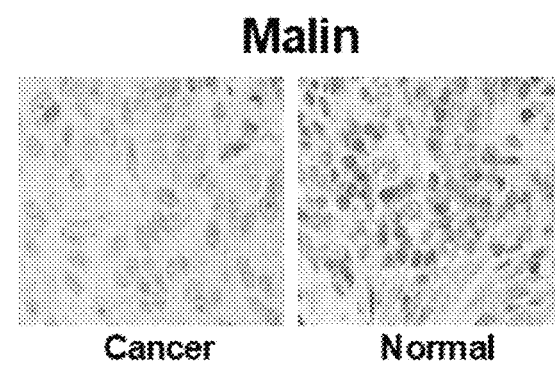
Figure 1E:
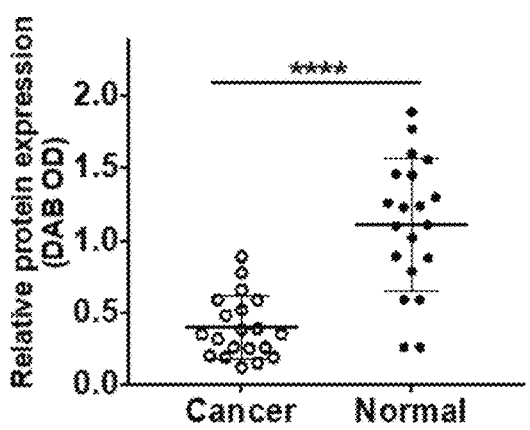
Figure 1F:
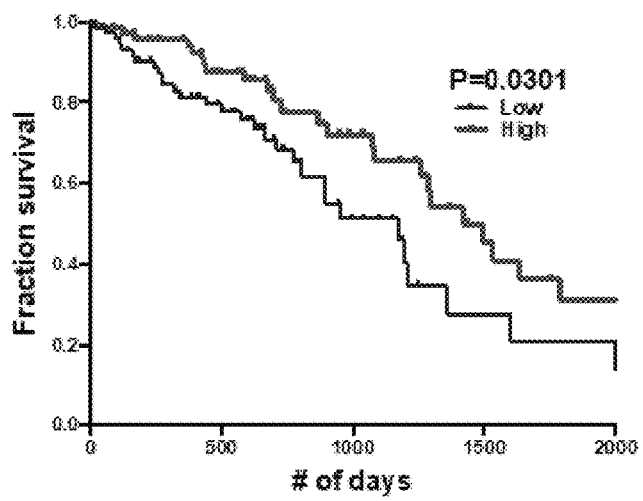
Figure 9A:
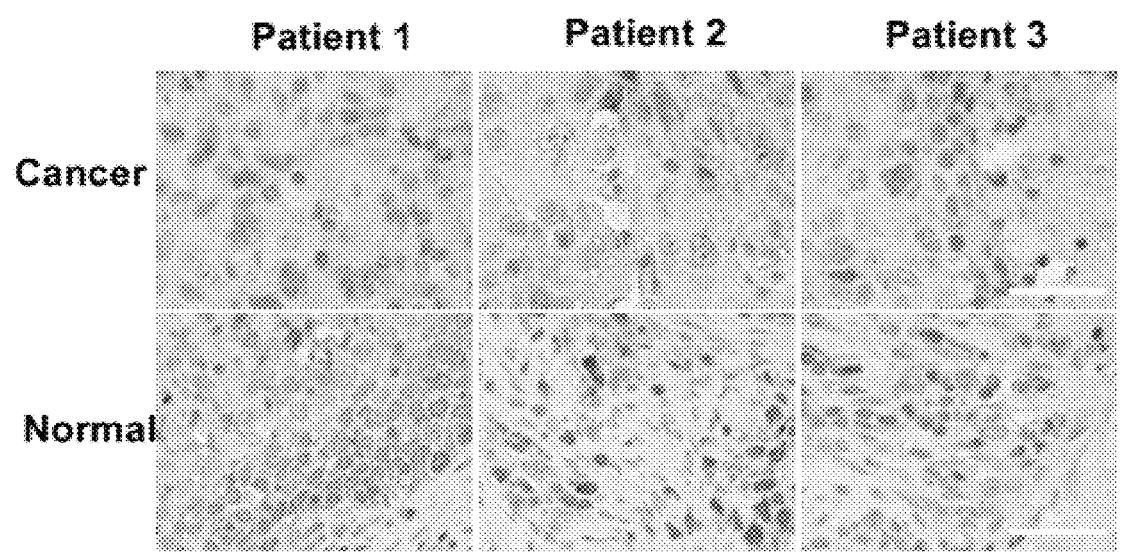
FIGS. 9A-B show images illustrating that malin abundance is reduced in NSCLC patient specimens. (A) IHC staining of malin in three paired patient NSCLC and normal tissues. (B) Immunoblotting of malin in four representative paired NSCLC and normal tissues. Tubulin (Tub) is used as a loading control. Scale bars=5 μm.
Figure 9B:
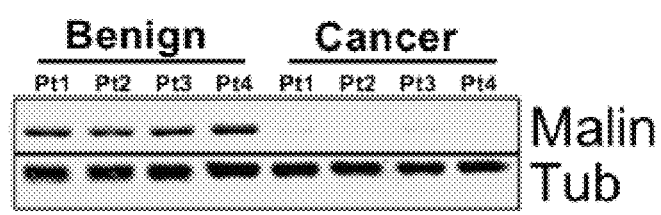

Nuclear glycogen accumulation was accompanied by the suppression of malin, an E3 ubiquitin ligase reported to interact with glycogen metabolic enzymes (FIGS. 1D and 9A). A dramatic decrease in malin protein levels in NSCLC patient samples was observed by both histochemical staining (FIG. 1E) and immunoblotting (FIG. 9B), when compared to benign lung tissues. Using TCGA survival data with matching RNAseq analysis, high malin mRNA expression was found to correlate with better survival, suggesting malin is of clinical importance in NSCLC (FIG. 1F, p=0.0301). Strikingly, this correlation was specific to lung cancer, since it was not observed in breast, prostate, or ovarian cancers (data not shown).

Figure 11A:
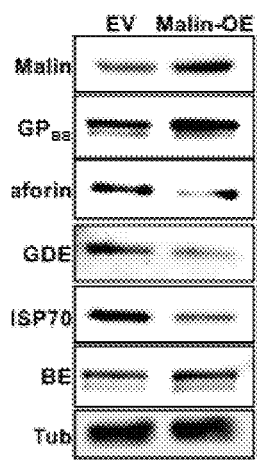
FIGS. 11A-E show images illustrating that malin ubiquitination of $GP_{BB}$ drives nuclear localization. (A) Immunoblotting analysis of HSP70, laforin, glycogen debranching enzyme (GDE), branching enzyme (BE), and glycogen phosphorylase (GP) with anti-tubulin (Tub) as the loading control in empty vector (EV) or malin-overexpressing (malin-OE) HEK293 cells. (B) Localization of exogenously expressed malin and GP in HEK293 cells assessed by immunofluorescence. (C) In vitro ubiquitination assay using recombinant E1, E2 (UbcH5a), malin, and myc-GP followed by immunoprecipitation with anti-myc, SDS-PAGE, and immunoblotting analysis with an antibody detecting ubiquitin. (D) Effect of inhibition of nuclear import with leptomycin on GP localization. HEK293 cells were transfected with GFP-MEK or empty vector for the analysis of endogenous GP. Twenty-four hours post-transfection, cells were exposed to leptomycin B for 3 hours, and protein localization was assessed by immunofluorescence. (E) Schematic model for GP nuclear translocation after malin-mediated ubiquitination. All data are representative of three experiments.

Ubiquitination can impact protein levels by promoting proteasome-dependent degradation, changing enzymatic activity, and/or changing protein localization. Therefore, it was contemplated that downregulation of malin contributes to nuclear glycogen accumulation by impacting one or more glycogen metabolic enzymes via at least one of these mechanisms. Malin is comprised of a RING domain, a linker region, and six NHL protein-protein interaction repeats (FIG. 10A). To identify novel malin substrates that could modulate nuclear glycogen, recombinant malin was purified, the protein was incubated with cell extract of HEK293T cells, and malin-bound proteins were identified by mass spectrometry. Known interacting proteins were identified, including the glycogen phosphatase laforin, glycogen debranching enzyme (GDE), and HSP70, as were several novel putative malin-interacting partners, including glycogen branching enzyme (GBE) and glycogen phosphorylase brain isoform ($GP_{BB}$) (FIG. 10B). Using co-expression and co-immunoprecipitation experiments, the known interactions and the malin interaction with $GP_{BB}$ (FIGS. 10C-F) were validated. $GP_{BB}$, despite its name, is highly expressed in most tissues. Furthermore, malin over-expression (OE) resulted in decreased levels of laforin, HSP70, and GDE in the model cell line (FIG. 11A), validating previous reports.

Figure 2A:
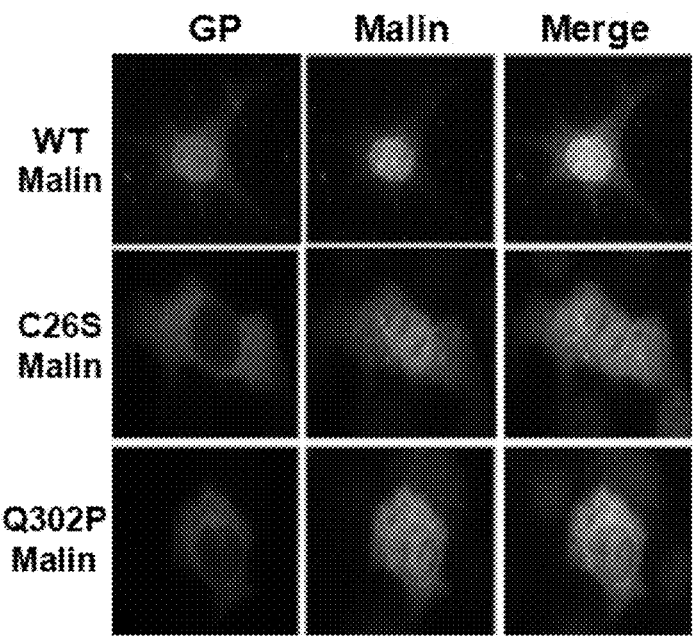
FIGS. 2A-G show images illustrating that Malin promotes nuclear localization of GP. (A) GP was co-expressed with either malin wildtype (WT) or malin mutants, C26S or Q302P, in HEK293 cells and protein localization was assessed by immunofluorescence. (B-D) Immunoblotting analysis of malin-OE promoting nuclear localization of $GP_{BB}$ in (B) A549, (C) H2030, and (D) H1299. (E-G) Biochemical quantitation of nuclear glycogen in (E) A549, (F) H1299, and (G) H2030 EV and malin-OE cell lines. *0.01<P<0.05;  0.001<P<0.01; * P<0.001, two-tailed t-test.
Figure 11B:
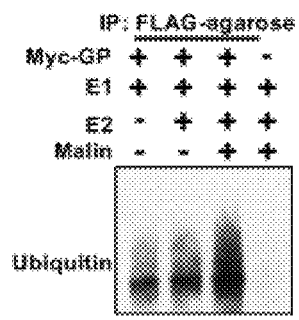
Figure 11C:
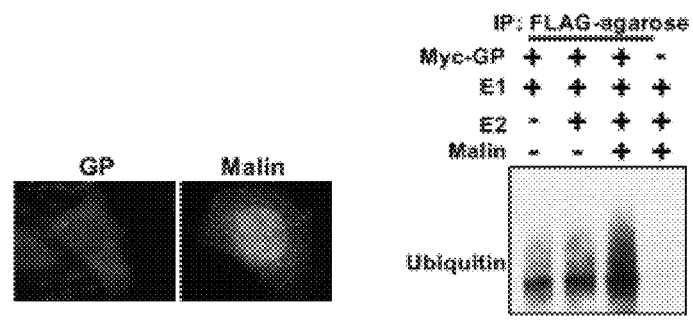
Figure 11D:
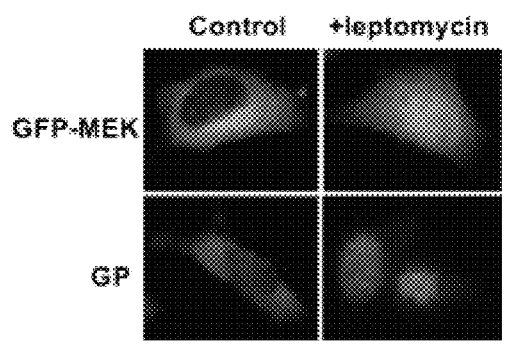
Figure 11E:
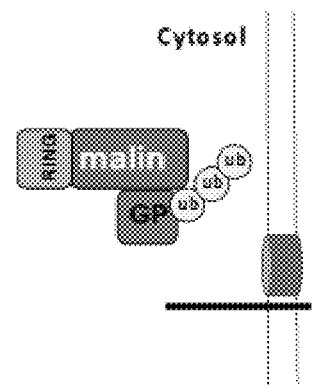

Since $GP_{BB}$ is a novel malin-interacting protein, malin-dependent regulation of its localization was of interest. $GP_{BB}$ is largely localized to the cytoplasm (FIG. 11B). The incubation of recombinant malin with ubiquitin-activating enzyme (E1), ubiquitin-conjugating enzyme (E2), ATP, and ubiquitin resulted in increased GP ubiquitination in vitro (FIG. 11C). Co-expression with malin resulted in $GP_{BB}$ translocation from the cytoplasm to the nucleus rather than proteasomal-directed degradation (FIGS. 2A and 11E). Conversely, co-expression of a malin point mutation in either the malin RING or NHL domains abolished the $GP_{BB}$ nuclear localization (FIG. 2A). Moreover, treatment with leptomycin, a nuclear exportin inhibitor, resulted in the accumulation of endogenous GP in the nucleus, suggesting $GP_{BB}$ translocation is part of normal cellular physiology (FIG. 11D).

Figures 2B, 2C:
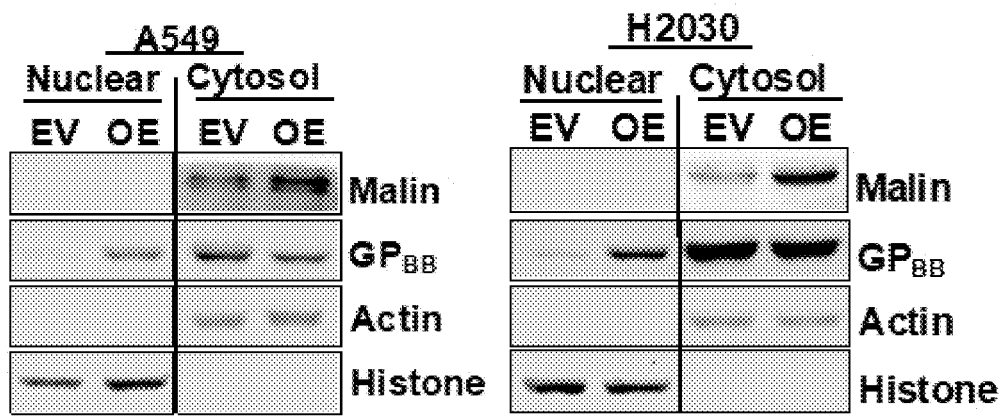
Figure 2D:
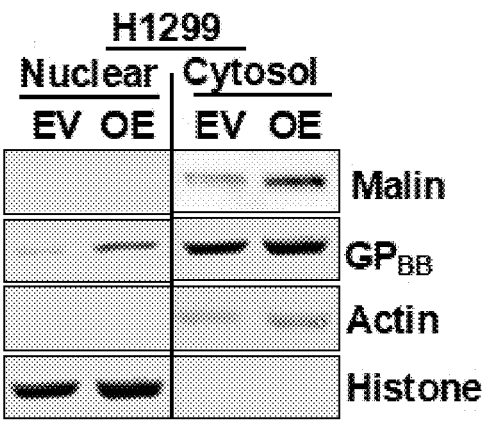
Figure 2E:
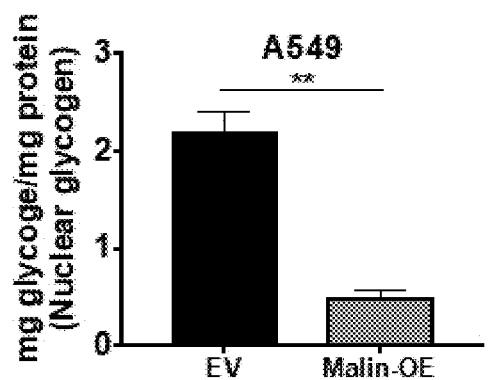
Figure 2F:
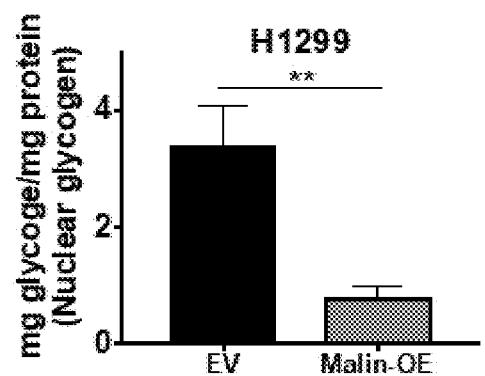
Figure 2G:
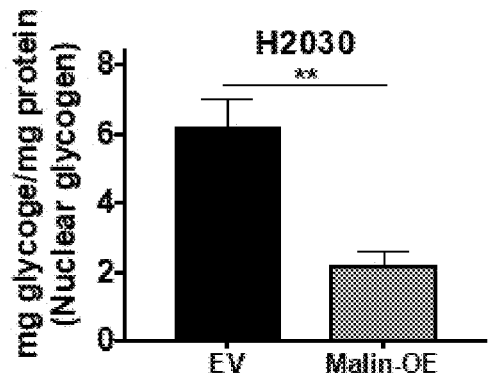
Figure 12A:
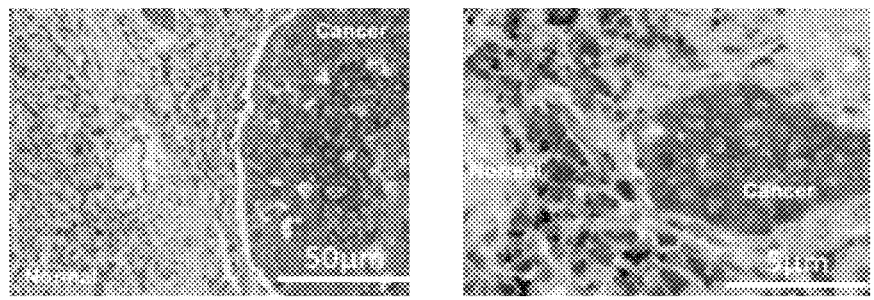
FIGS. 12A-D show images and graphs illustrating increased cytoplasmic accumulation of $GP_{BB}$ in NSCLC patient specimens. (A) IHC staining of $GP_{BB}$ in NSCLC tissue and surrounding stroma cells. (B) Relative mRNA abundance for $GP_{BB}$ between lung adenocarcinoma (LUAD) and lung squamous cell carcinoma (LUSC) from TCGA database. Red=cancer; grey=Normal. (C) Quantification of IHC analysis of $GP_{BB}$ abundance in NSCLC patient tumor and normal samples (n=20). (D) Quantification of the percent of $GP_{BB}$-containing nuclei in NSCLC patient tumor and normal samples (n=20), quantified from IHC data. *$0.01<P<0.05$;  $0.001<P<0.01$; * $P<0.001$, two-tailed t-test.
Figure 12B:
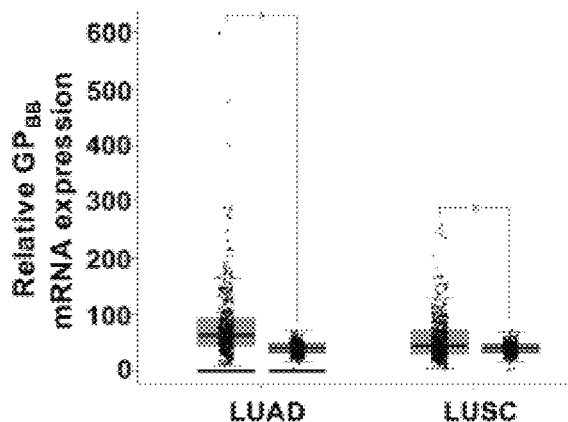
Figure 12C:
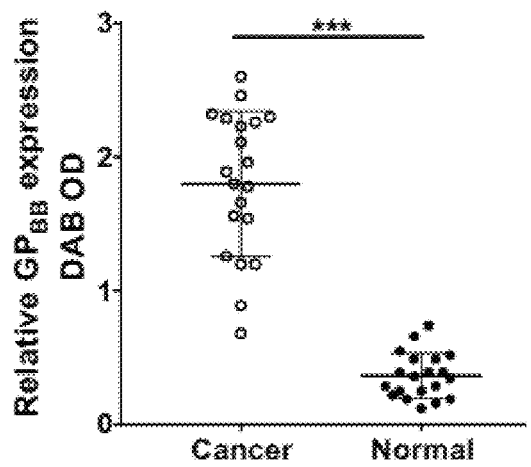
Figure 12D:
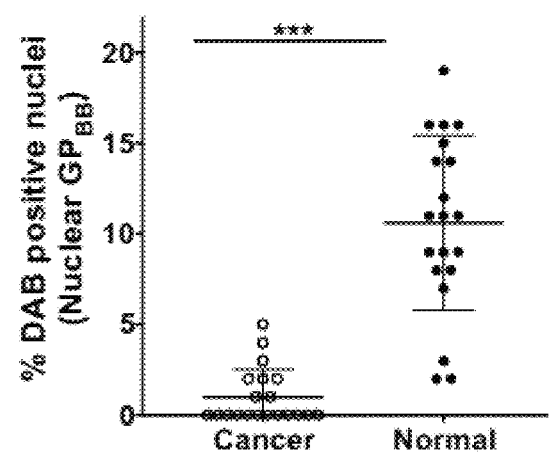

To validate the malin and GP$_{BB}$ interaction in NSCLC cells, malin was over-expressed in three different lung cancer cell lines, and assessed GP$_{BB}$ localization. In all three cases malin-OE resulted in increased nuclear GP (FIGS. 2B-D). Furthermore, up to a 70% decrease in nuclear glycogen in malin-OE cell lines was observed, suggesting that the lack of nuclear GP$_{BB}$ is the cause of nuclear glycogen accumulation in NSCLC tissue (FIGS. 2E-G). To determine if nuclear GP$_{BB}$ accumulation occurs in vivo in human patient specimens, GP$_{BB}$ mRNA and protein levels were examined using the TCGA database and immunohistochemical staining of patient samples. GP$_{BB}$ mRNA and protein were significantly elevated in the cancer tissue compared to normal (FIGS. 12A-C). Additionally, GP$_{BB}$ expression was cytosolic in cancerous tissues, while 10%-20% of GP$_{BB}$ was localized to the nucleus in the normal tissue (FIG. 12D).

Figure 13A:
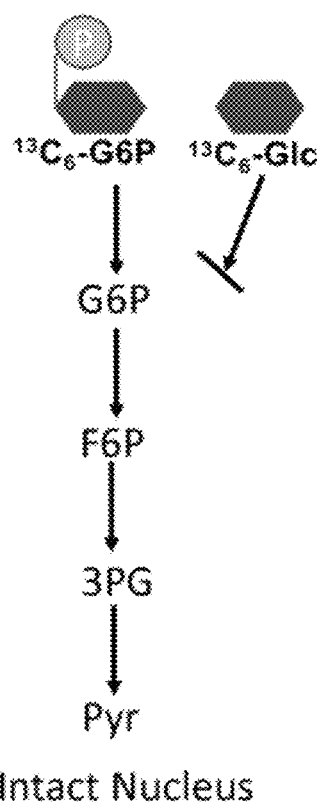
FIGS. 13A-C show images and graphs illustrating that isolated nuclei perform glycolysis independently of cytoplasm. (A) Diagram representing nuclear glycolysis starting with glucose-6-phosphate. (B) Immunoblot analysis of a panel of glycolytic enzymes in isolated nuclei. Data are representative of three experiments. (C) Fraction enrichment of glycolytic substrates in purified nuclei labeled with either $^{13}C_6$-glucose or $^{13}C_6$-glucose-6-phosphate. All data are representative of three experiments and are presented as mean±SE. *$0.01<P<0.05$;  $0.001<P<0.01$; *$P<0.001$, two-tailed t-test.
Figure 13B:
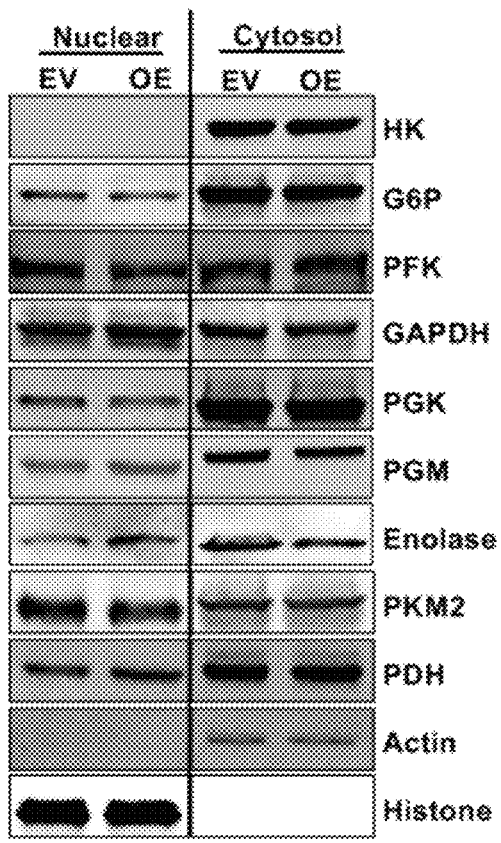
Figure 13C:
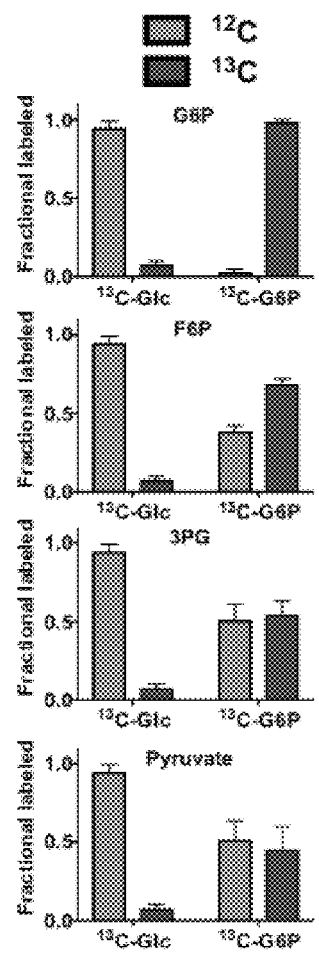

The present inventors contemplated that the existence of nuclear glycogen could be a separate carbon pool from the cytosolic fraction, supplying metabolic substrates for histone modification without mobilizing cytosolic metabolites. Glycolytic enzymes have been shown to moonlight in the nucleus, with many having undefined functions. Moreover, pyruvate dehydrogenase has been reported to translocate to the nucleus and regulate histone acetylation, but the origin of nuclear pyruvate remains ambiguous. Therefore, the functional role of nuclear glycogen and GP in pyruvate production and histone acetylation were investigated using isolated nuclei and stable isotope technology. First, it was tested whether glycolytic enzymes can carry out glycolysis independent of the cytosolic fraction (FIG. 13A). With the exception of hexokinase, every enzyme in the glycolytic pathway was in the nucleus (FIG. 13B). Using stable isotope tracers, isolated nuclei were found to successfully breakdown glucose-6-phosphate (G6P) to glycolytic intermediates including, fructose-6-phosphate, 3-phosphoglycerate (3PG), and pyruvate; however, glucose cannot be utilized (FIG. 13C).

Figure 14A:
FIGS. 14A-B show a schematic and a graph illustrating production and isolation of $^{13}C$-glycogen in mouse liver. (A) Schematic depicting the liquid diet using $^{13}C_6$-glucose fed to mice to enrich for $^{13}C$-glycogen in the liver. The liver served as a source of labeled glycogen for subsequent experiments. (B) $^{13}C$-glycogen enrichment in the liver reached steady state after 24-hours of ingestion of $^{13}C$-glucose liquid diet. Data are representative of mean±SE from five separate animals.
Figure 14B:
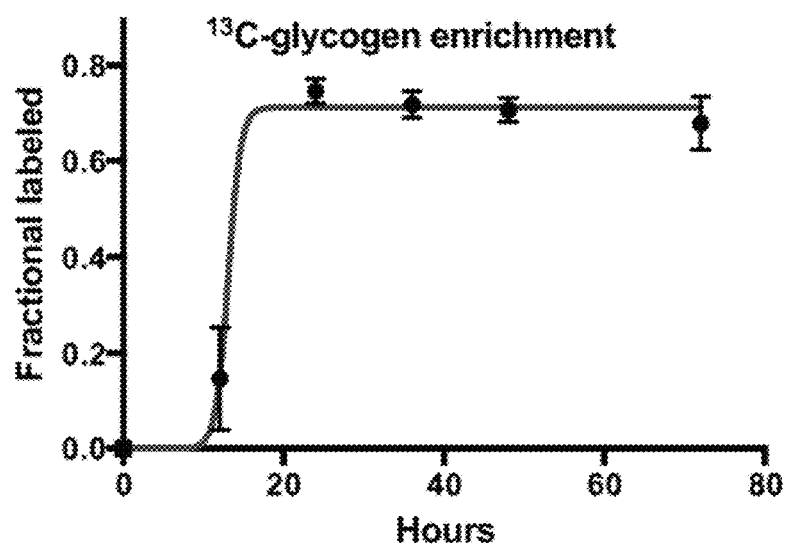

To define the metabolic fate of nuclear glycogen, $^{13}$C-glycogen was generated using a liquid diet stable tracer enrichment method recently described. 8-week old mice were fed a $^{13}$C$_6$-glucose enriched liquid diet for 48 hours (FIG. 14A) and liver glycogen was purified by trichloroacetic acid extraction and ethanol precipitation. Maximum $^{13}$C$_6$-glucose incorporation occurred after 24-hours (FIG. 14B). Next, the nuclei from empty vector (EV) or malin-OE cells were isolated in hypotonic cell lysis buffer. A nuclear hypotonic lysis buffer was then used to release nuclear enzymes while preserving enzyme integrity. Nuclear lysates were incubated with $^{13}$C-glycogen in respiration buffer for 6 hours and polar metabolites and their isotopologues were derivatized and analyzed by gas-chromatography mass spectrometry (FIG. 3A). Malin-OE and nuclear localization of GP resulted in the successful breakdown of glycogen and the enrichment of glycolytic metabolites such as G6P, 3PG, and pyruvate (FIGS. 3B-D). Strikingly, histone-bound $^{13}$C-acetate was markedly increased with malin expression (FIG. 3E) suggesting a direct role for nuclear glycogen in supplying substrate for histone acetylation.

Figure 15A:
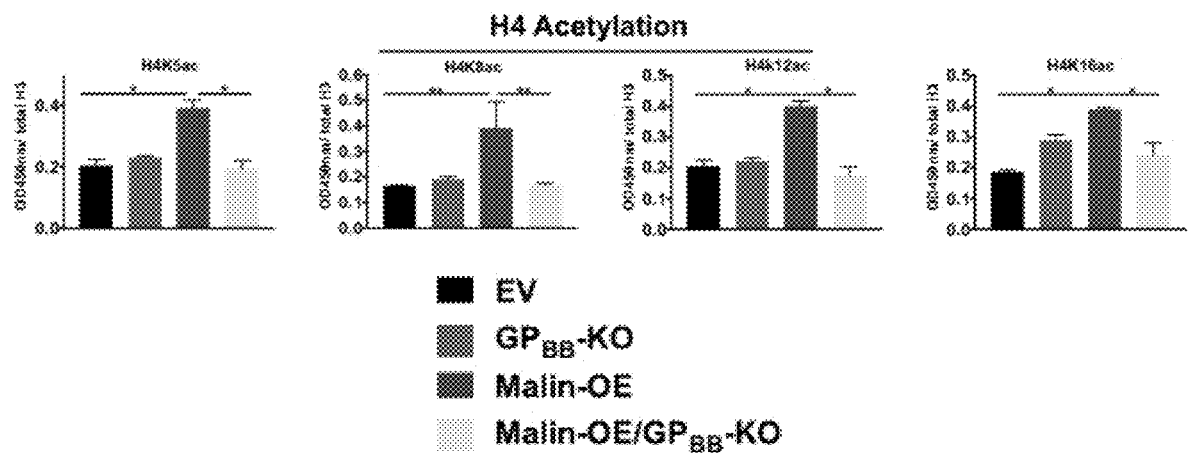
FIGS. 15A-C show graphs illustrating increased H3 and H4 acetylation in cell lines with malin-OE. (A) Panel of acetylated H4 lysine residues measured by ELISA. (B) Panel of acetylated H3 lysine residues measured by ELISA. (C) Scatter plot of the transcriptomes of the indicated cells expressing the empty vector (EV) or malin (malin-OE). Data in A and B are from three experiments and are presented as mean±SE. *$0.01<P<0.05$; **$0.001<P<0.01$, two-tailed t-test.
Figure 15B:
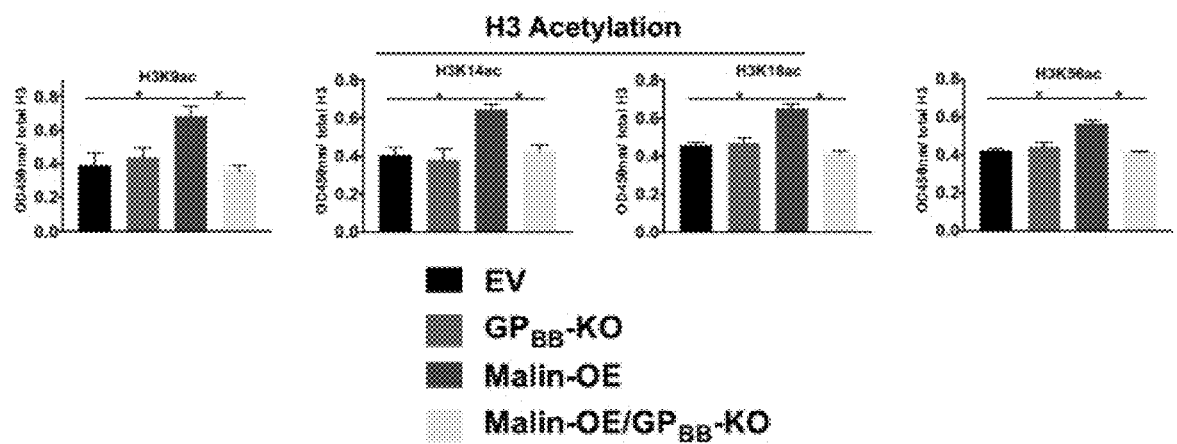
Figure 15C:
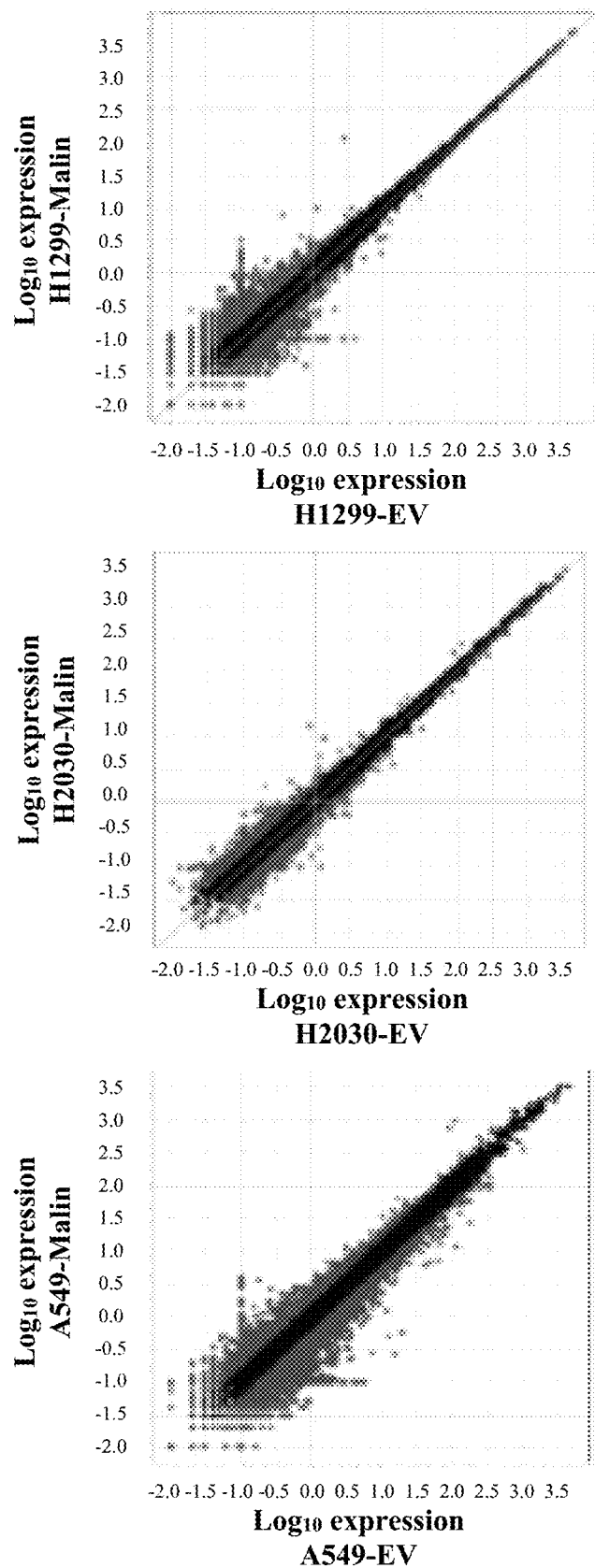

To confirm that malin-OE leads to increased acetylation in live cells, an ELISA was performed using pan-acetylation H3 and H4 histone antibodies in both EV and malin-OE cell lines (FIGS. 3F-G). Increased H3 and H4 total acetylation with malin-OE was observed, and this increase was dependent on GP$_{BB}$ as the increase was ablated in GP$_{BB}$ knockout (KO) cells. Thus, confirming that malin-OE drives nuclear glycogenolysis and histone acetylation through GP$_{BB}$. Eight additional acetylated-lysine residues were further validated on H3 and H4 in EV, malin-OE and malin-OE/GP$_{BB}$-KO cell lines, and similar trends were observed as total acetylated H3 and H4, suggesting that glycogen supplies a carbon source for global histone acetylation (FIGS. 15A-B). To this end, malin-OE also altered the transcriptomic landscape of test cell lines, observed by RNAseq analysis (FIG. 15C).

Figure 4A:
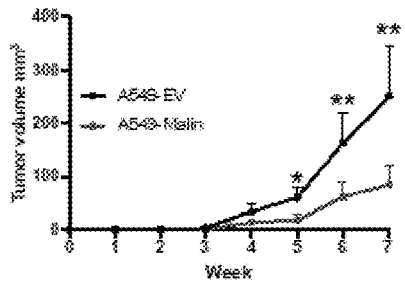
FIGS. 4A-L show graphs illustrating that malin-directed nuclear glycogenolysis occurs in vivo. (A-B) Xenograft tumor growth in (A) A549, (B) H2030, and (C) H1299 cell lines expression either EV or Malin. (D-F) Malin-OE was confirmed by IHC and quantified by HALO. (GI) Increased nuclear localization of $GP_{BB}$ in malin-OE xenografts. (J-L) Decreased nuclear glycogen is also observed in malin-OE cell lines.
Figure 4B:
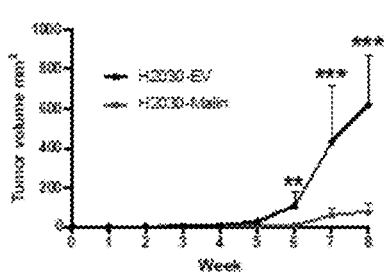
Figure 4C:
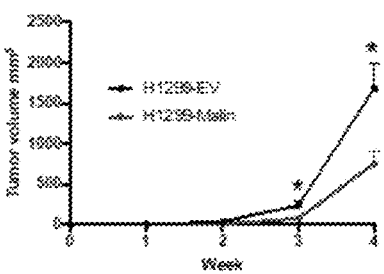
Figure 4D:
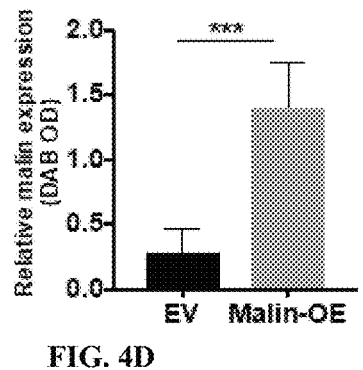
Figure 4E:
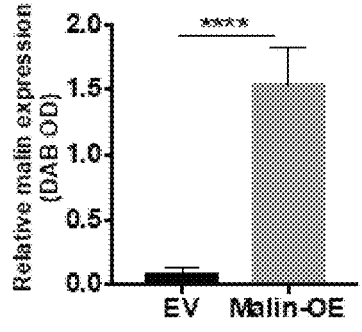
Figure 4F:
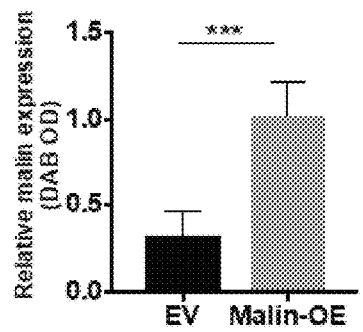
Figure 4G:
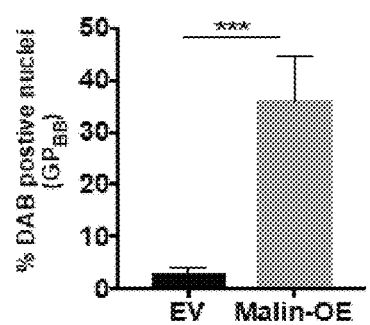
Figure 4H:
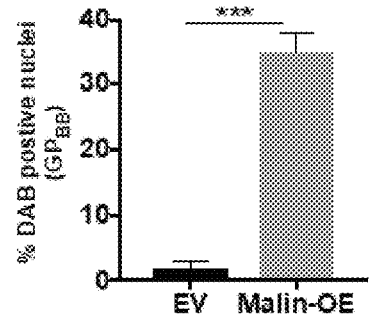
Figure 4I:
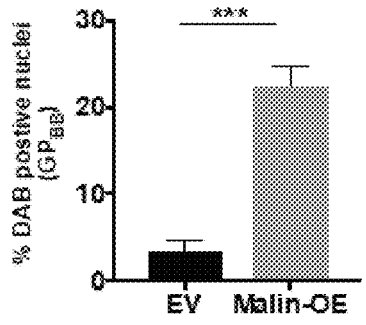
Figure 4J:
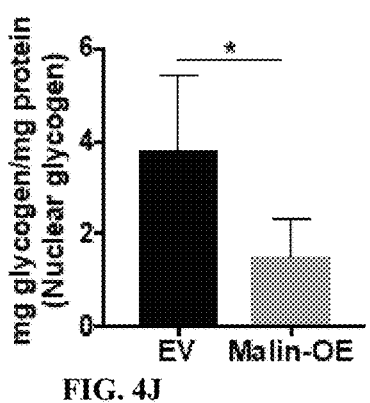
Figure 4K:
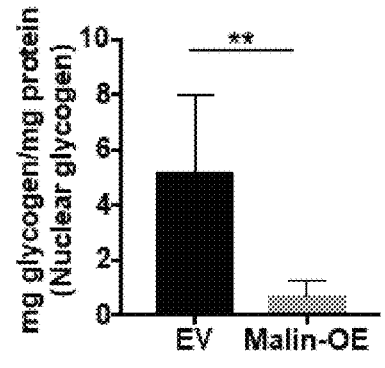
Figure 4L:
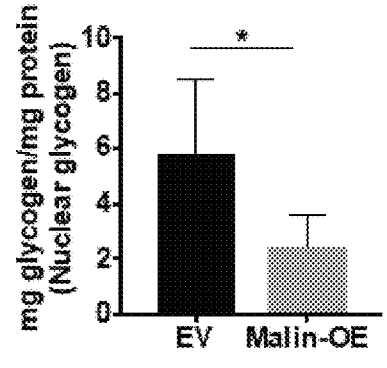
Figure 16A:
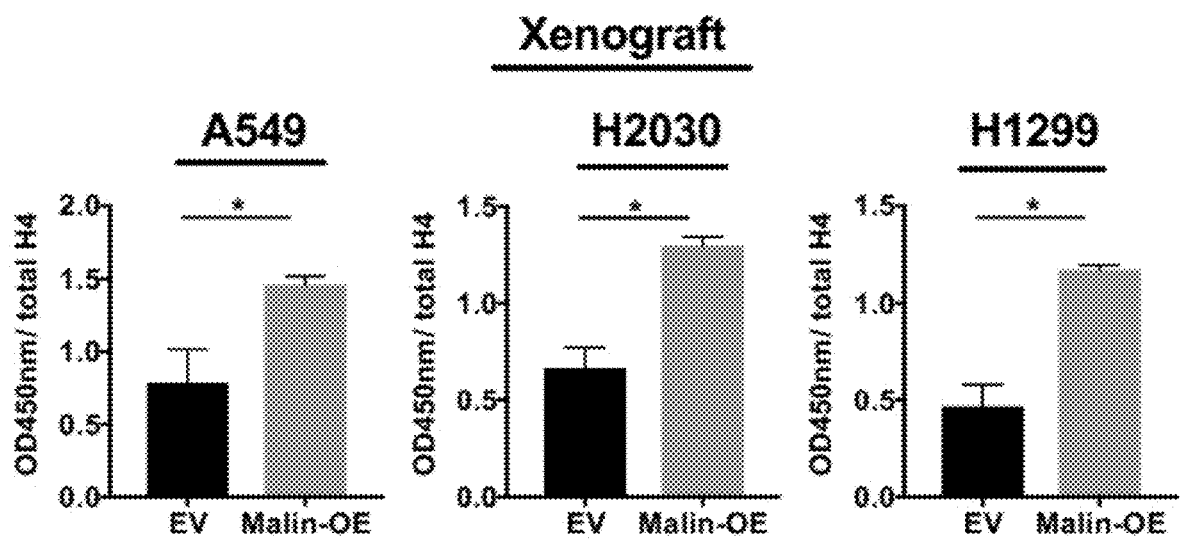
FIGS. 16A-B show graphs illustrating increased H3 and H4 acetylation in vivo. (A) Quantification of H4 acetylation in xenografts from the indicated cell lines transfected with empty vector (EV) or malin (malin-OE). (B) Quantification of H4 acetylation in xenografts from the indicated cell lines transfected with empty vector (EV) or malin (malin-OE). Data are from 10 tumors in 5 mice and are presented as mean±SE. *$0.01<P<0.05$, two-tailed t-test.
Figure 16B:
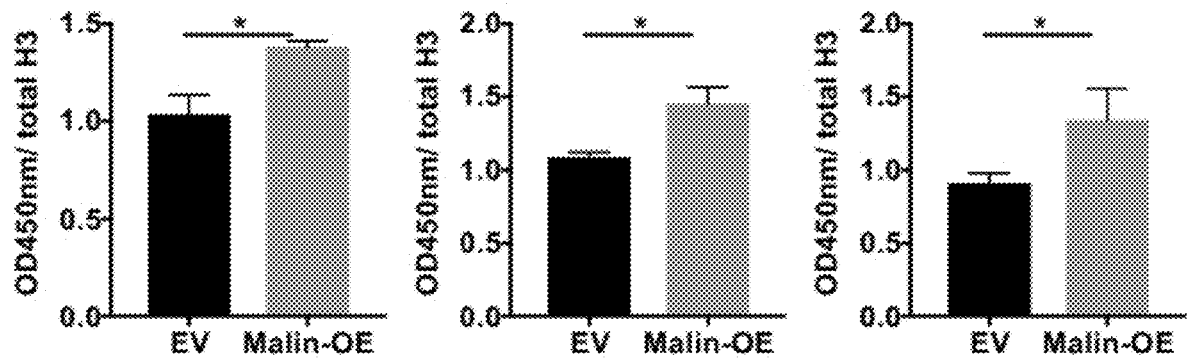

Increased histone acetylation by the inhibition of histone deacetylases suppressed tumor growth and increased apoptosis in NSCLC cell lines. To test whether increased histone acetylation through activated glycogenolysis has the same effects in NSCLC, EV and malin-OE cells were grown as subcutaneous xenografts in nude mice, and quantified tumor growth. Malin-OE OE resulted in significant reduction in tumor growth in all three cell lines when compared to control cell line growth. (FIGS. 4A-C). After confirming malin-OE (FIGS. 4D-F) and nuclear translocation of GP$_{BB}$ (FIGS. 4G-I) in tumors, nuclear glycogen (FIGS. 4J-L), H4 acetylation (FIG. 16A) and H3 histone acetylation (FIG. 16B) were measured in vivo. Accompanying the reduction in tumor growth, marked reduction in nuclear glycogen and increased H3 and H4 acetylation was observed for each model. These data confirm that nuclear glycogen is associated with increased growth rates in NSCLC, which can be reversed by malin re-expression.

These studies identify compartmentalized, nuclear glycogenolysis as a carbon source for histone acetylation. The pathway was dependent on the E3 ubiquitin ligase malin and its ubiquitination of GP. This process represents a new concept in sub-cellular organelle communication and signaling by an E3-ligase through glycogen. Compartmentalized glycogenolysis downstream of malin-GP signaling appeared to be a crucial role in regulating the epigenetic transcriptional landscape. The inability to carry out glycogenolysis in NSCLC due to a lack of nuclear GP results in a lack of substrate for histone acetylation and contributes to the altered epigenetic landscape seen in NSCLC.

These data also provide a context to understand emerging themes in cancer biology that connect metabolism with epigenetic regulation through undefined links. Mutations in metabolic enzymes such as isocitrate dehydrogenase, fumarate hydratase, and succinate dehydrogenase result in over-production of "oncometabolites" such as 2-hydroxyglutarate, fumarate, and succinate, respectively. Studies suggest that oncometabolites contribute to cancer malignancy through inhibition of histone and DNA demethylases. In addition to oncometabolites, it is known that pyruvate/acetate/citrate and serine/methionine are donors for histone acetylation and methylation, respectively. Histone hypoacetylation contributes to tumorigenesis through undefined mechanisms. Mammalian cells can promote histone acetylation through nuclear localization of pyruvate dehydrogenase, ATP citrate lyase, and acetyl-CoA synthase; however, the origin of compartmentalized substrates for these enzymes was undetermined. Recent work suggests that nuclear and cytosolic acetyl-CoA pools are maintained separately with limited equilibration between them, suggesting compartmentalized metabolism.

Figure 32A:
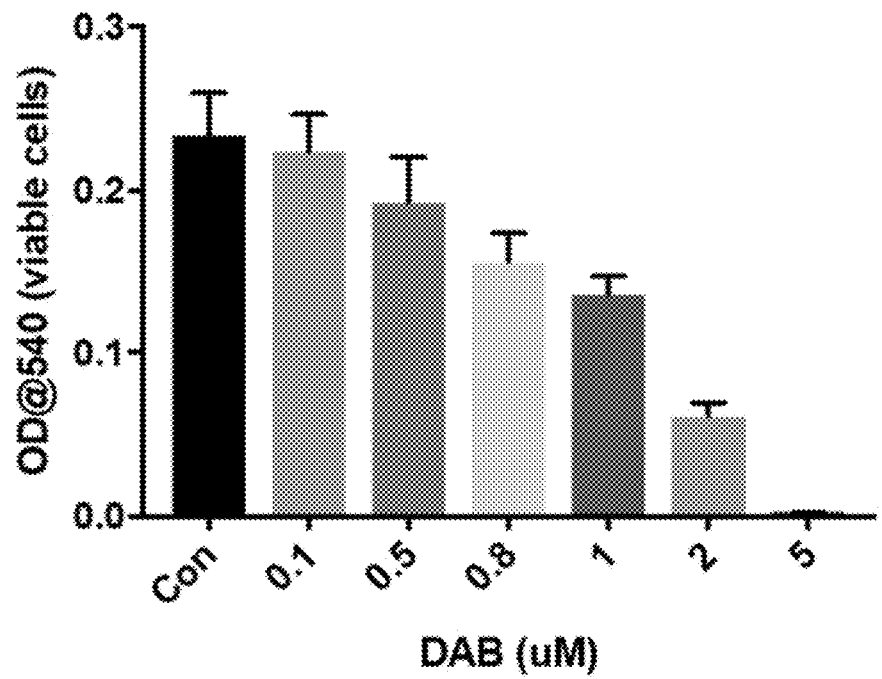
FIGS. 32A-B show graphs illustrating in vitro and in vivo efficacy of the glycogen phosphorylase inhibitor 1,4-dideoxy-1,4-imino-d-arabinitol (DAB) in non-small cell lung cancer. (A) A549 adenoma cells were treated with increasing concentrations of DAB and the IC$_{50}$ was found to be ~1.5 (B) A549 cells ($5×10^7$) were injected subcutaneously in athymic nude mice and when the tumor reached 0.1 cm$^3$ in size, a daily intraperitoneal injection of either PBS or DAB (20 mg/kg) was initiated and tumor size was measured over 15 weeks. A549 xenografts treated with DAB failed to continue to proliferate over the course of 15 weeks.
Figure 32B:
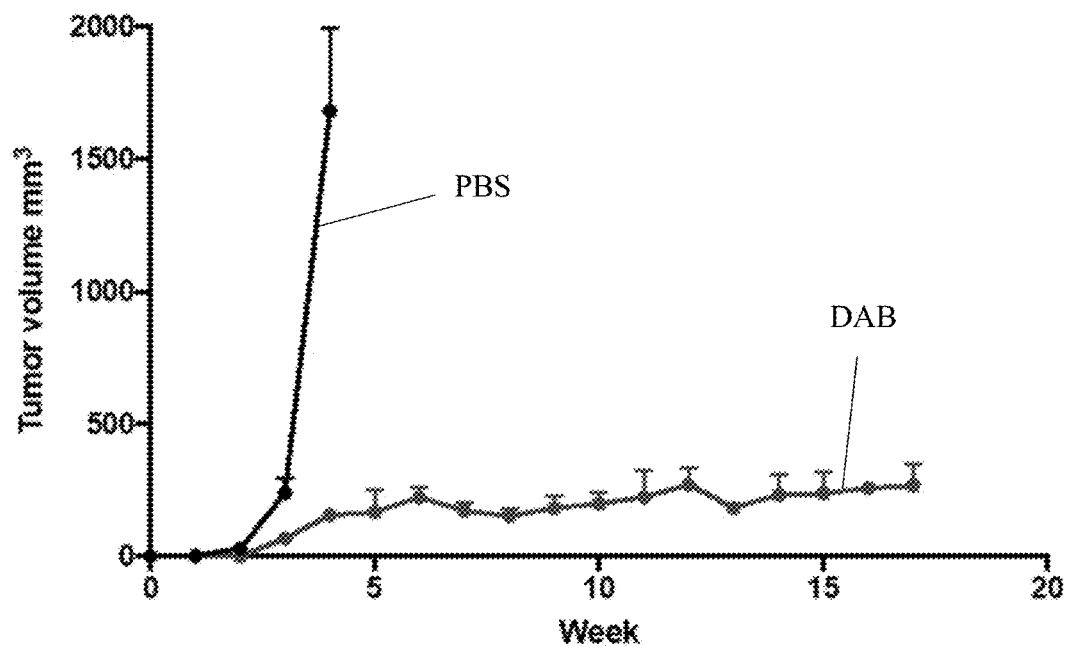

To date, histone hypoacetylation has been attributed to the increased histone deacetylases (HDACs). Nuclear glycogenolysis followed by glycolysis is yet another mechanism by which cancer can suppress histone acetylation and coordinate synergistically with HDACs to drive tumorigenesis. Downregulation of malin in NSCLC drives cellular proliferation by preventing nuclear glycogen degradation for histone acetylation. This study identifies the molecular mechanism of a half-century old observation and defines the role of nuclear glycogen beyond a simple energy cache to regulating epigenetics through acetylation. Given the significant reduction in mouse xenograft growth, the glycogen metabolic pathway represents a unique therapeutic target for NSCLC. To this end, the in vitro and in vivo efficacy of the glycogen phosphorylase inhibitor 1,4-dideoxy-1,4-imino-d-arabinitol (DAB) was evaluated in NSCLC (FIGS. 32A-B). The administration of DAB significantly decreased tumor size as compared to PBS (FIG. 32B).

Cell Lines and Animals

Cell lines H1299, H2030 and A549 were purchased from ATCC and maintained in high glucose DMEM media supplemented with 10% FBS. Low glucose media was prepared by the addition of 1 mM glucose to glucose free DMEM supplemented with dialyzed FBS (Thermo: A33382001). Human tissue samples were obtained from the Biospecimen Procurement and Translational Pathology Shared Resource Facility Athymic Foxn1$^{nu}$/Foxn1$^{nu}$(nude) mice were purchased from Jackson Laboratory (Bar Harbor, Me.). Mice were housed in a climate-controlled environment with a 1410 hours light/dark cycle (lights on at 0600 hours) with water and solid diet (except during tracer administration via liquid diet, see below) provided ad libitum throughout the study. The institutional animal care and use committee at University of Kentucky has approved all of the animal procedures carried out in this study under PHS Assurance #A3336-01.

Western

Whole-cell extracts were generated in RIPA buffer (0.5% deoxycholate, 1% IGEPAL-CA630, 0.1% sodium dodecyl sulfate, 150 mM NaCl, 50 mM Tris-8.1), lysates were cleared by centrifugation and protein concentrations were quantified with the Pierce BCA Protein Assay Kit (Thermo). For western blotting, 25 µg of protein extract per sample was denatured with heat and reducing agents, separated on a 4-12% acrylamide gel (BioRad) and transferred to PVDF (BioRad). Antibodies used for western blotting were: malin (Abcam, 1:1,000), acetyl-H3 (EMDmillipore, 1:1,000), pan-methylation (AbCAM, 1:1,000), myc (Abcam, 1:500), branching enzyme (Lsbio, 1:500), glycogen debranching enzyme (LSBio, 1:1,000), glycogen phosphorylase liver isoform (Cell Signaling Technology 46955 1:2,000), glycogen phosphorylase brain isoform (LSBio, 1:1,000), GAPDH (Abcam 1:1,0000), Histone H3 (Abcam ab1791, 1:20,000), H3K27Ae (Abcam, 1:500), Flag-M2-HRP (Sigma, 1:5000), HSP70 (Abcam, 1:5000) and H3K27me3 (Millipore 07-449; 1:4,000). Each primary antibody was incubated overnight at 4° C. Tubulin (Abcam, 1:20,000) was used as a loading control. All antibodies have detailed species validation available online from vendors. The secondary antibody anti-rabbit IgG, HRP-linked Antibody (Cell Signaling 7074, 1:5,000) or anti-mouse IgG, HRP-linked antibody (Cell Signaling 7076, 1:5,000) was incubated for 1 h at room temperature. After washing, chemiluminescence images were acquired using the ChemiDocMP (BioRad).

Immunofluorescence

Cells were fixed in 4% paraformaldehyde and permeabilized with 10% normal donkey serum (Jackson Immunoresearch) and 0.25% Triton-X (Sigma), both in PBS. Primary antibodies, malin (Abcam) and glycogen phosphorylase liver isoform (LSBio) were incubated overnight at 1:100 dilution in PBS, 10% normal donkey serum. All antibodies have detailed species validation available online from vendors. Slides were washed three times and secondary antibodies, anti-mouse-AlexaFluor594 and anti-rabbit-AlexaFluor488 (Invitrogen) were incubated at 1:500 for 1 h. After washing, cover slips were mounted using Vectashield with DAPI (Vector Labs). Imaging was performed with a Nikon 90i camera and NIS-Elements software and processed with NIS-Elements and Adobe Photoshop. All treatment groups were imaged with the same exposure time and equivalent processing.

Immunohistochemistry

De-identified human patient tissues were obtained from the Biospecimen Procurement and Translation Pathology Shared Resource Facility at the University of Kentucky. Cancer and N-distal tissues were fixed in neutral-buffered 10% formalin (NBF) then paraffin embedded and stored at the facility. Mice were sacrificed by spinal dislocation and tumors were dissected, fixed in 10% NBF. Fixed tumors and tissues were sectioned at 10 µm and immunohistochemistry was performed at the Biospecimen Procurement and Translation Pathology Shared Resource Facility using the method previously described (31). Antibodies used for other markers are listed below: malin (LSBio), Ki67 (Abcam), CC3 (Abcam), and glycogen (gift from Dr. Baba (32))

Glycogen Purification

Glycogen purification was performed based on the method described by Bloom et al (19). 10 ml of cold 10% trichloroacetic acid was added to 100 mg of frozen tissue ground to a fine suspension with SPEX sample prep tissue grinder followed by incubation on ice for 30 min with periodic gentle mixing. After centrifugation at 1500 rpm for 10 minutes, the clear supernatant solution was decanted to a fresh prechilled 50 ml tube and equal volume of cold 95 percent ethanol was added. The mixture was left in the cold room overnight on a rotating platform. The following morning, a white flocculent precipitate (glycogen) was separated by centrifugation and washed twice with 95% ethanol, the glycogen was dried in a SpeedVac (Thermo), and re-suspended in water.

Glycogen Measurement

Cells were washed twice in PBS and then lysed in 20 mM NaAcetate pH 5.3, 150 mM NaCl, 10% (v/v) glycerol, 1% (v/v) NP-40. Lysates were centrifuged at 10,000×g at 4° C. for ten minutes. Cleared lysates or purified glycogen were dissolved in ddH$_2$O, followed by acid hydrolysis with 2N HCL for 3 h at 98° C. The reaction was quenched with 2N NaOH for subsequent experiments. Glycogen-derived glucose molecules were measured by either biochemical assay or gas chromatography-mass spectrometry (GC-MS). For the biochemical assay, a portion of the digested lysate was incubated for half an hour at room temperature with 100 U L$^{-1}$ of both hexokinase and glucose-6-phosphate dehydrogenase (Sigma) in 50 mM Tris-HCl pH 7.5, 5 mM MgCl$_2$, 0.5 mM ATP, 0.5 mM NAD$^+$. The absorbance was measured at 340 nm using glucose standards to determine glycogen concentration in lysates; undigested lysates were used for background subtraction. For GC-MS analysis, samples were first dried in a SpeedVac (Thermo), followed by sequential addition of 20 mg/ml methoxyamine hydrochloride in pyridine, and then the trimethylsilylating agent N-methyl-N-trimethylsilyl-trifluoroacetamide (MSTFA) was added. GC-MS settings are defined below. Glycogen content was normalized to protein concentration.

Affinity Purification-Mass Spectrometry

His6-tagged malin was purified using affinity purification with Ni-NTA resin. Lysates of HEK293 cells were subjected to centrifugation at 10,000×g to remove insoluble debris. Malin was incubated with Ni-NTA-agarose beads either with or without the pre-cleared lysates from HEK293 cells for 2 hrs. The samples were washed three times in wash buffer (Tris buffered saline (pH 7.4), 0.5% Triton X-100, and 2 mM dithiothreitol). Bound proteins were removed in the presence of Laemmli's buffer and heated at 98° C. for 10 minutes. Proteins were separated by denatured gel electrophoresis on NuPAGE 10% Bis-Tris gels, gels were stained with Coomassie, bands were excised from gels, digested with trypsin, desalted, and analyzed by MALDI TOF/TOF. The peptide fragments were searched with Protein Pilot software against Swiss-Prot database. The mass spectrometric analysis was performed at the University of Kentucky, Proteomics Core Facility Immunoprecipitations Cells were collected on ice in lysis buffer [10 mM TrisHCl pH 8; 150 mM NaCl, 15 mM EDTA; 0.6 M sucrose, 0.5% nonidet P-40 (NP-40), protease inhibitor cocktail (Roche), 1 mM PMSF, 50 mM NaF and 5 mM $Na_2P_2O_7$,]. Lysates were cleared by centrifugation at 10,000×g. For immunoprecipitations in the absence of glycogen, 125 μl of 2 U/ml amyloglucosidase was added to lysates for 2 hrs at 4° C. The supernatants were mixed with anti-myc agarose (Sigma, A7470) or antibody of interest plus protein A-conjugated agarose beads (Invitrogen) and incubated for 2 hrs at 4° C. The beads were pelleted at 1,000×g for 2 min and washed three times in lysis buffer. Samples were then mixed with Laemmli's buffer and heated at 95° C. for 10 min. Beads were removed by centrifugation and samples were subjected to Western blot analysis. All experiments utilizing Western analysis were performed a minimum of three independent experiments and the results are representative of each experiment.

In Vitro Ubiquitination $^{35}$S-labelled myc-$GP_{LL}$ was generated using the TNT Coupled transcription/translation System (Promega) per manufacturer's protocol and probed for quality using gel electrophoresis and phosphorimaging using Typhoon FLA 9500 (GE). In a standard ubiquitin assay reaction, myc-$GP_{LL}$ was combined with GST-malin (2 μg), Mg-ATP (4 mM), His6-Ub (5 μg), His6-UbE1 (100 nM), GST-UbcH5a (200 nM) in assay buffer (50 mM Tris-HCl pH 7.5, 2.5 mM $MgCl_2$, 0.2 mM DTT and 2 mM ATP) and was incubated for 1 h at 37° C. myc-$GP_{LL}$ was immunoprecipitated from the reaction mixture using anti-myc agarose beads (Sigma), washed three times in assay buffer, and eluted in Laemmli's buffer by heating samples at 95° C. for 10 min. Proteins were separated using gel electrophoresis and probed by an anti-ubiquitin antibody (Biolegend).

$^{13}$C-Glycogen Labeling in Mice

A liquid diet base containing casein, L-cystine, soy oil, cellulose, mineral mix (AIN-93G-MX), calcium phosphate, vitamin mix (AIN-93-VX), choline bitartrate, tert-butylhydroquinine (TBHQ), and Xanthan gum was purchased from Harlan Laboratories (Madison, Wis.). Ultrapure grade $^{13}C_6$-glucose was obtained from Cambridge Isotope Laboratories (Tewkebury, Mass.). For the $^{13}$C-glycogen enrichment, unlabeled glucose and water were added to the diet base two days prior to the tracer study to give a final diet of 0.167 g glucose/g diet and a net protein content of 53 mg/g diet to provide sufficient carbon and nitrogen according to the vendor. 20 g mice were fed 13.6 g liquid diet (at 680 g diet/kg mouse). This pre-feeding of unlabeled liquid diet served to accustom the mice to the liquid diet feeding. On the third day, $^{13}C_6$-glucose at 0.173 g/g diet replaced the unlabeled glucose in the diet for each mouse and the mice were allowed to consume the diet ad libitum for 48 h. At the end of the feeding period, mice were sacrificed by spinal dislocation and organs were harvested and snap frozen in liquid nitrogen. The frozen liver was pulverized into 10 μm particles in liquid $N_2$ using a SPEX SamplePrep freezer mill (SPEX) and glycogen was extracted using TCA and ethanol precipitation via the method previously described (18).

Nuclear Purification

Nuclear extracts were prepared according to the method of Schreiber et al and Nagata et al (33,34). For cell lines, after washing with PBS, $10^7$ cells were suspended in cell lysis buffer (10 mM HEPES pH 7.5, 10 mM KCL, 0.1 mM EDTA, 1 mM DTT, 0.5% NP40 and protease/phosphatase inhibitor cocktail, Cell Signaling) for 20 min on ice with intermittent gentle mixing. At the end of incubation, tubes were vortexed, then nuclei were pelleted at 12,000×g for 10 min at 4° C. by centrifugation followed by two more washes with the lysis buffer. For tissue samples, frozen tissue was ground to a fine suspension (<10 μm particles) with a SPEX SamplePrep, and 20 mg of tissue powder was suspended in tissue lysis buffer (10 mM HEPES pH 7.5, 10 mM KCL, 0.1 mM EDTA, 1 mM DTT, 0.5% NP40, 10 mg/ml collagenase IV, Sigma and protease/phosphatase inhibitor cocktail, Cell Signaling) followed by centrifugation. The nuclei pellet was further resuspended in ice cold fractionation buffer (2 M sucrose, 1 mM $MgCl_2$ and 10 mM Tris-HCL pH7.4) and mixed well then centrifuged at 16000×g for 30 minutes at 4° C. After removal of supernatant, the ultrapure nuclei were further washed twice with cell lysis buffer. To study nuclear glycogen metabolism, pelleted nuclei were washed twice with cell lysis buffer, then resuspended in nuclear extraction buffer (20 mM HEPES, pH 7.5, 400 mM NaCl, 1 mM EDTA, and protease/phosphatase inhibitor cocktail, Cell Signaling) followed by the addition of $^{13}$C-glycogen.

Stable Isotope Labelling in Organella

Intact nuclei were resuspended in 500 μl of respiration buffer (125 mM KCL, 2 mM MgC1, 2.5 mM $KH_2PO_4$, 20 mM HEPES pH7.2, 1 mM ATP, 0.01 mM ADP, 1 mM NAD+, 0.01 mM NADH) supplemented with either 1 mM $^{13}$C-glycogen, 1 mM $^{13}C_6$-glucose and $^{13}C_6$-glucose-6-phosphate for 1-6 h at 37° C. with periodic mixing. For lysed nuclei, 400 ul of respiration buffer supplemented with 1 mM $^{13}$C-glycogen were added to 100 ul of lysed nuclei and incubated for 3 h at 37° C. with periodic mixing. At the end of incubation equal parts of pre-chilled 100% methanol was added to the mixture to precipitate out proteins and lipids. The polar fraction was transferred to a V-shaped GCMS glass vial and dried using a SpeedVac (Thermo) followed by derivatization and GC-MS analysis. Dried polar samples were derivatized by sequential addition of 20 mg/ml methoxylamine hydrochloride in pyridine then the trimethylsilylating agent N-methyl-N-trimethylsilyl-trifluoroacetamide (MSTFA) with brief agitation in between at 80° C. After cooling, the derivatized mixture was transferred to an autosampler vial for analysis.

GC-MS Analysis

GC-MS protocols were similar to those described previously (35,36), except a modified temperature gradient was used for GC: Initial temperature was 130° C., held for 4 minutes, rising at 6° C./min to 243° C., rising at 60° C./min to 280° C., held for 2 min. The electron ionization (EI) energy was set to 70 eV. Scan (m/z:50-800) and selected ion monitoring mode were used for qualitative measurement and isotope monitoring, respectively. Ions used for metabolites that represent the entire carbon backbone are: glucose (554), glucose-6-phosphate (706), fructose-6-phosphate (706), 3PG (387), pyruvate (174) respectively. Batch data processing and natural $^{13}$C labeling correction were performed using the Data Extraction for Stable Isotope-labelled metabolites (DEXSI) software package (37). Relative abundance for isotopic ions were corrected for recovery using the L-norvaline and adjusted to protein input.

Extraction of Total Acetate from Histones

Following organello labelling from above, the protein pellet was further purified for histones by re-suspending in 0.4 N sulfuric acid followed by mixing and incubated on a rotating platform overnight. The following morning, the mixture was centrifuged at 16,000×g for 10 minutes and the supernatant (containing histones) was mixed with TCA and incubated on ice for 30 minutes. Histones were pelleted at 16,000×g for 10 minutes in a refrigerated centrifuge for acetate extraction. Bound acetate hydrolysis was performed by saponifying the histone pellet overnight by incubation with 200 μL of 10 M sodium hydroxide in a microfuge tube at 95° C. Each sample was then cooled on ice before adding 150 μL of concentrated hydrochloric acid, followed by drying by SpeedVac (Thermo). The dried samples were reconstituted in 200 μL of water and further derivatized as described below.

Chemical Derivatization of Acetate

200 μL of sample was added to a 2 mL microfuge tube, 50 μL of 1-propanol, and 50 μL of pyridine. The tube was then placed on ice for 5 min. 100 μL of 1 M sodium hydroxide was then added, immediately followed by 30 μL MCF and vigorous vortexing for 20 seconds. As gas built up in the microfuge tube during the derivatization reaction, the lid was kept closed with one finger and carefully opened after vortexing to relieve pressure (or the lid was kept open during vortexing). After vortexing, 300 μL of MTBE was added, the sample vortexed for another 20 s, and centrifuged at 10,000 g for 5 min. 200 μL microliters of the resulting upper layer was transferred to a GC vial for analysis.

Acetate Quantification by GC-MS

The acetate samples were analyzed with an Agilent 7890B GC system coupled to a 5977B MSD GC-MS system. A DB-75 column was used (30 m×0.25 mm×0.25 μm). Samples (2 μL) were injected using split mode (0.5 bar, 25 mL/min split flow). The column gas flow was held at 1.0 mL of He per min. The temperature of the inlet was 280° C., the interface temperature 230° C., and the quadrupole temperature 200° C. The column was equilibrated for 2 min before each analysis. The mass spectrometer was operated in scan mode between 2.2 and 2.7 min with a mass range of 30-150 AMU at 1.47 scans/s. MNOVA software were employed for automated data processing using peak heights of m/z 61, 62 and 63 ions used to quantify $^{12}C$ and $^{13}C$, respectively (the peak shapes were consistently highly symmetric, and using either peak area or peak heights gave equivalent results).

Xenograft

For in vivo tumor growth, H1299, H2030 and A549 cells were dissociated into single cells, counted and resuspended at $5 \times 10^6$ cells per 100 μl of 1:1 media/matrigel (BD). 8-10-week-old female Foxn1$^{nu}$/Foxn1$^{nu}$(Nude) mice (JAX Laboratories) were injected subcutaneously with $5 \times 10^6$ cells on both sides of the flanks. Tumor growth was measured twice a week by caliper in a non-blinded fashion. Tumors were allowed to grow upwards of 1000 mm$^3$. All mouse experiments were approved by the BCH Animal Care and Use Committee and by the University of Kentucky Institutional Animal Care and Use Committee, both accredited by the Association for Assessment and Accreditation of Laboratory Animal Care and were performed in accordance with relevant institutional and national guidelines and regulations.

RNAseq GSEA Analysis

RNA from cell lines were isolated using the RNeasy kit (Qiagen). RNA sequencing was performed using the Illumina HiSeq 4000 system. The RNAseq data was processed using Cutadapt to trim adapters and STAR to align reads to the reference genome. For the differential expression (DE) analysis, HTSeq was used to count gene expression level, DESeq2 and EdgeR was used to identify differentially expressed genes between EV and malin-OE.

Statistics

Statistical analyses were carried out using GraphPad Prism. All numerical data are presented as mean±SD except for xenograft tumor growth which is presented as mean±S.E. Grouped analysis was performed using two-way ANOVA. Column analysis was performed using one-way ANOVA or t-test. A P-value less than 0.05 was considered statistically significant.

Example 2

This Example discusses the discovery that Ewing's Sarcoma (ES)-glycogen is both hyper-phosphorylated and hyper-branched, making it architecturally distinct from normal glycogen. As discussed below, there is strong evidence to show that ES-glycogen is critical for ES proliferation. The data presented herein establishes that ES-glycogen results from loss of malin, an E3 ubiquitin ligase that regulates glycogen architecture. It also demonstrates that ES-glycogen binds to AMP-activated protein kinase (AMPK) with high affinity and renders AMPK inactive. Further, it shows that a genetic manipulation normalizing ES-glycogen architecture significantly reduces glucose flux and delays xenograft ES tumor growth by 70%. Finally, xenograft tumor growth was reduced using a small molecule inhibitor targeting glycogen synthase (GYS) that reduces ES-glycogen accumulation. Based on these results, it is believed that ES-glycogen drives cellular proliferation by modulating cellular metabolism, and it is a promising therapeutic target.

Figure 17A:
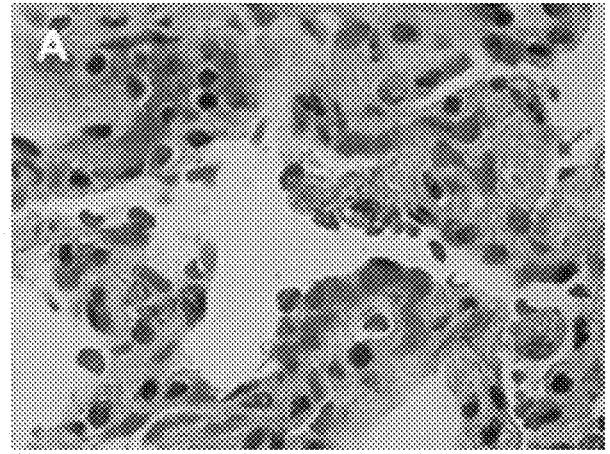
FIGS. 17A-B show images illustrating intracellular glycogen deposits that are Periodic acid-Schiff (PAS) and PET positive in Ewing's sarcoma. (A) PAS staining in Ewing's sarcoma patient samples showing large glycogen deposits (dense pink staining). (B) The same patient is also PET positive, arrow showing Ewing's sarcoma with increased fluorodeoxyglucose uptake under PET-CT.
Figure 17B:
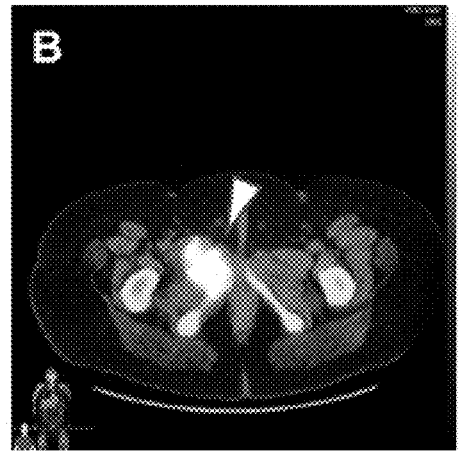

Ewing's sarcoma has aberrant glycogen accumulation. ES is the second most common pediatric bone cancer in adolescent and young adults. Intensified chemotherapy regimens have incrementally improved recurrent or metastatic ES outcomes, motivating research and development of new treatment options to combat this deadly disease. Two clinical features of ES are the accumulation of intracellular glycogen deposits that are Periodic acid-Schiff (PAS) positive during pathological analysis (FIG. 17A) and the EWS-FLI1 fusion oncogene. Contribution of EWS-FLI1 to tumorigenesis and epigenetics is well studied, but little is known about the biology and pathology of ES-glycogen nor has ES-glycogen metabolism been explored as an anti-ES target. ES is positron emission tomography (PET) positive using 18F-fluorodeoxyglucose (FIG. 17B), which is often associated with increased glucose uptake and metabolic reprogramming in other fast-growing cancers. Both ES-glycogen accumulation and PET positive lesions provide evidence that metabolism is an important aspect of ES.

Figure 18:
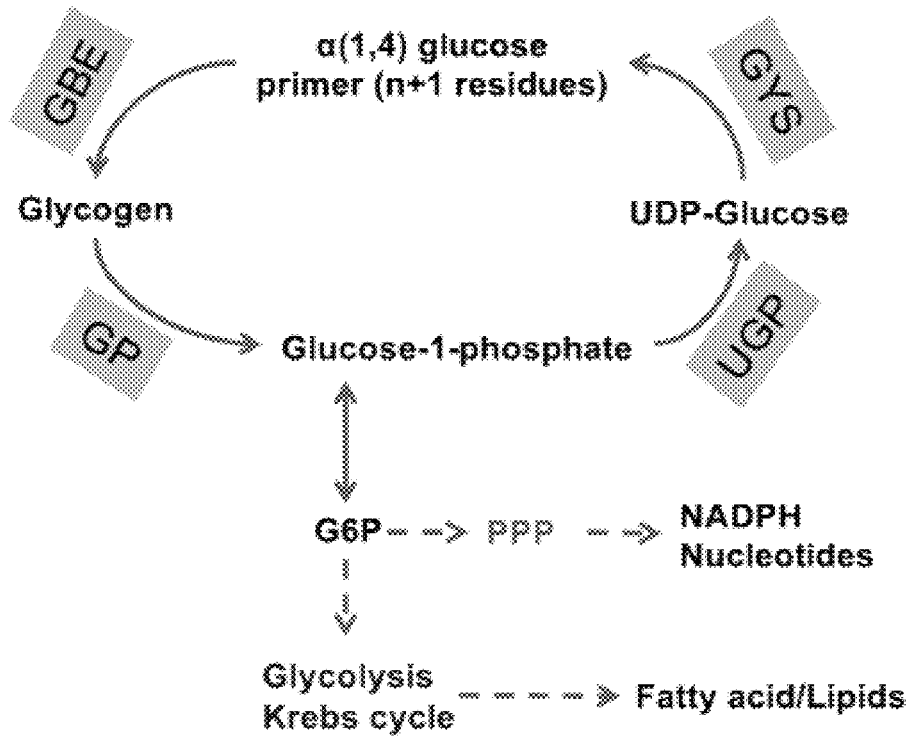
FIG. 18 shows a schematic illustrating key enzymes involved in the synthesis and breakdown of glycogen and other metabolic networks connected to glycogen metabolism. PPP=Pentose Phosphate Pathway.

Glycogen metabolic enzymes. Glycogen is the primary source of storage carbohydrate in mammals, it is found in most tissues, including liver, muscle, kidney, brain, and white blood cells. The synthesis and breakdown of glycogen involves several enzymes and regulatory proteins. UDP-glucose-pyrophosphorylase (UGP), glycogen synthase (GYS), and glycogen branching enzyme (GBE) work together to assemble a branched glycogen molecule, which enables a high packing density of glucose for maximum storage. During glycogenolysis (glycogen breakdown), glycogen phosphorylase (GP) releases glucose-1-phosphate molecules to fuel metabolic processes. Glycogen synthesis and degradation either consumes or produces glucose-6-phosphate (G6P), a key metabolite essential for energy production, lipid, and nucleotide biosynthesis (FIG. 18).

Figure 19:
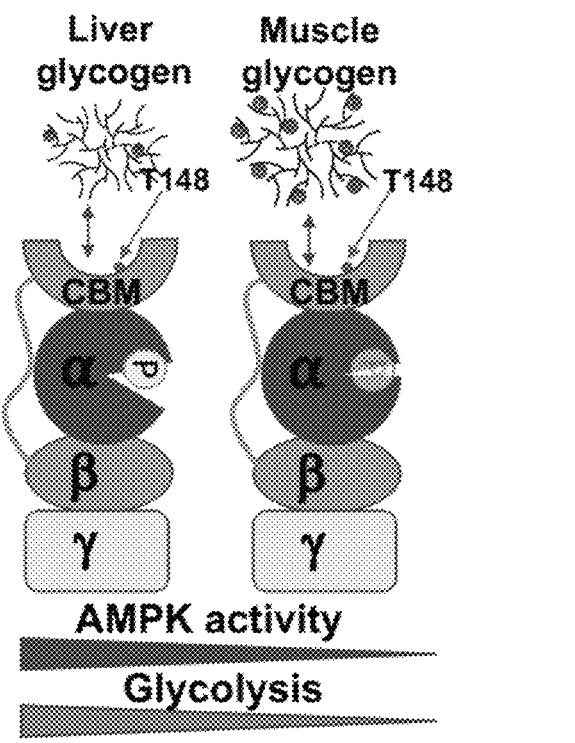
FIG. 19 shows a schematic illustrating muscle and liver glycogen architecture, and their interactions with AMPK. Both interact with AMPK via the CBM domain of the β-subunit. Interaction is dependent on residue T148. Higher branched, phosphorylated and extended muscle glycogen has an inhibitory effect on p-AMPK activity.

Glycogen binds to AMPK through the CBM domain. AMP-activated protein kinase (AMPK) controls key cellular processes, such as cellular proliferation and autophagy, through reprogramming of metabolic pathways. In mammals, AMPK exists as a heterotrimer (AMPKαβγ), containing a catalytic subunit (α) and regulatory subunits (β and γ) (FIG. 19). AMPK activation is controlled through a combination of: 1) energy state sensing (i.e., ATP/AMP, ATP/ADP ratios) and 2) upstream kinase phosphorylation by calcium/calmodulin dependent protein kinase 2 (CAMKKβ) and liver kinase B1 (LKB1). Both CAMKKβ and LKB1 can activate AMPK by phosphorylation of Thr174 of the α-subunit. Activated AMPK increases the rate of glycolysis and suppresses fatty acid synthesis by phosphorylation of phosphofructokinase 2 (p-PFK2) and acetyl-CoA carboxylase (p-ACC), respectively. AMPK activation opposes tumor development and loss of AMPK activity results in aberrant cancer metabolism that drives tumor growth.

Figure 20:
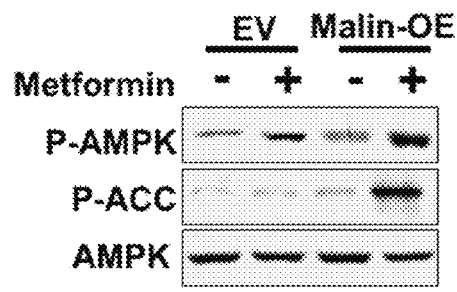
FIG. 20 shows an image illustrating in vitro assay demonstrating that malin-OE results in an increase in p-ACC after metformin treatment when compared to EV alone.

The β subunit of AMPK (AMPKβ) contains a conserved region called the carbohydrate binding module (CBM), and threonine 148 (AMPKβ$_{T148}$) of the CBM is a key amino acid for the glycogen/AMPK interaction (FIG. 19). Phosphorylation of T148 or substitution with the phosphomimic aspartic acid (AMPKβ$_{T148D}$) prevents AMPK binding to glycogen. Conversely, the AMPKβ$_{T148A}$ mutant binds to glycogen with greater affinity. There have been correlative studies on glycogen levels and AMPK activity, but the molecular mechanisms of these events are poorly defined. Using p-ACC as a read out for AMPK activity, the present inventors discovered that ES-cells have low basal AMPK activity and the cells are insensitive to the AMPK activator metformin (FIG. 20).

Glycogen architecture regulates AMPK activity. Glycogen modeling or architecture describes the frequency of branch points, glucose chain length, and total phosphate esters. These architectural properties define the granular size and crystallinity (solubility) of a glycogen molecule and its accessibility to glycogen interacting enzymes. A broad spectrum of storage carbohydrates exists within nature based on their architecture. At one end of the spectrum, liver glycogen has an average chain length of 13 residues and approximately 1 phosphate per 500-2000 glucose residues to maintain maximum solubility for rapid turn-over during periods of starvation. Although still considered normal, muscle glycogen is architecturally distinct from liver glycogen. Muscle glycogen exhibits modest increases in chain length and branching compared to the liver, and it is resistant to degradation during starvation (FIG. 19). At the other end of the spectrum, malignant polyglucosan bodies (PGB), such as those found in neurodegeneration and heart failure have an average chain length of 30 residues, with 10-fold higher phosphate esters to expand granular size, increase crystallinity and reduce accessibility to degradation enzymes.

Glycogen architecture modulates AMPK activity. For example, muscle glycogen has longer chain length, increased branching, and phosphate levels compared to liver glycogen. These characteristics result in greater binding affinity between muscle glycogen and AMPK, and this binding is inhibitory over the active form of AMPK (p-AMPK activity) (FIG. 19). The data presented herein shows that ES-glycogen is architecturally unique from both liver and muscle glycogen (FIGS. 21A-D). Additionally, it is shown that ES-glycogen binds to AMPK with high affinity and is a negative regulator of p-AMPK activity even overriding AMPK activators (FIGS. 20 and 22A-C).

Figure 23:
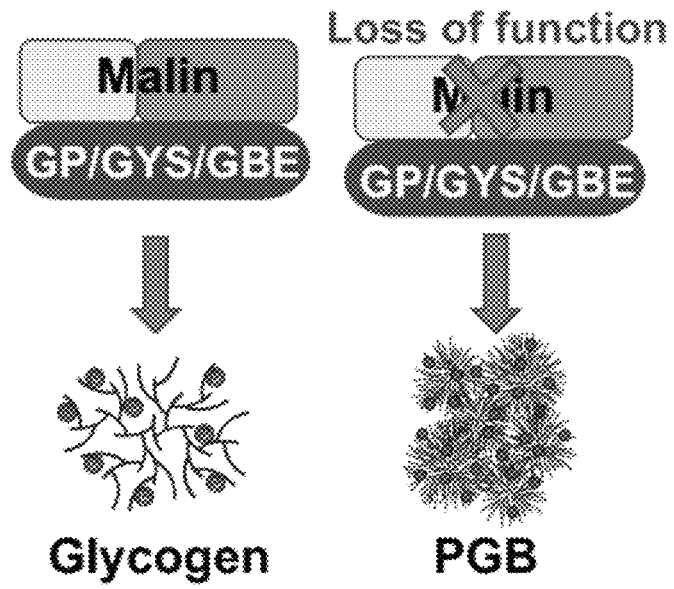
FIG. 23 shows schematics illustrating the loss of malin results in PGB formation and compromised glycogen metabolism.
Figure 24:
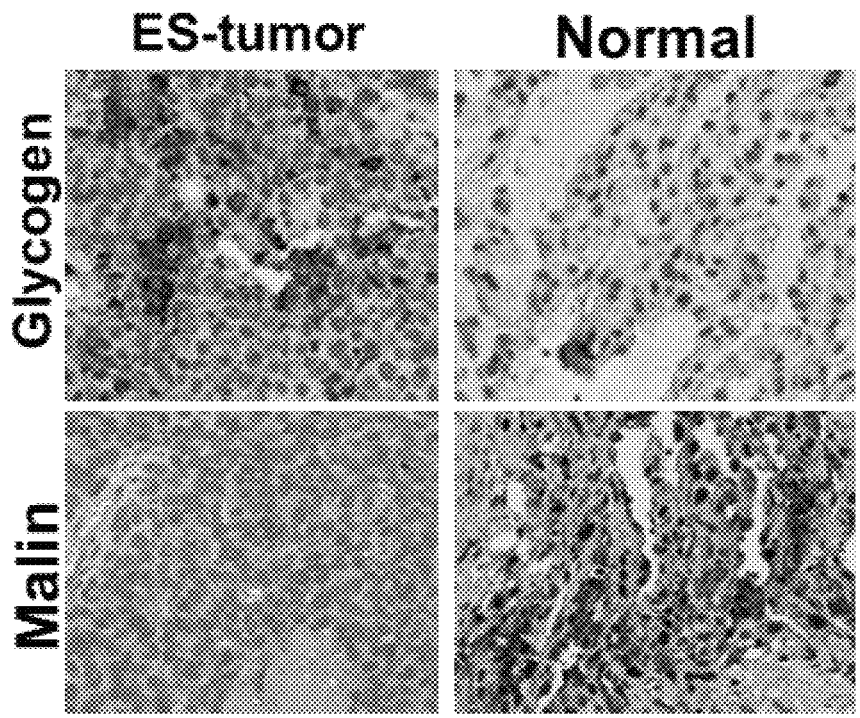
FIG. 24 shows images illustrating histochemical analysis of glycogen (top) and malin (bottom) in ES and normal patient samples.

Malin modulates ES-glycogen architecture. Research on the regulation of mammalian glycogen architecture and its functional roles in cellular physiology is beginning to emerge and malin has been identified as a key enzyme in modulating glycogen architecture. The present inventors have discovered that malin functions as an E3 ubiquitin ligase that ubiquitinates multiple proteins involved in glycogen metabolism, including GYS, laforin, and protein targeting to glycogen (PTG). Interestingly, malin can regulate the stability and localization of enzymes involved in glycogen metabolism through ubiquitination. While the detailed mechanism of action for malin is an area of active research, it is clear that malin is required for coordinated glycogen metabolism as somatic loss-of-function mutations in malin result in the formation of PGB (FIG. 23). Changes in malin expression in different cancers has not been reported thus far, but the histochemical analysis presented herein shows patient ES specimens have significantly reduced malin protein levels compared to paired normal tissues (FIG. 24).

Define the Contribution of Malin to ES-Glycogen Architecture.

Malin is an E3-ubiquitin ligase that interacts with critical glycogen metabolic enzymes, e.g., GYS, glycogen debranching enzyme, and glycogen phosphorylase. However, these interactions are not limited to proteasomal degradation. The loss of malin and accumulation of PGB-like glycogen has been linked to multiple cellular outcomes/pathways, including: increased ER stress, decreased proteasomal activity, increased misfolded proteins, and decreased autophagy in neurological disorders, but no link has been reported in cancer.

Consistent with abnormal ES-glycogen, the present inventors have found that expression of malin is downregulated by 70-90% in ES patient samples. Importantly, the data presented herein shows that re-expression of malin remodels ES-glycogen to restore normal architecture and delays in vivo xenograft growth by up to 70%. To define this promising new signaling event, in vitro and in situ biochemical methods are used to (1) determine the type of ubiquitin chains malin promotes on glycogen metabolic enzymes, (2) identify ubiquitinated lysine residues by mass spectrometry, (3) establish the functional consequences of ubiquitination-resistant mutants to ES-glycogen formation and tumor growth and (4) correlate ES-glycogen and malin protein levels with clinical course of a cohort of 55 ES patients at different stages.

In particular, this Example shows that ES-glycogen is architecturally similar to PGB due to the lack of malin expression and a unique feature of ES. The data presented herein demonstrates that re-introduction of malin in ES cell lines results in the remodeling of ES-glycogen and significantly reduces tumor growth in vivo, suggesting that ES cellular proliferation is linked with ES-glycogen. In view thereof, it is believed that ubiquitination of glycogen metabolic enzymes by malin alters their binding affinity to glycogen, enzyme activity and sub-cellular localization. Collectively, these parameters are crucial to the optimal modeling of glycogen architecture, and a disruption in this process results in ES-glycogen and increased ES cellular proliferation.

Figure 21A:
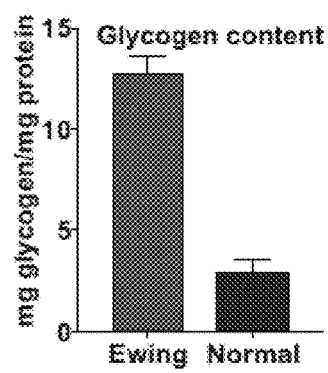
FIGS. 21A-D show graphs and an image comparing ES-glycogen to normal glycogen. (A) Biochemical quantitation of ES-glycogen vs. normal. (B) Total phosphate content in purified ES and normal glycogen. (C) Iodine staining showing increased chain length and branching in ES-glycogen. (D) ES-glycogen resembles PGB based on glycogen architecture.
Figure 21B:
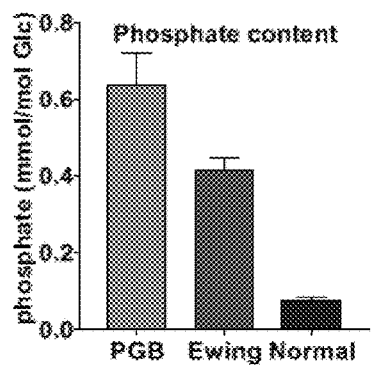
Figure 21C:
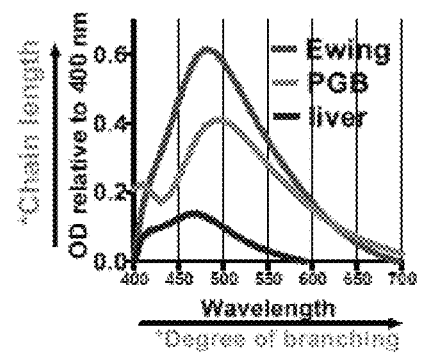
Figure 21D:
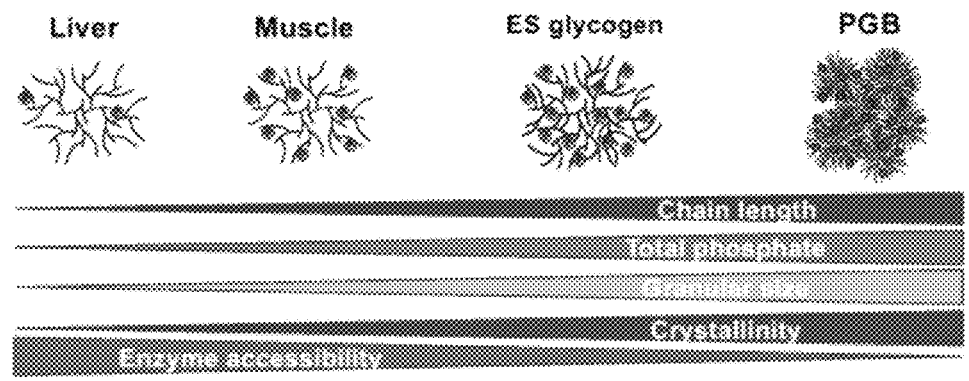

ES patient specimens have architecturally abnormal glycogen and low malin. Paired ES cancer and normal tissue resected at surgery were analyzed for glycogen content (n=3). Glycogen accumulation in ES cancers was identified and quantified by immunohistochemistry using a glycogen specific antibody. Large glycogen vacuoles are clearly visible throughout ES cells, but barely visible in the paired N-distal normal tissue (FIG. 24). Aberrant ES-glycogen accumulation is accompanied by the low expression of malin at the protein level (FIG. 24). ES-glycogen was further purified and analyzed for architectural abnormalities using multiple biochemical methods. ES-glycogen contains 4-fold higher phosphate than normal tissue glycogen and has increased chain length and degree of branching by iodine spectra analysis (FIGS. 21A-C). ES-glycogen architectural properties closely resemble the malignant PGB purified from a mouse model of neurodegeneration (FIG. 21D).

Figure 25A:
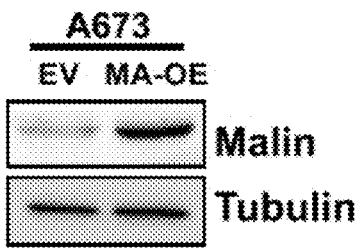
FIGS. 25A-F show graphs and images illustrating effects of malin-OE. (A) Immunoblotting analysis of malin-OE in the ES cell line, A673. (B) Biochemical quantitation of ES-glycogen in EV and malin-OE cell lines. (C) Total phosphate content in purified glycogen from A673-EV and malin-OE cell lines. (D) Iodine staining of glycogen from EV or malin-OE cells showing decreased chain length after malin-OE. (E) Malin-OE significantly reduced A673 tumor growth in vivo. (F) Reduced proliferative markers Cyclin D1 (CD1) and Ki67 and A673 malin-OE tumors.
Figure 25B:
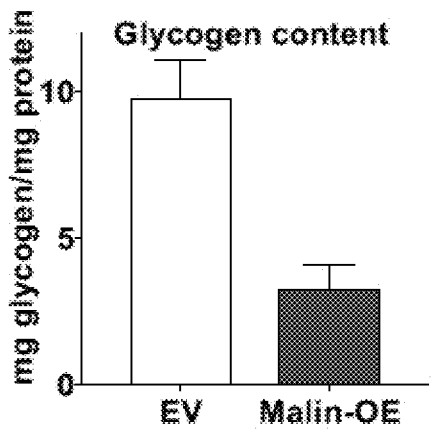
Figure 25C:
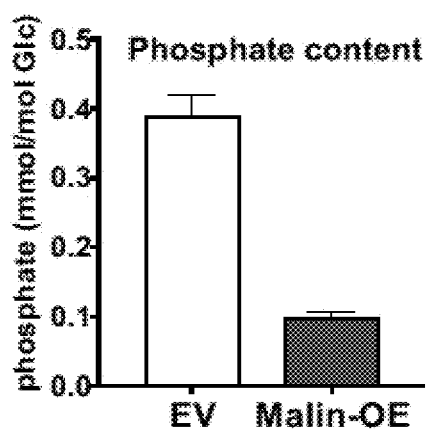
Figure 25D:
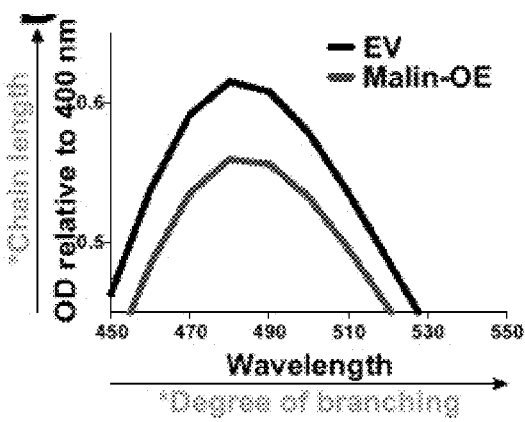
Figure 25E:
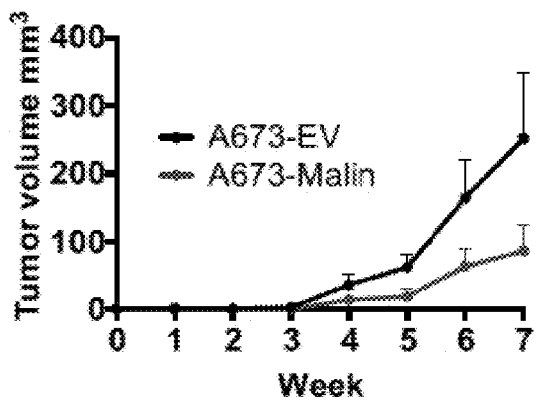
Figure 25F:
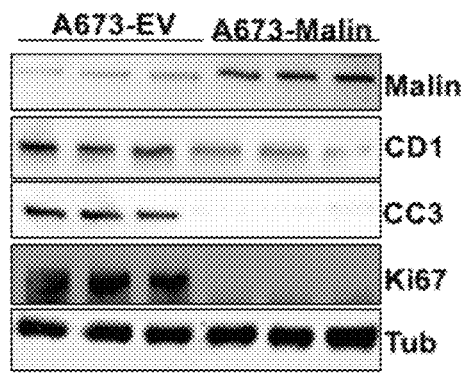

Malin-expression alters ES-glycogen architecture and reduces tumor growth. To study the impact of malin on glycogen architecture and cellular proliferation in ES cell lines, malin was over-expressed (malin-OE) in three different ES model cell lines, A673, TC32, and HS822T. Malin-OE significantly reduced total phosphate and chain length of glycogen compared to the empty vector control (EV) (FIGS. 25A-D), suggesting a remodeling of ES-glycogen to a more normal architecture. Malin-OE also resulted in a reduction in total glycogen content in cell lines (FIG. 25B). A673-EV and malin-OE cell lines were grown as xenografts in immunocompromised mice to assess tumor growth in vivo. Malin-OE significantly reduced tumor growth in vivo (FIG. 25E), TC32, and HS822T all share similar results (data not shown). Immunoblotting analyses of these tumors show decreased proliferative marker Ki67 and cyclin D1 (CD1) and also reduced level of apoptosis marker, cleaved caspase 3 (CC3), in cell lines with malin-OE (FIG. 25F). Furthermore, no glycogen was detected in malin-OE tumors which confirmed malin-directed remodeling of glycogen architecture leads to rapid glycogenolysis in vivo (data not shown).

Figure 26A:
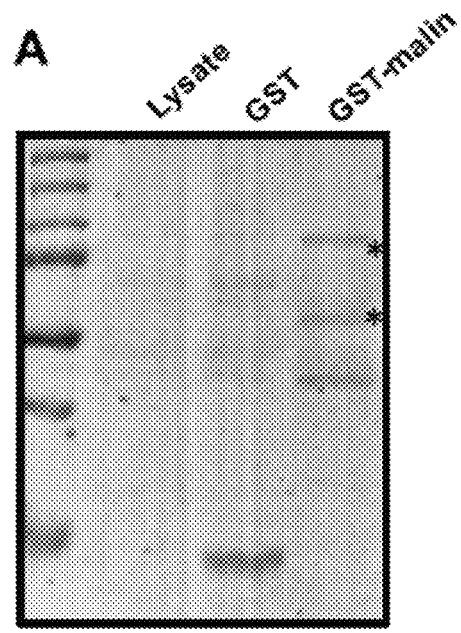
FIGS. 26A-C show images illustrating various malin interacting partners. (A) Representative Coomassie stained gel of malin interacting proteins. Total lysate, left lane; GST, middle lane; GST-malin, right lane. *=unique proteins. (B) Co-IP of HA-GDE and myc-malin. (C) Co-IP of His-GP$_{BB}$ and flag-malin (->heavy chain, * malin).
Figures 26B, 26C:
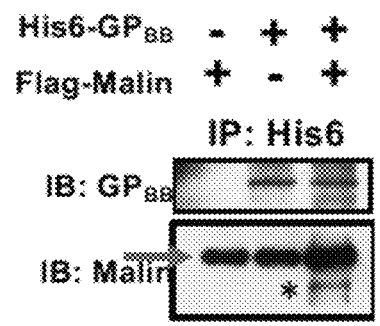

GP and GDE are novel malin targets. Malin contains a RING domain and six NHL repeats. RING domains are characteristic of a class of E3 ubiquitin ligases. NHL repeats form a six-bladed β-propeller domain that is typically involved in protein-protein interactions. To identify malin substrates, recombinant malin was purified, the protein was incubated with cell extract, and malin-bound proteins were identified using an accurate-mass, high-resolution orbitrap mass spectrometer (FIG. 26A). In addition to previously known interacting partners such as glycogen synthase (GYS) and protein targeting to glycogen (PTG), the present inventors have identified glycogen debranching enzyme (GDE) and glycogen phosphorylase brain isoform ($GP_{BB}$). The malin-GDE and malin-$GP_{BB}$ interactions were validated by co-immunoprecipitation (FIGS. 26B-C).

Figure 27A:
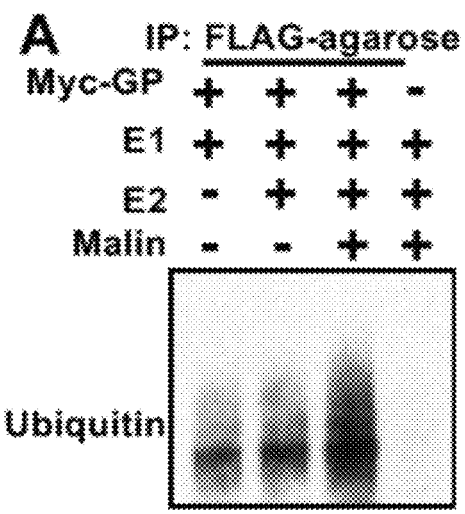
FIGS. 27A-D show graphs and an image illustrating ubiquitination and degradation by malin and malin-OE. (A) Cell-free ubiquitination assay utilizing malin and Myc-GP. (B) Malin can ubiquitinate GP$_{BB}$ in vitro. (C) Malin-OE does not result in GP degradation. (D) Histochemical staining of ES patient specimen showing increased GP$_{BB}$ in cancerous region compared to stroma.
Figure 27B:
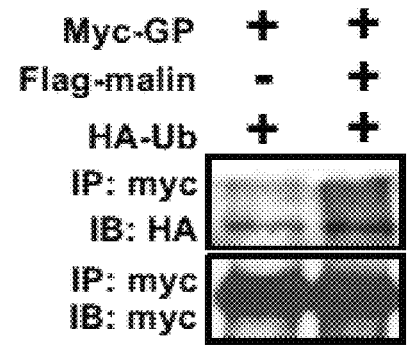
Figure 27C:
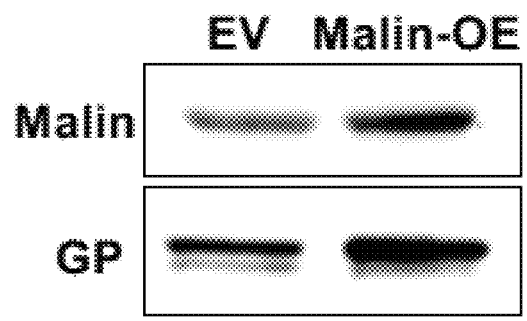
Figure 27D:
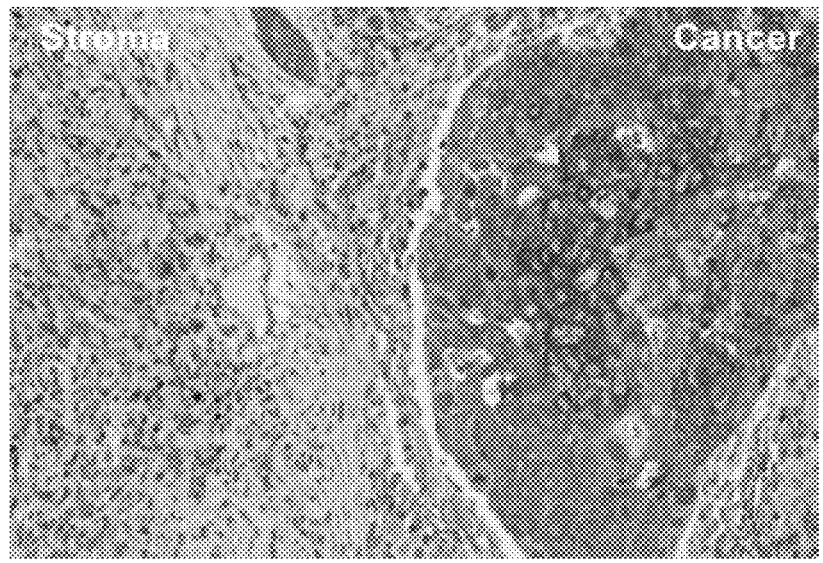

Malin-directed GP ubiquitination does not lead to proteasomal degradation. It was first tested if malin could ubiquitinate GP using purified components in a cell-free system. Myc-tagged $GP_{BB}$ was prepared using the TnT quick coupled transcription/translation system and analyzed via SDS-PAGE. Affinity-purified recombinant malin was combined with recombinant human E1 ubiquitin-activating enzyme, UbcH5a E2 ubiquitin-conjugating enzyme, ATP, and ubiquitin. $GP_{BB}$ ubiquitination was monitored by Western analysis using an anti-ubiquitin antibody. Robust GP ubiquitination was observed when E1, E2, and malin were present and this signal dramatically decreased when malin was absent (FIG. 27A). To confirm that malin can ubiquitinate $GP_{BB}$ in vitro, HEK293 cells were transfected with myc-$GP_{BB}$ and HA-ubiquitin in the presence and absence of flag-malin, immunoprecipitated myc-tagged $GP_{BB}$, and probed with anti-HA to monitor ubiquitination. Malin significantly increased the ubiquitination signal on $GP_{BB}$ (FIG. 27B). This interaction did not result in $GP_{BB}$ degradation (FIG. 27C), suggesting an alternative biological function for $GP_{BB}$ after malin ubiquitination. Additionally, an increase in $GP_{BB}$ was observed in cancer vs. surrounding stroma region of ES patient specimen using histochemical analysis (FIG. 27D).

Determine the signaling role of ES-glycogen in cellular metabolism.

AMPK is a master regulator of metabolism, controlling glucose flux, glycolysis, mitochondrial respiration and fatty acid biosynthesis. AMPK activation is anti-proliferative in nature, and AMPK activators are being clinically tested as anti-cancer treatments. As shown below, AMPK binds to glycogen through the CBM domain of the β-subunit and glycogen architecture can alter binding affinity and AMPK activity. Architectural re-organization of ES-glycogen by malin-OE in ES cell lines drastically lowers central carbon metabolite levels and carbon flux through glycolysis and the Krebs cycle, suggesting a signaling interplay between ES-glycogen and cellular metabolism. In other words, the data presented herein shows that ES-glycogen binds to AMPK with such high affinity that it renders AMPK unresponsive to upstream activation, even those used in clinical trials. Without wishing to be bound by theory, it is believed that in ES cells, aberrant ES-glycogen modulates cellular metabolism through AMPK to supply energy, nucleotides and fatty acids for cellular proliferation.

Figure 28:
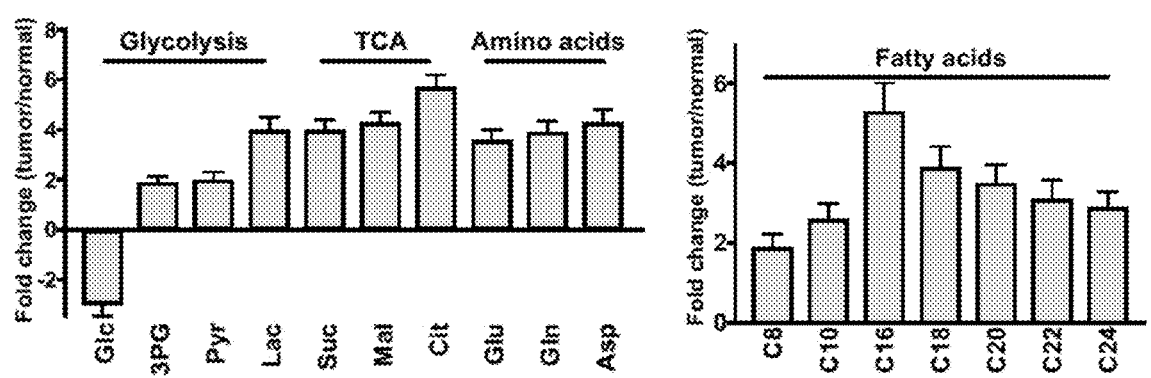
FIG. 28 shows images illustrating targeted metabolomics analysis from tumor and normal ES patient samples (n=3). Samples were snap frozen during surgery and pulverized to a fine powder. Polar metabolites and lipids were separated by 50% methanol and chloroform extraction before analysis by GCMS.
Figure 29D:
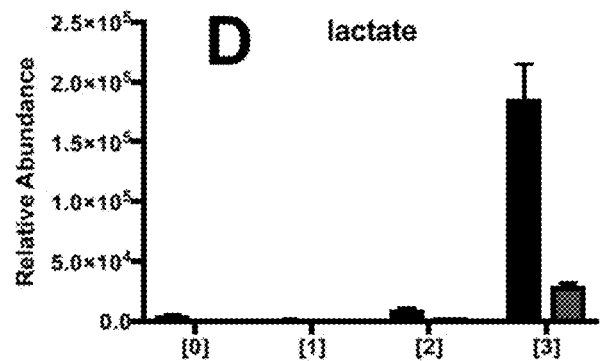
Figure 29E:
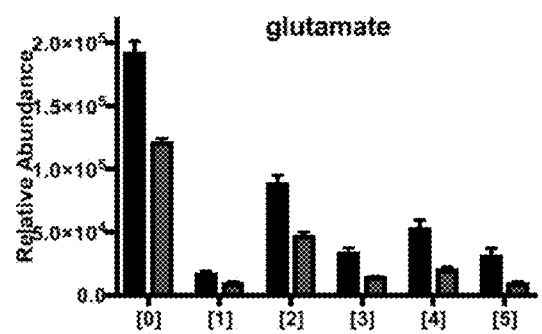
Figure 29F:
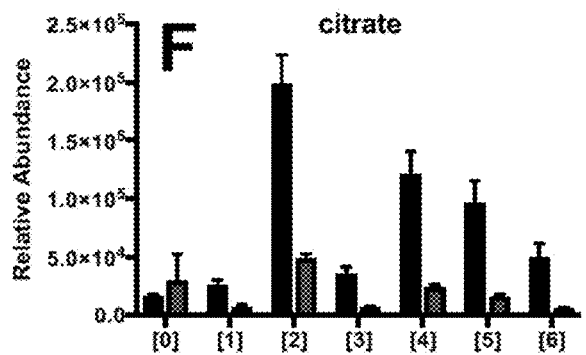
Figure 29G:
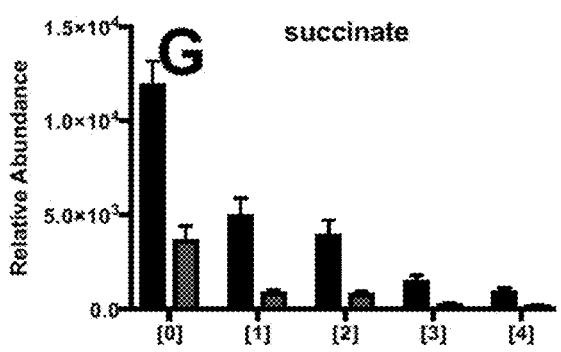
Figure 29H:
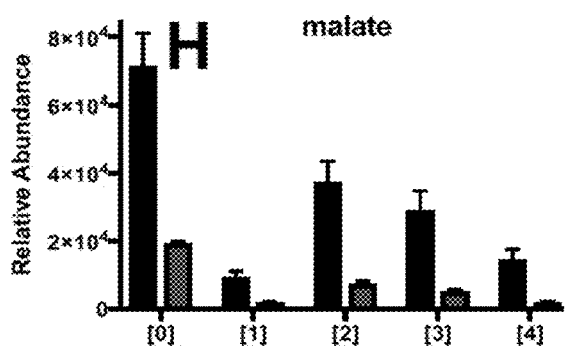
Figure 29I:
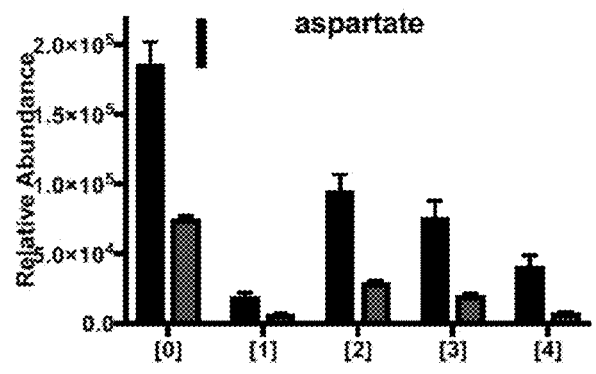

ES tumors have enhanced central carbon metabolism. PET positive and glycogen accumulation suggest altered metabolism in ES tumors. We performed a targeted metabolomics analysis between ES tumor and normal specimens from three separate patient resected during surgery. Metabolites were separated into polar and lipid fractions and analyzed using GCMS. Key metabolites in glycolysis and the Krebs cycle, including amino acids and free fatty acids, displayed a greater than 2-fold change in abundance when compared to normal tissues, likely to sustain increased rates of ES proliferation (FIG. 28). In contrast, glucose is the only metabolite significantly decreased in ES tumors, suggesting the rate of glycolysis exceeds the rate of glucose uptake. Together, this data indicate ES tumors display similar metabolic changes to AMPK deficient cells previously described by Faubert et al.

Malin overexpression suppresses glucose catabolic metabolism. Malin-OE alters glycogen architecture in ES cells to a more normal-like architecture by decreasing branching and reducing phosphate levels (FIGS. 25A-F). To investigate whether changes in glycogen architecture would alter glucose metabolism in ES cell lines, $^{13}C_6$-glucose was employed as a tracer to study carbon flux through glycolysis and the Krebs cycle in A673, TC32 and HS822T cell lines expressing either EV or malin-OE. General decreases in the relative amounts of metabolites and their isotopologues in glycolysis and the Krebs cycle were observed (FIGS. 29A-I), reversing the ES metabolic phenotype. This data suggests glycogen is a modulator of metabolism in ES tumors.

Figure 30A:
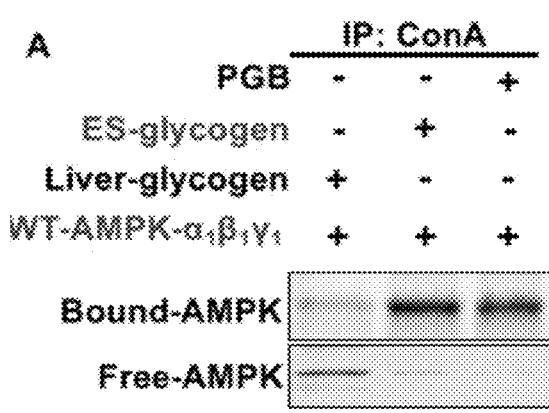
FIGS. 30A-C show images illustrating cell-free glycogen binding assay. (A) AMPK-WT has increased binding affinity to ES-glycogen and PGB. (B) AMPKβ$_{T148D}$ mutant failed to bind to all glycogen types. (C) AMPKβ$_{T148A}$ shows similar binding affinity to muscle, ES-glycogen and PGB.
Figure 30B:
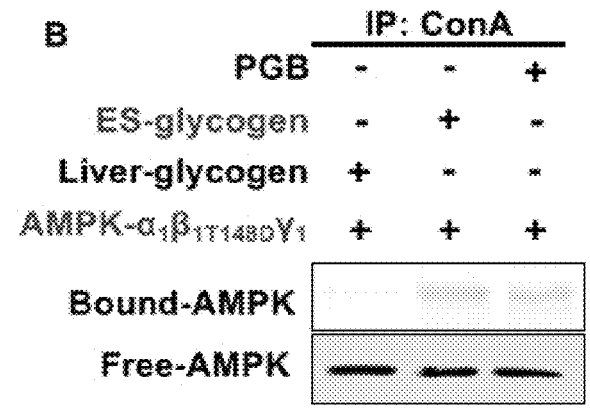
Figure 30C:
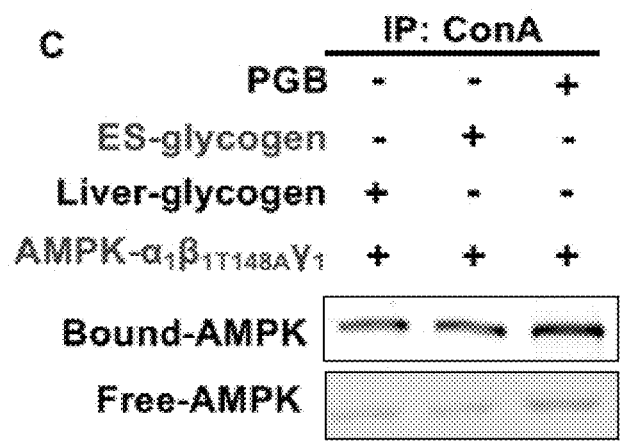

AMPK has increased binding affinity to ES-glycogen. To study AMPK interaction with ES-glycogen, a cell-free assay was established using bacterially expressed recombinant wild type and mutant AMPK trimeric complexes and purified glycogen (FIGS. 30A-C). WT-AMPK binds to ES-glycogen an PGB (control) with 7-fold higher affinity than liver glycogen. The T148D mutant has limited binding affinity to all glycogen while the T148A control has the opposite effect showing comparable binding to all glycogen subtypes (FIGS. 30A-C). This data demonstrates that ES-glycogen interacts with AMPK with high affinity and the interaction is dependent on $AMPK\beta_{T148}$.

Figure 22A:
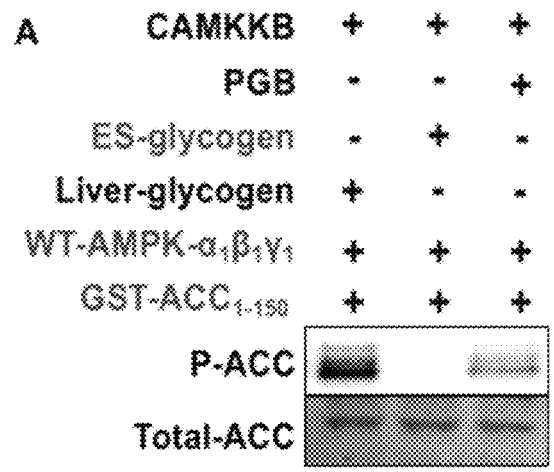
FIGS. 22A-C show images illustrating a cell-free AMPK activity assay using ACC1-150. (A) Binding of ES-glycogen and PGB greatly reduce AMPK activity. (B) AMPKβ$_{T148D}$ retain AMPK activity even after binding with ES-glycogen and PGB. (C) AMPKβ$_{T148A}$ closely mimics WT-AMPK activity after binding to different glycogen sub-types.
Figure 22B:
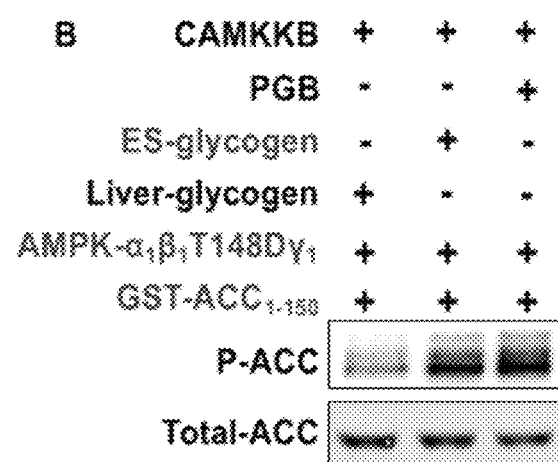
Figure 22C:
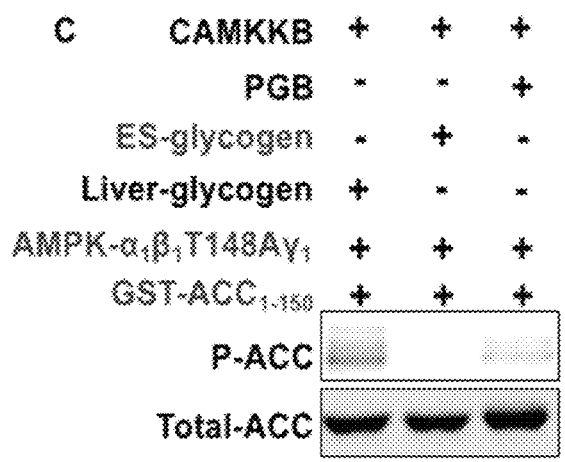

Binding to ES-glycogen abolishes AMPK activity. To test whether binding to ES-glycogen impacts activated phospho- AMPK (p-AMPK) activity, recombinant AMPK complexes were co-expressed with flag-CAMKKβ to achieve phosphorylation of the $α_{T174}$ residue. The ability of glycogen/AMPK complexes to phosphorylate a recombinant peptide corresponding to the 1-150 amino acid sequence of acetyl-CoA carboxylase ($ACC_{1-150}$) was tested. The binding to ES-glycogen resulted in the inability of AMPK to phosphorylate $ACC_{1-150}$ in the cell-free assay. This was rescued by the $β_{T148D}$ mutant but not the $β_{T148A}$ mutant (FIGS. 22A-C). This data confirms that AMPK binds to ES-glycogen with high affinity and override p-AMPK$α_{T174}$ to control its activity.

Malin-overexpression cells are more sensitive to the AMPK-activator metformin. Since aberrant ES-glycogen binds to AMPK with high affinity and is inhibitory over p-AMPK activity, malin-OE cells that normalize glycogen architecture should be more sensitive to AMPK activators. Both A673-EV and A673-malin-OE cells were treated with 2 mM metformin and both p-AMPK and p-ACC were assessed. The metformin treatment increased p-AMPK in both EV and malin-OE cell lines, but only the malin-OE cell line showed a significant increase in p-ACC (FIG. 20). This data corroborates the belief that ES-glycogen impacts p-AMPK activity in vitro.

As shown above, ES-glycogen is a direct inhibitor of p-AMPK activity. It is also noted that Malin-OE results in a shift from ES-glycogen to liver-glycogen in ES cell lines and drastically reduces glucose metabolism, suggesting re-activation of AMPK activity in these cells. In view thereof, it is believed that reversal of ES-glycogen architectural abnormalities by malin-OE will allow AMPK to respond to upstream activators in ES cell lines. That being said, a recent study elegantly described the downstream metabolic effects of AMPK inactivation. Cells harboring shRNA targeting AMPKct have aberrant central carbon metabolism including increased glycolysis, Krebs cycle and fatty acid synthesis. Since ES-glycogen completely inactivates AMPK in our cell-free assay, it is also believed that this will have pro-proliferative effects on metabolism both in vitro and in vivo.

Target ES-Glycogen as an ES Therapeutic Option.

The standard of care for Ewing sarcoma patients has not dramatically changed since the early 1990s, and overall survival for metastatic and relapsed disease remains disappointingly low. New therapeutic strategies are urgently needed for the ES treatment.

Glycogen accumulation in ES tumors has provided us with a unique therapeutic opportunity. ES-glycogen confers a cellular growth advantage by reprogramming cancer metabolism through AMPK inhibition and acting as an energy reserve. Therefore, based upon the data presented herein, it is believed that targeting ES-glycogen accumulation by inhibition of glycogen synthase provides an anti-ES strategy. More specifically, it is believed that a small molecule inhibitor that prevents aberrant glycogen accumulation will have anti-ES activity both as a single agent and in combination with AMPK activators. It is also believed that a method of preventing aberrant glycogen accumulation will synergize with AMPK activator in ES tumors. To this end, the data presented herein demonstrates that treatment with a GYS inhibitor leads to significant reductions in tumor growth in vivo.

Guaiacol as a therapeutic agent to target ES in vitro and in vivo. Glycogen metabolism has not been evaluated as an anti-cancer target in ES. Guaiacol is a naturally occurring compound that is a GYS inhibitor. Guaiacol has minimal toxicity in vivo, high bioavailability, and low cost, making it an ideal candidate for translational research. Cell viability after treatment of guaiacol was assessed at various concentrations for 48 hrs in three different ES cell lines (TC32, A673 and HS822T). Guaiacol $IC_{50}$ (50% cell viability) for all three cell lines is ~20 μM which corresponds to a 3-fold reduction in total glycogen (A673 is shown in FIGS. 31A-C). Furthermore, guaiacol treated cells are more sensitive to metformin induced AMPK activation, showing more prominent increase in p-ACC (FIG. 31D).

The efficacy of guaiacol was further tested in the xenograft model of ES. A673 cells ($10^6$) were injected subcutaneously in athymic nude mice and when the tumor reached 0.1 $cm^3$ in size daily IP injection of either PBS or guaiacol (20 mg/kg) was initiated and tumor size was measured over 15 weeks. Guaiacol is well tolerated in athymic nude mice without any adverse side effects (monitored by assessment of body weight, motor and behavior testing every second day) and can significantly reduce the highly aggressive A673 xenograft growth with a 4-fold reduction in tumor volume at the experiment endpoint (FIG. 31E). This data demonstrates that guaiacol is a promising anti-ES agent both as a single treatment or in combination with AMPK activators.

The present inventors' data also suggests AMPK activators will not be effective in ES with the presence of abnormal ES-glycogen. However, it is believed that eliminating ES-glycogen with guaiacol would enhance the anti-cancer activity of AMPK activators. It is further believed that guaiacol and AMPK activators may be combined with conventional ES chemotherapeutic agents.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. M. Rousset, S. Robine-Leon, E. Dussaulx, G. Chevalier, A. Zweibaum, Glycogen storage in foetal and malignant epithelial cells of the human colon. *Front Gastrointest Res* 4, 80-85 (1979).
2. M. Rousset, A. Zweibaum, J. Fogh, Presence of Glycogen and Growth-related Variations in 58 Cultured Human Tumor Cell Lines of Various Tissue Origins. *Cancer Research* 41, 1165-1170 (1981).
3. M. S. Gentry, J. J. Guinovart, B. A. Minassian, P. J. Roach, J. M. Serratosa, Lafora disease offers a unique window into neuronal glycogen metabolism. *Journal of Biological Chemistry* 293, 7117-7125 (2018).
4. Y. Eishi et al., Glycogen storage disease confined to the heart with deficient activity of cardiac phosphorylase kinase: A new type of glycogen storage disease. *Human Pathology* 16, 193-197 (1985).
5. W. F. Baird, E. R. Fisher, Observations concerning vacuolation and deposition of glycogen in nuclei of hepatic cells. *Lab Invest* 6, 324-333 (1957).
6. M. Himes, A. Pollister, B. Moore, The normal occurrence of hepatic intranuclear glycogen in larval and metamorphic stages of rana-pipiens. *Journal of histochemistry & cytochemistry* 4, 433-434 (1956).
7. C. Granzow, M. Kopun, H. P. Zimmermann, Role of nuclear glycogen synthase and cytoplasmic UDP glucose pyrophosphorylase in the biosynthesis of nuclear glycogen in HD33 Ehrlich-Lettré ascites tumor cells. *The Journal of Cell Biology* 89, 475 (1981).

8. H.-P. Zimmermann, V. Granzow, C. Granzow, Nuclear glycogen synthesis in ehrlich ascites cells. *Journal of Ultrastructure Research* 54, 115-123 (1976).
9. M. S. Gentry, C. A. Worby, J. E. Dixon, Insights into Lafora disease: Malin is an E3 ubiquitin ligase that ubiquitinates and promotes the degradation of laforin. *Proceedings of the National Academy of Sciences of the United States of America* 102, 8501-8506 (2005).
10. C. Roma-Mateo, P. Sanz, M. S. Gentry, Deciphering the role of malin in the Lafora progressive myoclonus epilepsy. *IUBMB life* 64, 801-808 (2012).
11. R. Yau, M. Rape, The increasing complexity of the ubiquitin code. *Nature Cell Biology* 18, 579 (2016).
12. M.-S. Kim et al., A draft map of the human proteome. *Nature* 509, 575 (2014).
13. N. Kudo et al., Leptomycin B Inhibition of Signal-Mediated Nuclear Export by Direct Binding to CRM1. *Experimental Cell Research* 242, 540-547 (1998).
14. X. Yu, S. Li, Non-metabolic functions of glycolytic enzymes in tumorigenesis. *Oncogene* 36, 2629-2636 (2017).
15. A. E. Boukouris, S. D. Zervopoulos, E. D. Michelakis, Metabolic Enzymes Moonlighting in the Nucleus: Metabolic Regulation of Gene Transcription. *Trends in Biochemical Sciences* 41, 712-730 (2016).
16. J. Chen et al., Compartmentalized activities of the pyruvate dehydrogenase complex sustain lipogenesis in prostate cancer. *Nat Genet* 50, 219-228 (2018).
17. G. Sutendra et al., A Nuclear Pyruvate Dehydrogenase Complex Is Important for the Generation of Acetyl-CoA and Histone Acetylation. *Cell* 158, 84-97 (2014).
18. R. C. Sun et al., Noninvasive liquid diet delivery of stable isotopes into mouse models for deep metabolic network tracing. *Nature Communications* 8, 1646 (2017).
19. W. L. Bloom, G. T. Lewis, M. Z. Schumpert, T. M. Shen, Glycogen fractions of liver and muscle. *Journal of Biological Chemistry* 188, 631-636 (1951).
20. A. Miyanaga et al., Antitumor activity of histone deacetylase inhibitors in non-small cell lung cancer cells: development of a molecular predictive model. *Molecular Cancer Therapeutics* 7, 1923 (2008).
21. J. E. Bolden, M. J. Peart, R. W. Johnstone, Anticancer activities of histone deacetylase inhibitors. *Nature Reviews Drug Discovery* 5, 769 (2006).
22. C. Lu et al., IDH mutation impairs histone demethylation and results in a block to cell differentiation. *Nature* 483, 474-478 (2012).
23. J. R. Toro et al., Mutations in the Fumarate Hydratase Gene Cause Hereditary Leiomyomatosis and Renal Cell Cancer in Families in North America. *American Journal of Human Genetics* 73, 95-106 (2003).
24. M. Xiao et al., Inhibition of alpha-KG-dependent histone and DNA demethylases by fumarate and succinate that are accumulated in mutations of FH and SDH tumor suppressors. *Genes Dev* 26, 1326-1338 (2012).
25. K. E. Wellen et al., ATP-Citrate Lyase Links Cellular Metabolism to Histone Acetylation. *Science* 324, 1076 (2009).
26. X. Gao et al., Acetate functions as an epigenetic metabolite to promote lipid synthesis under hypoxia. *Nature Communications* 7, 11960 (2016).
27. V. Bulusu et al., Acetate Recapturing by Nuclear Acetyl-CoA Synthetase 2 Prevents Loss of Histone Acetylation during Oxygen and Serum Limitation. *Cell Reports* 18, 647-658 (2017).
28. P. Mews et al., Acetyl-CoA synthetase regulates histone acetylation and hippocampal memory. *Nature* 546, 381 (2017).
29. H. Cedar, Y. Bergman, Linking DNA methylation and histone modification: patterns and paradigms. *Nature Reviews Genetics* 10, 295 (2009).
30. S. A. Belinsky et al., Inhibition of DNA Methylation and Histone Deacetylation Prevents Murine Lung Cancer. *Cancer Research* 63, 7089 (2003).
31. H. Zhang et al., Lkb1 inactivation drives lung cancer lineage switching governed by Polycomb Repressive Complex 2. *Nat Commun* 8, 14922 (2017).
32. O. Baba, Production of monoclonal antibody that recognizes glycogen and its application for immunohistochemistry. *Kokubyo Gakkai Zasshi* 60, 264-287 (1993).
33. E. Schreiber et al., Astrocytes and glioblastoma cells express novel octamer-DNA binding proteins distinct from the ubiquitous Oct-1 and B cell type Oct-2 proteins. *Nucleic Acids Research* 18, 5495-5503 (1990).
34. T. Nagata, R. S. Redman, R. Lakshman, Isolation of intact nuclei of high purity from mouse liver. *Analytical Biochemistry* 398, 178-184 (2010).
35. J.-Y. Jung, M.-K. Oh, Isotope labeling pattern study of central carbon metabolites using GC/MS. *Journal of Chromatography* B 974, 101-108 (2015).
36. James I. MacRae et al., Mitochondrial Metabolism of Glucose and Glutamine Is Required for Intracellular Growth of <em>Toxoplasma gondii</em>. *Cell Host & Microbe* 12, 682-692 (2012).
37. M. J. Dagley, M. J. McConville, DExSI: a new tool for the rapid quantitation of 13C-labelled metabolites detected by GC-MS. *Bioinformatics* 34, 1957-1958 (2018).
38. Grünewald, T. G. P., et al., Ewing sarcoma. Nature Reviews Disease Primers, 2018. 4(1): P. 5.
39. Torres, R., et al., Engineering human tumour-associated chromosomal translocations with the RNA-guided CRISPR-Cas9 system. Nature communications, 2014. 5: p. 3964.
40. Riggi, N., et al., EWS-FLI1 utilizes divergent chromatin remodeling mechanisms to directly activate or repress enhancer elements in Ewing sarcoma. Cancer cell, 2014. 26(5): p. 668-681.
41. Duhaylongsod, F. G., et al., Lung tumor growth correlates with glucose metabolism measured by fluorine-18 fluorodeoxyglucose positron emission tomography. The Annals of Thoracic Surgery, 1995. 60(5): p. 1348-1352.
42. Chung, J. K., et al., Comparison of F-18 fluorodeoxyglucose uptake with glucose transporter-1 expression and proliferation rate in human glioma and non-small-cell lung cancer. Nuclear Medicine Communications, 2004. 25.
43. Rousset, M., A. Zweibaum, and J. Fogh, Presence of Glycogen and Growth-related Variations in 58 Cultured Human Tumor Cell Lines of Various Tissue Origins. Cancer Research, 1981. 41(3): p. 11651170.
44. Rousset, M., et al., Presence and Cell Growth-related Variations of Glycogen in Human Colorectal Adenocarcinoma Cell Lines in Culture. Cancer Research, 1979. 39(2 Part 1): p. 531-534.
45. Rousset, M., et al., Kinetics of glycogen levels in asynchronous and synchronous cultures of a human colon carcinoma cell line, HT 29. Front Gastrointest Res, 1979. 4: p. 73-9.
46. Rousset, M., et al., Glycogen storage in foetal and malignant epithelial cells of the human colon. Front Gastrointest Res, 1979. 4: p. 80-5.

47. Staedel, C. and J.-P. Beck, Resurgence of glycogen synthesis and storage capacity in cultured hepatoma cells. Cell Differentiation, 1978. 7(1): p. 61-71.
48. Sato, A., et al., Glycogen-rich clear cell carcinoma of the breast showing carcinomatous lymphangiosis and extremely aggressive clinical behavior. Pathol Int, 2015. 65(12): p. 674-6.
49. Favaro, E., et al., Glucose Utilization via Glycogen Phosphorylase Sustains Proliferation and Prevents Premature Senescence in Cancer Cells. Cell Metabolism, 2012. 16(6): p. 751-764.
50. Hochachka, P., *Defense strategies against hypoxia and hypothermia.* Science, 1986. 231(4735): p. 234-241.
51. Crass M F and G. Pieper, *Lipid and glycogen metabolism in the hypoxic heart: effects of epinephrine.* American Journal of Physiology—Legacy Content, 1975. 229(4): p. 885-889.
52. Iida, Y., et al., Hypoxia promotes glycogen synthesis and accumulation in human ovarian clear cell carcinoma. Int J Oncol, 2012. 40(6): p. 2122-30.
53. Pescador, N., et al., Hypoxia promotes glycogen accumulation through hypoxia inducible factor (HIF)-mediated induction of glycogen synthase 1. PLoS One, 2010. 5(3): p. e9644.
54. Shen, G. M., et al., Hypoxia-inducible factor 1-mediated regulation of PPP1R3C promotes glycogen accumulation in human MCF-7 cells under hypoxia. FEBS Lett, 2010. 584(20): p. 4366-72.
55. Chen, J., et al., Gain of Glucose-Independent Growth upon Metastasis of Breast Cancer Cells to the Brain. Cancer Research, 2015. 75(3): p. 554-565.
56. Zois, C. E. and A. L. Harris, Glycogen metabolism has a key role in the cancer microenvironment and provides new targets for cancer therapy. Journal of Molecular Medicine, 2016. 94(2): p. 137-154.
57. Liu, J., et al., Succinate Dehydrogenase 5 (SDH5) Regulates Glycogen Synthase Kinase 3β-β-Catenin-mediated Lung Cancer Metastasis. Journal of Biological Chemistry, 2013. 288(41): p. 29965-29973.
58. Zois, C. E. and A. L. Harris, Glycogen metabolism has a key role in the cancer microenvironment and provides new targets for cancer therapy. Journal of Molecular Medicine (Berlin, Germany), 2016. 94: p. 137-154.
59. Costill, D. L., et al., *Glycogen Depletion Pattern in Human Muscle Fibres During Distance Running.* Acta Physiologica Scandinavica, 1973. 89(3): p. 374-383.
60. Hultman, E. and L. H. Nilsson, Liver Glycogen in Man. Effect of Different Diets and Muscular Exercise, in Muscle Metabolism During Exercise: Proceedings of a Karolinska Institutet Symposium held in Stockholm, Sweden, Sep. 6-9, 1970 Honorary guest: E Hohwü Christensen, B. Pernow and B. Saltin, Editors. 1971, Springer US: Boston, Mass. p. 143-151.
61. Krebs, H. A., et al., Renal gluconeogenesis. The effect of diet on the gluconeogenic capacity of rat-kidney-cortex slices. Biochemical Journal, 1963. 86(1): p. 22-27.
62. Brown, A. M. and B. R. Ransom, *Astrocyte glycogen and brain energy metabolism.* Glia, 2007. 55(12): p. 1263-1271.
63. GIBB, R. P. and R. E. STOWELL, *GLYCOGEN IN HUMAN BLOOD CELLS.* Blood, 1949. 4(5): p. 569579.
64. Hers, H. G., *The Control of Glycogen Metabolism in the Liver.* Annual Review of Biochemistry, 1976. 45(1): p. 167-190.
65. Daran, J. M., et al., Genetic and Biochemical Characterization of the UGP1 Gene Encoding the UDP-Glucose Pyrophosphorylase from Saccharomyces cerevisiae. European Journal of Biochemistry, 1995. 233(2): p. 520-530.
66. Ros, S., et al., Control of Liver Glycogen Synthase Activity and Intracellular Distribution by Phosphorylation. Journal of Biological Chemistry, 2009. 284(10): p. 6370-6378.
67. Thon, V. J., M. Khalil, and J. F. Cannon, *Isolation of human glycogen branching enzyme cDNAs by screening complementation in yeast.* Journal of Biological Chemistry, 1993. 268(10): p. 7509-7513.
68. Johnson, L. N., Glycogen phosphorylase: control by phosphorylation and allosteric effectors. The FASEB Journal, 1992. 6(6): p. 2274-82.
69. Agius, L., *Role of glycogen phosphorylase in liver glycogen metabolism.* Molecular Aspects of Medicine, 2015. 46: p. 34-45.
70. Sinnett-Smith, J., et al., Metformin inhibition of mTORC1 activation, DNA synthesis and proliferation in pancreatic cancer cells: Dependence on glucose concentration and role of AMPK. Biochemical and Biophysical Research Communications, 2013. 430(1): p. 352-357.
71. Mihaylova, M. M. and R. J. Shaw, The AMPK signalling pathway coordinates cell growth, autophagy and metabolism. Nature Cell Biology, 2011. 13: p. 1016.
72. Hardie, D. G. and D. R. Alessi, LKB1 and AMPK and the cancer-metabolism link—ten years after. BMC Biology, 2013. 11(1): p. 36.
73. Hardie, D. G., AMPK—Sensing Energy while Talking to Other Signaling Pathways. Cell Metabolism, 2014. 20(6): p. 939-952.
74. Woods, A., et al., Ca2+/calmodulin-dependent protein kinase kinase-beta acts upstream of AMP-activated protein kinase in mammalian cells. Cell Metab, 2005. 2(1): p. 21-33.
75. Shackelford, D. B. and R. J. Shaw, The LKB1-AMPK pathway: metabolism and growth control in tumour suppression. Nature Reviews Cancer, 2009. 9: p. 563.
76. Shaw, R. J., et al., The tumor suppressor LKB1 kinase directly activates AMP-activated kinase and regulates apoptosis in response to energy stress. Proceedings of the National Academy of Sciences of the United States of America, 2004. 101(10): p. 3329.
77. Marsin, A. S., et al., Phosphorylation and activation of heart PFK-2 by AMPK has a role in the stimulation of glycolysis during ischaemia. Current Biology, 2000. 10(20): p. 1247-1255.
78. Fediuc, S., M. P. Gaidhu, and R. B. Ceddia, Regulation of AMP-activated protein kinase and acetyl-CoA carboxylase phosphorylation by palmitate in skeletal muscle cells. Journal of Lipid Research, 2006. 47(2): p. 412-420.
79. Houde, V. P., et al., AMPK β1 reduces tumor progression and improves survival in p53 null mice. Molecular Oncology, 2017. 11(9): p. 1143-1155.
80. Duan, W., et al., Desmoplasia suppression by metformin-mediated AMPK activation inhibits pancreatic cancer progression. Cancer Letters, 2017. 385: p. 225-233.
81. Faubert, B., et al., AMPK Is a Negative Regulator of the Warburg Effect and Suppresses Tumor Growth In Vivo. Cell Metabolism, 2013. 17(1): p. 113-124.
82. Mobbs, Jesse I., et al., Determinants of oligosaccharide specificity of the carbohydrate-binding modules of AMP-activated protein kinase. Biochemical Journal, 2015. 468 (2): p. 245.
83. Li, X., et al., Structural basis of AMPK regulation by adenine nucleotides and glycogen. Cell Research, 2014. 25: p. 50.

84. Koay, A., et al., AMPK β subunits display isoform specific affinities for carbohydrates. FEBS Letters, 2010. 584(15): p. 3499-3503.
85. Oligschlaeger, Y., et al., The Recruitment of AMP-activated Protein Kinase to Glycogen Is Regulated by Autophosphorylation. Journal of Biological Chemistry, 2015. 290(18): p. 11715-11728.
86. McBride, A., et al., The Glycogen-Binding Domain on the AMPK (3 Subunit Allows the Kinase to Act as a Glycogen Sensor. Cell Metabolism, 2009. 9(1): p. 23-34.
87. Hunter, R. W., et al., Molecular Mechanism by Which AMP-Activated Protein Kinase Activation Promotes Glycogen Accumulation in Muscle. Diabetes, 2011. 60(3): p. 766.
88. Li, C., O. Powell Prudence, and G. Gilbert Robert, Recent progress toward understanding the role of starch biosynthetic enzymes in the cereal endosperm, in Amylase. 2017. p. 59.
89. Powell, P. O., et al., Acid hydrolysis and molecular density of phytoglycogen and liver glycogen helps understand the bonding in glycogen alpha (composite) particles. PLoS One, 2015. 10(3): p. e0121337.
90. Deng, B., et al., The Mechanism for Stopping Chain and Total-Molecule Growth in Complex Branched Polymers, Exemplified by Glycogen. Biomacromolecules, 2015. 16(6): p. 1870-2.
91. Nitschke, F., et al., Hyperphosphorylation of Glucosyl C6 Carbons and Altered Structure of Glycogen in the Neurodegenerative Epilepsy Lafora Disease. Cell Metabolism, 2013. 17(5): p. 756-767.
92. Roach, P. J., et al., *Glycogen and its metabolism: some new developments and old themes*. The Biochemical journal, 2012. 441(3): p. 763-787.
93. Tagliabracci, Vincent S., et al., *Phosphate Incorporation during Glycogen Synthesis and Lafora Disease*. Cell Metabolism, 2011. 13(3): p. 274-282.
94. DePaoli-Roach, A. A., et al., Glycogen Phosphomonoester Distribution in Mouse Models of the Progressive Myoclonic Epilepsy, Lafora Disease. The Journal of Biological Chemistry, 2015. 290(2): p. 841-850.
95. Bertoft, E., Understanding Starch Structure: Recent Progress. Agronomy, 2017. 7(3).
96. Gentry, M. S., C. A. Worby, and J. E. Dixon, Insights into Lafora disease: malin is an E3 ubiquitin ligase that ubiquitinates and promotes the degradation of laforin. Proc Natl Acad Sci USA, 2005. 102(24): p. 8501-6.
97. Worby, C. A., M. S. Gentry, and J. E. Dixon, Malin decreases glycogen accumulation by promoting the degradation of protein targeting to glycogen (PTG). J Biol Chem, 2008. 283(7): p. 4069-76.
98. Solaz-Fuster, M. C., et al., Regulation of glycogen synthesis by the laforin-malin complex is modulated by the AMP-activated protein kinase pathway. Hum Mol Genet, 2008. 17(5): p. 667-78.
99. Vilchez, D., et al., Mechanism suppressing glycogen synthesis in neurons and its demise in progressive myoclonus epilepsy. Nat Neurosci, 2007. 10(11): p. 1407-13.
100. Cheng, A., et al., A role for AGL ubiquitination in the glycogen storage disorders of Lafora and Cori's disease. Genes Dev., 2007. 21(19): p. 2399-2409.
101. Berkovic, S. F., N. K. So, and F. Andermann, *Progressive myoclonus epilepsies: clinical and neurophysiological diagnosis*. J Clin Neurophysiol, 1991. 8(3): p. 261-74.
102. Gentry, M. S., J. E. Dixon, and C. A. Worby, *Lafora disease: insights into neurodegeneration from plant metabolism*. Trends Biochem Sci, 2009. 34(12): p. 628-39.
103. Harriman, D. G., J. H. Millar, and A. C. Stevenson, Progressive familial myoclonic epilepsy in three families: its clinical features and pathological basis. Brain, 1955. 78(3): p. 325-49.
104. Hodskins, M. B. and P. I. Yakovlev, Anatomico-clinical observations on myclonus in epileptics and on related symptom complexes. American Journal of Psychiatry, 1930. 86: p. 827-848.
105. Minassian, B. A., Lafora's disease: towards a clinical, pathologic, and molecular synthesis. Pediatr Neurol, 2001. 25(1): p. 21-9.
106. Nitschke, F., et al., Abnormal glycogen chain length pattern, not hyperphosphorylation, is critical in Lafora disease. EMBO Molecular Medicine, 2017. 9(7): p. 906.
107. Fan, T. W. M., et al., Stable isotope-resolved metabolomics and applications for drug development. Pharmacology & Therapeutics, 2012. 133(3): p. 366-391.
108. Lane, A. N., R. M. Higashi, and T. W.-M. Fan, Preclinical models for interrogating drug action in human cancers using Stable Isotope Resolved Metabolomics (SIRM). Metabolomics, 2016. 12(7): p. 1-15.
109. Fan, T. W.-M., et al., Stable isotope resolved metabolomics analysis of ribonucleotide and RNA metabolism in human lung cancer cells. Metabolomics, 2012. 8(3): p. 517-527.
110. Higashi, R. M., et al., Stable Isotope-Labeled Tracers for Metabolic Pathway Elucidation by GC-MS and FT-MS, in Mass Spectrometry in Metabolomics: Methods and Protocols, D. Raftery, Editor. 2014, Springer New York: New York, NY. p. 147-167.
111. Cokorinos, E. C., et al., Activation of skeletal muscle AMPK promotes glucose disposal and glucose lowering in non-human primates and mice. Cell metabolism, 2017. 25(5): p. 1147-1159. e10.
112. Kishton, R. J., et al., AMPK Is Essential to Balance Glycolysis and Mitochondrial Metabolism to Control T-ALL Cell Stress and Survival. Cell Metab, 2016. 23(4): p. 649-62.
113. Roma-Mateo, C., P. Sanz, and M. S. Gentry, *Deciphering the role of malin in the lafora progressive myoclonus epilepsy*. IUBMB Life, 2012. 64(10): p. 801-8.
114. Gentry, M. S., C. Roma-Mateo, and P. Sanz, Laforin, a protein with many faces: glucan phosphatase, adapter protein, et alii. Febs J, 2013. 280(2): p. 525-37.
115. Baba, O., [*Production of monoclonal antibody that recognizes glycogen and its application for immunohistochemistry*]. Kokubyo Gakkai zasshi. The Journal of the Stomatological Society, Japan, 1993. 60(2): p. 264-287.
116. Contreras, C. J., et al., *Incorporation of phosphate into glycogen by glycogen synthase*. Archives of Biochemistry and Biophysics, 2016. 597: p. 21-29.
117. Raththagala, M., et al., Structural Mechanism of Laforin Function in Glycogen Dephosphorylation and Lafora Disease. Molecular Cell, 2015. 57(2): p. 261-272.
118. Chan, E. M., et al., Mutations in NHLRC1 cause progressive myoclonus epilepsy. Nat Genet, 2003. 35(2): p. 125-7.
119. Borden, K. L. a. P. S. F., *The RING finger domain: a recent example of a sequence-structure family*. Current Opinion in Structural Biology, 1996. 6(3): p. 395-401.
120. Tyers, M. a. A. R. W., *One Ring to Rule a Superfamily of E3 Ubiquitin Ligases*. Science, 1999. 284(5414): p. 601-604.
121. Edwards, T. A., et al., Model of the brain tumor-Pumilio translation repressor complex. Genes Dev, 2003. 17(20): p. 2508-13.

122. Slack, F. J. and G. Ruvkun, A novel repeat domain that is often associated with RING finger and B-box motifs. Trends Biochem Sci, 1998. 23(12): p. 474-5.
123. Worby, C. A., M. S. Gentry, and J. E. Dixon, Malin decreases glycogen accumulation by promoting the degradation of protein targeting to glycogen (PTG). The Journal of biological chemistry, 2008. 283(7): p. 4069-4076.
124. Vilchez, D., et al., Mechanism suppressing glycogen synthesis in neurons and its demise in progressive myoclonus epilepsy. Nature neuroscience, 2007. 10(11): p. 1407.
125. Yau, R. and M. Rape, *The increasing complexity of the ubiquitin code*. Nature Cell Biology, 2016. 18: p. 579.
126. Akutsu, M., I. Dikic, and A. Bremm, *Ubiquitin chain diversity at a glance*. Journal of Cell Science, 2016. 129(5): p. 875.
127. Yau, R. and M. Rape, *The increasing complexity of the ubiquitin code*. Nature cell biology, 2016. 18(6): p. 579.
128. Sun, Ramon C. and Nicholas C. Denko, Hypoxic Regulation of Glutamine Metabolism through HIF 1 and SIAH2 Supports Lipid Synthesis that Is Necessary for Tumor Growth. Cell Metabolism, 2014. 19(2): p. 285-292.
129. Nagata, T., R. S. Redman, and R. Lakshman, *Isolation of intact nuclei of high purity from mouse liver*. Analytical Biochemistry, 2010. 398(2): p. 178-184.
130. Rose, Christopher M., et al., Highly Multiplexed Quantitative Mass Spectrometry Analysis of Ubiquitylomes. Cell Systems, 2016. 3(4): p. 395-403.e4.
131. Luo, Z., M. Zang, and W. Guo, AMPK as a metabolic tumor suppressor: control of metabolism and cell growth. Future oncology, 2010. 6(3): p. 457-470.
132. Shaw, R. J., et al., The tumor suppressor LKB1 kinase directly activates AMP-activated kinase and regulates apoptosis in response to energy stress. Proceedings of the National Academy of Sciences, 2004. 101(10): p. 3329-3335.
133. Green, A. S., et al., The LKB1/AMPK signaling pathway has tumor suppressor activity in acute myeloid leukemia through the repression of mTOR-dependent oncogenic mRNA translation. Blood, 2010: p. blood-2010-02-269837.
134. Deng, P., et al., Quantitative profiling of carbonyl metabolites directly in crude biological extracts using chemoselective tagging and nanoESI-FTMS. Analyst, 2018. 143(1): p. 311-322.
135. Sun, R. C., et al., Noninvasive liquid diet delivery of stable isotopes into mouse models for deep metabolic network tracing. Nature Communications, 2017. 8(1): p. 1646.
136. Kakhlon, O., et al., Guaiacol can be a drug-candidate for treating Adult Polyglucosan Body Disease (P5.461). Neurology, 2018. 90(15 Supplement).
137. Murakami, H. and K. Yamafuji, *Antitumor activities of polyphenols*. Science bulletin of the Faculty of Agriculture, Kyushu University, 1968. 24(1): p. 19-24.
138. Kakhlon, O., et al., Guaiacol as a drug candidate for treating adult polyglucosan body disease. JCI Insight, 2018. 3(17).
139. Liu, P. and J. T. G. Hwang, Quick calculation for sample size while controlling false discovery rate with application to microarray analysis. Bioinformatics, 2007. 23(6): p. 739-746.
140. Benjamini, Y. and D. Yekutieli, The control of the false discovery rate in multiple testing under dependency. 2001: p. 1165-1188.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method of treating cancer, the method comprising:
   administering to a subject in need thereof an effective amount of 2-methoxyphenol (Guaiacol);
   wherein the cancer is characterized by abnormal glycogen with a hyper-phosphorylated and hyper-branched architecture as compared to normal glycogen.

2. The method if claim 1, wherein the cancers Ewing's sarcoma.

3. The method of claim 1, further comprising administering an additional therapeutic to the subject, the additional therapeutic being selected from the group consisting of a chemotherapy drug, an AMPK activator, an alkylating agent, an antimetabolite, a plant alkaloid, a DNA targeting agent, radiation therapy, and combinations thereof.

4. The method of claim 3, wherein the additional therapeutic is the AMPK. activator.

5. The method of claim 3, wherein the additional therapeutic is the AMPK activator and a chemotherapy drug.

6. The method of claim 1, further comprising administering a pharmaceutically-acceptable carrier with the compound, the pharmaceutically-acceptable carrier and the compound forming a pharmaceutical composition.

7. A method of treating cancer, the method comprising:
   administering to a subject in need thereof an effective amount of 2-methoxyphenol (Guaiacol); and
   administering an additional therapeutic to the subject, the additional therapeutic being selected from the group consisting of an AMPK activator and a chemotherapy drug;
   wherein the cancer is Ewing's sarcoma.

* * * * *